(12) United States Patent
Liu et al.

(10) Patent No.: US 7,524,840 B2
(45) Date of Patent: Apr. 28, 2009

(54) 7,8-DISUBSTITUTED PYRAZOLOBENZODIAZEPINES

(75) Inventors: Jin-Jun Liu, Warren, NJ (US); Kin-Chun Luk, North Caldwell, NJ (US); Giacomo Pizzolato, Glen Ridge, NJ (US); Yi Ren, Warren, NJ (US); Kshitij Chhabilbhai Thakkar, Clifton, NJ (US); Peter Michael Wovkulich, Nutley, NJ (US); Zhuming Zhang, Hillsborough, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 528 days.

(21) Appl. No.: 11/244,251

(22) Filed: Oct. 5, 2005

(65) Prior Publication Data

US 2006/0079511 A1 Apr. 13, 2006

Related U.S. Application Data

(60) Provisional application No. 60/618,174, filed on Oct. 13, 2004.

(51) Int. Cl.
*A61P 35/00* (2006.01)
*A61K 31/55* (2006.01)
*C07D 487/04* (2006.01)

(52) U.S. Cl. .................. 514/219; 514/220; 540/555; 540/557

(58) Field of Classification Search ................. 514/219, 514/220; 540/555, 557
See application file for complete search history.

(56) References Cited

U.S. PATENT DOCUMENTS

| | | | |
|---|---|---|---|
| 3,681,341 | A | 8/1972 | Earley et al. |
| 5,621,082 | A | 4/1997 | Xiong et al. |
| 6,440,959 | B1 | 8/2002 | Ding et al. |

FOREIGN PATENT DOCUMENTS

| | | |
|---|---|---|
| EP | 0 666 270 | 8/1995 |
| WO | WO 97/16447 | 5/1997 |
| WO | WO 97/20842 | 6/1997 |
| WO | WO 98/05335 | 2/1998 |
| WO | WO 00/64900 | 11/2000 |

OTHER PUBLICATIONS

Folkman, *New England Journal of Medicine*, 285:1182-86 (1971).
Algire, et al., *J. Nat. Cancer Inst.*, 6:73-85 (1945).
Gimbrone, Jr., et al., *J. Nat. Cancer Inst.*, 52:413-427 (1974).
Gimbrone, Jr. et al., *J. Exp. Med.*, 136:261-76 (1972).
Knighton, *British, J. Cancer*, 35:347-56 (1977).
Lien, et al., *Surgery*, 68:334-40 (1970).
Folkman, et al., *Nature*, 339:58-61 (1989).
Kim et al., *Nature*, 362:841-44 (1993).
Hori, et al., *Cancer, Res.* 51:6180-84 (1991).
Gross, et al., *Proc. Am. Assoc. Cancer Res.*, 31:79 (1990).
Ingber, et al., *Nature*, 348:555-57 (1990).
Weidner, et al., *New Eng. J. of Med.*, 324:1-8 (1991).
Weidner, et al., *J. Nat. Cancer Inst.*, 84:1875-87 (1992).
Weidner, et al., *Am. J. Pathol.*, 143 (2):401-09 (1993).
Srivastava, et al., *Am. J. Pathol.*, 133:419-23 (1988).
Nguyen, et al., *J. Nat. Cancer, Inst.*, 85:241-42 (1993).
Mazitschek et al. Current Opinion in Chemical Biology, 8(4): 432-441 (2004).
Underiner, et al., Current Medicinal Chemistry, 11(6): 731-745 (2004).
Manley, et al., Biochimica et Biophysica Acta, 1697(1-2): 17-27 (2004).
Alessi, et al., Biochimica et Biophysica Acta, 1654(1): 39-49 (2004).
Tortora, et al., Current Pharmaceutical Design, 10(1): 11-26 (2004).
Coleman et al., *Annual Reports in Medicinal Chemistry*, 32: 171-179 (1997).
Nasmyth, K., *Science*, 274: 1643-1677 (Dec. 6, 1996) 24.
Kamb, *Trends in Genetics*, 11: 136-140 (1995).
Webster, *Exp. Opin. Invest. Drugs*, 7: 865-887 (1998).
Berghot, *Arch. Pharm.* 325:285-289 (1992).
Scheibye, et al., *Bulletin des Societes Chimiques Belges*, 87: 229-38 (1978).
Jesberger, et al., *Synthesis*, 1929-1958 (2003).
Walser, et al., Chemistry of Heterocyclic Compounds, Chichester, United Kingdom, vol. 50: 431-543 (1991).
Walser, et al., Chemistry of Heterocyclic Compounds, Chichester, United Kingdom, vol. 50: 545-629 (1991).
Walser, et al., Chemistry of Heterocyclic Compounds, Chichester, United Kingdom, vol. 50: 631-848 (1991).
Walser, et al., Chemistry of Heterocyclic Compounds, Chichester, United Kingdom, vol. 50: 849-946 (1991).
Archer, G. A.; et al., Chemical Reviews, The Chemistry of Benzodiazepines, 68: 747-84 (1968).
Sternbach, et al., Journal of Organic Chemistry, 27: 3788-96 (1962).
Toyoda, et al., *Tetrahedron Letters*, 21: 173-6 (1980).
Castelló et al., *Tetrahedron Letters*, 26: 2489-92 (1985).
Sugasawa, et al., Journal of Heterocyclic Chemistry, 16(3): 445-8 (1979).
Leroux, et al., Journal of Organic Chemistry, 68: 4693-4699 (2003).
Taniguchi et al., *Tetrahedron Letters*, 39: 4679-4682 (1998).
Abstract corresponding to Document B4 (WO 97/20842) Jun. 12, 1997.

*Primary Examiner*—Brenda L Coleman
(74) *Attorney, Agent, or Firm*—George W. Johnston; Patricia S. Rocha-Tramaloni; Gene J. Yao

(57) ABSTRACT

The present invention provides compounds of formula I

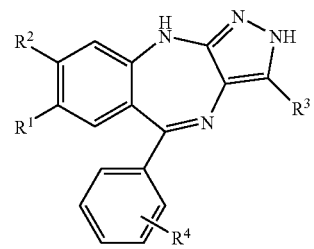

wherein $R^1$, $R^2$, $R^3$, $R^4$, and $R^5$ are described herein. The invention also provides syntheses for preparation of such compounds and pharmaceutical compositions containing them. The invention further provides methods for inhibiting kinases, in particular CDK2, for inhibiting angiogenesis, and for treating cancers, in particular breast, colon, prostate, and lung cancer.

58 Claims, No Drawings

7,8-DISUBSTITUTED PYRAZOLOBENZODIAZEPINES

PRIORITY TO RELATED APPLICATIONS

This application claims the benefit of U.S. Provisional Application No. 60/618,174, filed Oct. 13, 2004, which is hereby incorporated by reference in its entirety.

FIELD OF THE INVENTION

The present invention is directed to disubstituted pyrazolobenzodiazepines that inhibit angiogenesis and/or kinase activity. These compounds are useful in the treatment of cancerous tumors, especially breast, colon, lung, and prostate cancer.

BACKGROUND OF THE INVENTION

Angiogenesis is the generation of new blood vessels in a tissue or organ. Under normal physiological conditions, humans and animals undergo angiogenesis only in very specific, restricted situations. For example, angiogenesis is normally observed in wound healing, fetal and embryonal development, and formation of the corpus luteum, endometrium and placenta.

Capillary blood vessels are composed of endothelial cells and pericytes, surrounded by a basement membrane. Angiogenesis begins with the erosion of the basement membrane by enzymes released from endothelial cells and leukocytes. Endothelial cells, lining the lumen of blood vessels, then protrude through the basement membrane. Angiogenic stimulants induce the endothelial cells to migrate through the eroded basement membrane. The migrating cells form a "sprout" off the parent blood vessel where the endothelial cells undergo mitosis and proliferate. The endothelial sprouts merge with each other to form capillary loops, creating a new blood vessel.

Uncontrolled angiogenesis is a hallmark of cancer. In 1971, Dr. Judah Folkman proposed that tumor growth is dependent upon angiogenesis. See, e.g., Folkman, *New England Journal of Medicine,* 285:1182-86 (1971). According to Dr. Folkman, a tumor can only grow to a certain size without the growth of additional blood vessels to nourish the tumor. In its simplest terms, this proposition states: that "once tumor 'take' has occurred, every increase in tumor cell population must be preceded by an increase in new capillaries converging on the tumor." Tumor 'take' is currently understood to indicate a prevascular phase of tumor growth in which a population of tumor cells occupying a few cubic millimeters volume, and not exceeding a few million cells, can survive on existing host microvessels. Expansion of tumor volume beyond this phase requires the induction of new capillary blood vessels. For example, pulmonary micrometastasis in the early prevascular phase in mice would be undetectable except by high power microscopy on histological sections.

As early as 1945, Algire, et al., *J. Nat. Cancer Inst.,* 6:73-85 (1945), showed that the growth rate of tumors implanted in subcutaneous transparent chambers in mice is slow and linear before neovascularization, and rapid and nearly exponential after neovascularization. In 1966, Dr. Folkman reported that tumors grown in isolated perfused organs where blood vessels do not proliferate are limited to 1-2 $mm^3$ but expand rapidly to >1000 times this volume when they are transplanted in mice and become neovascularized. See, e.g, Folkman, et al, *Anals of Surgery,* 164:491-502 (1966).

Tumor growth in avascular cornea proceeds slowly and at a linear rate, but switches to exponential growth after neovascularization. See, eg., Gimbrone, Jr., et al., *J. Nat. Cancer Inst.,* 52:421-27 (1974)). Tumors suspended in the aqueous fluid of the anterior chamber of the rabbit eye remain viable, avascular, and limited in size to <1 $mm^3$. Once they are implanted on the iris vascular bed, they become neovascularized and grow rapidly, reaching 16,000 times their original volume within two weeks. See, eg., Gimbrone, Jr. et al., *J. Exp. Med.,* 136:261-76.

When tumors are implanted on the chick embryo chorioallantoic membrane, they grow slowly during an avascular phase of >72 hours, but do not exceed a mean diameter of 0.93+0.29 mm. Rapid tumor expansion occurs within 24 hours after the onset of neovascularization, and by day 7 the vascularized tumors reach a mean diameter of 8.0+2.5 mm. See, eg., Knighton, *British, J. Cancer,* 35:347-56 (1977)).

Vascular casts of metastasis in the rabbit liver reveal heterogeneity in size of the metastasis, but show a relatively uniform cut-off point for the size at which vascularization is present. Tumors are generally avascular up to 1 mm in diameter, but are neovascularized beyond that diameter. See, eg., Lien, et al., *Surgery,* 68:334-40 (1970).

In transgenic mice which develop carcinomas in the beta cells of the pancreatic eyelets, pre-vascular hyperplastic eyelets are limited in size to <1 mm. At 6-7 weeks of age, 4-10% of the eyelets become neovascularized, and from these eyelets arrive large vascularized tumors of more than 1,000 times the volume of the pre-vascular eyelets. See, eg., Folkman, et al., *Nature,* 339:58-61 (1989).

It has been shown that tumors can be treated by inhibiting angiogenesis rather than inhibiting proliferation of the tumor cells themselves. For example, Kim et al., *Nature,* 362:841044 (1993), show that a specific antibody against VEGF (vascular endothelial growth factor) reduces microvessel density and causes "significant or dramatic" inhibition of growth of three human tumors which rely on VEGF as their sole mediator of angiogenesis (in nude mice). The antibody does not inhibit growth of the tumor cells in vtiro. Further, Hori, et al., *Cancer, Resp.* 51:6180-84 (1991), shows that anti-bFGF monoclonal antibody causes 70% inhibition of growth of a mouse tumor which is dependent upon secretion of bFGF as its only mediator of angiogenesis. The antibody does not inhibit growth of the tumor cells in vitro. Intraperitoneal injection of bFGF has also been shown to enhance growth of a primary tumor and its metastasis by stimulating growth of capillary endothelial cells in the tumor. The tumor cells themselves lack receptors for bFGF and bFGF is not a mitogen for the tumor cells in vitro. See, e.g., Gross, et al., *Proc. Am. Assoc. Cancer Res.,* 31:79 (1990). A specific angiogenesis inhibitor (AGM-1470) inhibits tumor growth and metastasis in vivo, but is much less active in inhibiting tumor cell proliferation in vitro. It inhibits vascular endothelial cell proliferation half-maximally at 4 logs lower concentration than it inhibits tumor cell proliferation. See, eg., Ingber, et al., *Nature,* 48:555-57 (1990).

There is also indirect clinical evidence that tumor growth is angiogenesis dependent. For example, human retinoblastomas that are metastatic to the vitreous develop into avascular spiroids which are restricted to <1 $mm^3$ despite the fact that they are viable and incorporate $^3$H-Thymidine (when removed from an enucleated eye and analyzed in vitro). Carcinoma of the ovary metastasizes to the peritoneal membrane as tiny avascular white seeds (1-3 $mm^3$). These implants rarely grow larger until one or more of them become neovascularized. Intensity of neovascularization in breast cancer (see, e.g., Weidner, et al., *New Eng. J. of Med.,* 324:1-8

(1991); Weidner, et al., *J. Nat. Cancer Inst.*, 84:1875-87 (1992)) and in prostate cancer (Weidner, et al., *Am. J. Pathol.*, 143 (2):401-09 (1993)) correlates highly with risk of future metastasis.

Metastasis from human cutaneous melanoma is rare prior to neovascularization. The onset of neovascularization leads to increased thickness of the lesion and an increased risk of metastasis. See, eg., Srivastava, et al., *Am. J. Pathol.*, 133: 419-23 (1988)). In bladder cancer, the urinary level of an angiogenic protein, bFGF is a more sensitive indicator of status and extensive disease than is cytology. See, e.g., Nguyen, et al., *J. Nat. Cancer, Inst.*, 85:241-42 (1993).

Angiogenesis has been associated with a number of different types of cancer, including solid tumors and blood-borne tumors. Solid tumors with which angiogenesis has been associated include, but are not limited to, rhabdomyosarcomas, retinoblastoma, Ewing's sarcoma, neuroblastoma, and osteosarcoma. Angiogenesis also has been linked with breast cancer, prostate cancer, lung cancer, and colon cancer. Angiogenesis is also associated with blood-borne tumors, such as leukemias, lymphomas, multiple myelomas, and any of various acute or chronic neoplastic diseases of the bone marrow in which unrestrained proliferation of white blood cells occurs, usually accompanied by anemia, impaired blood clotting, and enlargement of the lymph nodes, liver and spleen. It is believed too that angiogenesis plays a role in the abnormalities in the bone marrow that give rise to leukemia and lymphoma tumors and multiple myeloma diseases.

One of the most frequent angiogenic diseases of childhood is the hemangioma. A hemangioma is a tumor composed of newly-formed blood vessels. In most cases the tumors are benign and regress without intervention. In more severe cases, the tumors progress to large cave and infiltrated forms and create clinical complications. Systemic forms of hemangiomas, hemangiomatoses, which have a high mortality rate. Therapy-resistant hemangiomas exist that can not be treated with therapies currently in use.

Thus, it is clear that angiogenesis plays a major role in the metastasis of cancer. If this angiogenic activity could be repressed or eliminated, then the tumor, although present, would not grow. In the disease state, prevention of angiogenesis could overt the damage caused by the invasion of the new micro vascular system. Therapies directed at control of angiogenic processes could lead to the abrogation or mitigation of these diseases.

Several classes of compounds that inhibit angiogenesis are being investigated as therapeutic agents. These are, for example, thalidomide and thalidomide analogs (U.S. Pat. Nos. 6,235,756 (The Children's Medical Center Corporation); 6,420,414 (The Children's Medical Center Corporation); 6,476,052 (Celgene Corporation)); quinolinones (U.S. Pat. No. 6,774,237 (Chiron Corporation)); serine proteases and kallikreins (U.S. Pat. No. 6,544,947 (EntreMed Inc.)); VEGF analogs and antagonists (U.S. Pat. Nos. 6,783,953 (Janssen Pharmaceutica N.V.); 6,777,534 (Children's Medical Center Corporation)); peptides and proteins that bind Angiostatin™ or Endostatin™ (U.S. Pat. No. 6,201,104 (EntreMed Inc.)); cathepsin V-like polypeptides (U.S. Pat. No. 6,783,969 (Nuvelo Inc.)); other antiangiogenic peptides (U.S. Pat. No. 6,774,211 (Abbott Laboratories); 4-anilinoquinazolines (WO 2002/092578, WO 2002/092577, WO 2002/016352, WO 2002/032651, WO 2000/047212 (Astrazeneca)); phthalazines (WO 2004/033042 (Novartis), WO 2003/022282 (Novartis), WO 2002/012227 (Astrazeneca), WO 2001/010859 (Bayer), WO 98/35958 (Novartis)); isothiazoles (WO 99/62890 (Pfizer)); and indolinones (WO 2001/037820, WO 2000/008202, WO 98/50356, WO 96/40116 (Sugen Inc.)).

Several review articles report the use of angiogenesis inhibitors as therapeutic agents. These articles include Mazitschek et al. Current Opinion in Chemical Biology, 8(4): 432-441 (2004); Underiner, et al., Current Medicinal Chemistry, 11(6): 731-745 (2004); Manley, et al., Biochimica et Biophysica Acta, 1697(1-2): 17-27 (2004); Alessi, et al., Biochimica et Biophysica Acta, 1654(1): 39-49 (2004); Tortora, et al., Current Pharmaceutical Design, 10(1): 11-26 (2004).

Uncontrolled cell proliferation is another hallmark of cancer. Cancerous tumor cells typically have some form of damage to the genes that directly or indirectly regulate the cell-division cycle.

Cyclin-dependent kinases (CDKs) are enzymes which are critical to cell cycle control. See,, e.g., Coleman et al., *Annual Reports in Medicinal Chemistry*, 32: 171-179 (1997). These enzymes regulate the transitions between the different phases of the cell cycle, such as the progression from the $G_1$ phase to the S phase (the period of active DNA synthesis), or the progression from the $G_2$ phase to the M phase, in which active mitosis and cell-division occurs. See, e.g., the articles on this subject appearing in *Science*, 274: 1643-1677 (6 Dec. 1996).

CDKs are composed of a catalytic CDK subunit and a regulatory cyclin subunit. The cyclin subunit is the key regulator of CDK activity, with each CDK interacting with a specific subset of cyclins: e.g. cyclin A (CDK1, CDK 2). The different kinase/cyclin pairs regulate progression through specific stages of the cell cycle. See, e.g., Coleman, supra.

Aberrations in the cell cycle control system have been implicated in the uncontrolled growth of cancerous cells. See, e.g., Kamb, *Trends in Genetics*, 11: 136-140 (1995); and Coleman, supra. In addition, changes in the expression of or in the genes encoding CDK's or their regulators have been observed in a number of tumors. See, e.g., Webster, *Exp. Opin. Invest. Drugs*, 7: 865-887 (1998), and references cited therein. Thus, there is an extensive body of literature validating the use of compounds inhibiting CDKs as anti-proliferative therapeutic agents. See, e.g. U.S. Pat. No. 5,621,082; EP 0 666 270 A2; WO 97/16447; and the references cited in Coleman, supra, in particular reference no. 10. Thus, it is desirable to identify chemical inhibitors of CDK kinase activity.

It is particularly desirable to identify small molecule compounds that may be readily synthesized and are effective in inhibiting one or more CDKs or CDK/cyclin complexes, for treating one or more types of tumors.

Several classes of compounds that inhibit cyclin-dependent kinases have been and are being investigated as therapeutic agents. These are, for example, analogs of Flavopiridol (U.S. Pat. No. 5,733,920 (Mitotix); WO 98/1344 (Bristol-Myers Squibb); WO 97/42949 (Bristol-Meyers Squibb)); purine derivatives (WO 98/05335 (CV Therapeutics); WO 97/20842 (CNRS)); acridones and benzothiadiazines (WO 97/49146 A2 (US Dept. of Health and Human Services)); and antisense (U.S. Pat. No. 5,821,234 (Stanford University)). Furthermore, certain N,N-substituted dihydropyrazolobenzodiazepines have been disclosed in an article discussing CNS-acting compounds. See, M. A. Berghot, *Arch. Pharm.* 325:285-289 (1992).

There continues to be a need for easily synthesized, small molecule compounds for the treatment of one or more types of tumors, in particular through regulation of angiogenesis and/or CDKs.

SUMMARY OF THE INVENTION

The present invention is directed to novel 7,8-disubstituted pyrazolobenzodiazepines and pharmaceutically acceptable salts of these compounds. The compounds of the invention are inhibitors of angiogenesis and/or kinases, such as cyclin-dependent kinases (CDKs), in particular CDK2. These compounds and their pharmaceutically acceptable salts, and esters of said compounds, are anti-proliferative agents useful in the treatment or control of cell proliferative disorders, in particular cancer. The invention is also directed to pharmaceutical compositions containing such compounds and to methods for the treatment and/or prevention of cancer, particularly in the treatment or control of solid tumors. The compounds of the invention are especially useful in the treatment or control of breast, colon, lung and prostate tumors. The invention is also directed to novel intermediates useful in the preparation of the 7,8-disubstituted pyrazolobenzodiazepines, such as those of formula IV described below.

In particular, the present invention provides compounds of formula IV

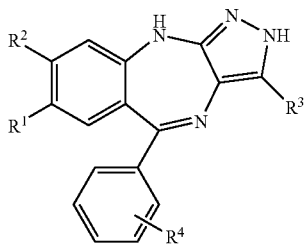

wherein
$R^1$ is alkyl, alkoxy, halogen, COOH, COOAlkyl, CN, C(O)N$(R^6)_2$, or $(OCH_2CH_2)_nOCH_3$;
$R^2$ is alkyl, halogen, alkyl substituted by halogen, OH, alkoxy, alkoxy substituted by halogen, phenyl, $N(R^6)_2$, $(OCH_2CH_2)_nOCH_3$, $O(CH_2)_mNR^7R^8$, or

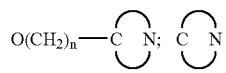

is a 6-membered heterocycle optionally substituted by alkyl or C(O)OR$^6$;
or $R^1$ and $R^2$ together form a 5-membered heterocyclic ring;
$R^3$ is hydrogen or alkyl;
$R^4$ is hydrogen, halogen, CN, NO$_2$, alkyl, or alkoxy;
each $R^6$ is independently hydrogen or alkyl;
$R^7$ and $R^8$ are each independently hydrogen, alkyl, or alkoxyalkyl, or $R^7$ and $R^8$ taken together with the nitrogen atom to which they are attached form a 6-membered heterocycle which is optionally substituted by alkyl;
each n is independently 1, 2, or 3; and
m is 2, 3, or 4;
or a pharmaceutically acceptable salt thereof.

The present invention is further directed to pharmaceutical compositions containing any one or more of the above-described compounds, or a pharmaceutically acceptable salt thereof, and a pharmaceutically acceptable carrier. Methods for preparing such compositions are also part of the invention.

The present invention also is directed to methods of using the compounds of the invention. Compounds of the invention are inhibitors of angiogenesis and/or kinases. Thus the invention is directed to a method of inhibiting angiogenesis. The invention also is directed to a method of inhibiting kinases. Further, the invention is directed to a method for the treatment of cancer, especially breast, colon, lung, and prostate cancers by administering to a patient having cancer, a therapeutically effective amount of a compound of formula IV or a pharmaceutically acceptable salt thereof.

DETAILED DESCRIPTION OF THE INVENTION

In one aspect, the present invention provides 7,8-disubstituted-5-(2-chlorophenyl)-1,2-dihydro-3-methyl-pyrazolo[3,4-b][1,4]benzodiazepines and pharmaceutical compositions containing them. In a second aspect, the present invention provides methods for synthesis of the compounds of the present invention and valuable intermediates for use in such synthesis.

Compounds of the present invention are inhibitors of angiogenesis. Thus, in a third aspect, the present invention provides a method of inhibiting angiogenesis which comprises administering a therapeutically effective amount of a compound of the invention. Compounds of the present invention also are inhibitors of kinases, such as CDK2. Therefore, in a fourth aspect, the invention provides a method of inhibiting kinase activity which comprises administering a therapeutically effective amount of a compound of the invention. In a fifth aspect, the present invention provides a method for the treatment or control of cancer which comprises administering a therapeutically effective amount of a compound of the invention. In particular, the invention provides methods for the treatment of breast, prostate, colon, and lung cancer.

DEFINITIONS

As used herein, the following terms shall have the following definitions. The following definitions used herein apply irrespective of whether the terms in question appear alone or in combination. It must be noted that, as used in the specification and the appended claims, the singular forms "a", "an," and "the" include plural forms unless the context clearly dictates otherwise.

"Alkyl" means a straight-chain or branched, substituted or unsubstituted, saturated aliphatic hydrocarbon having 1 to 6, preferably 1 to 4, carbon atoms. Typical alkyl groups include methyl, ethyl, propyl, isopropyl, butyl, t-butyl, 2-butyl, pentyl, hexyl and the like.

"Alkoxy" means a straight or branched chain hydrocarbonoxy group wherein the "alkyl" portion is a alkyl group as defined above, and the group is attached to the molecule via an oxygen atom. Typical alkoxy groups include methoxy, ethoxy, propyloxy, i-propyloxy, n-butyloxy, 2-butyloxy, tert-butyloxy, n-pentyloxy, n-hexyloxy and the like.

"Halogen" means fluorine, chlorine, bromine or iodine. Preferred halogens are fluorine and chlorine.

"Hetero atom" means an atom selected from N, O and S.

"6-membered Heterocycle" means a 6-membered non-aromatic, partially or completely saturated hydrocarbon group, which contains one to three heteroatoms at least one of which is nitrogen. Examples of 6-membered heterocycles include piperidine, piperazine, morpholine, thiomorpholine, and the like.

"5-membered or 6-membered heterocyclic ring" means a 5- or 6-membered ring containing from one to three heteroatoms. Examples of carbocyclic rings include pentyl and hexyl and the like. Examples of heterocyclic rings include dioxanes, dioxolanes, pyrrolidines, imidazolidines and the like.

"IC$_{50}$" refers to the concentration of a particular pyrazolobenzodiazepine required to inhibit 50% of a specific measured activity. [IC$_{50}$ can be measured, inter alia, as is described in Example A, infra.]

"IC$_{50}$" refers to the concentration of a particular pyrazolobenzodiazepine required to inhibit 90% of a specific measured activity.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts which retain the biological effectiveness and properties of the compounds of formula IV and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide.

"Phenyl" means a functional group that is a benzene ring having one hydrogen removed. Phenyl groups of the present invention may be unsubstituted or substituted, for example, with alkyl, alkoxy, halogen, CN, N(R$^6$)$_2$, NO$_2$, etc.

"Substituted," as in substituted alkyl, means that the substitution can occur at one or more positions and, unless otherwise indicated, that the substituents at each substitution site are independently selected from the specified options.

"Therapeutically Effective Amount" means an amount of at least one compound of Formula IV, or a pharmaceutically acceptable salt, ester, or metabolite thereof, that significantly inhibits proliferation of a tumor cell, including human tumor cell lines or that significantly inhibits angiogenesis of blood vessels supplying the tumor or its metastasis.

The Compounds

The present invention provides compounds of formula IV

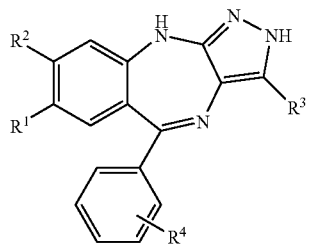

wherein
R$^1$ is alkyl, alkoxy, halogen, COOOH, COOAlkyl, CN, C(O)N(R$^6$)$_2$, or (OCH$_2$CH$_2$)$_n$OCH$_3$;

R$^2$ is alkyl, halogen, alkyl substituted by halogen, OH, alkoxy, alkoxy substituted by halogen, phenyl, N(R$^6$)$_2$, (OCH$_2$CH$_2$)$_n$OCH$_3$, O(CH$_2$)$_m$NR$^7$R$^8$, or

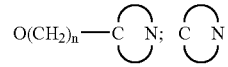

is a 6-membered heterocycle optionally substituted by alkyl or C(O)OR$^6$;
or R$^1$ and R$^2$ together form a 5-membered heterocyclic ring;
R$^3$ is hydrogen or alkyl
R$^4$ is hydrogen, halogen, CN, NO$_2$, alkyl, or alkoxy;
each R$^6$ is independently hydrogen or alkyl;
R$^7$ and R$^8$ are each independently hydrogen, alkyl, or alkoxyalkyl, or R$^7$ and R$^8$ taken together with the nitrogen atom to which they are attached form a 6-membered heterocycle which is optionally substituted by alkyl;
each n is independently 1, 2, or 3; and
m is 2, 3, or 4;
or a pharmaceutically acceptable salt thereof.

In one embodiment, the invention provides compounds of formula IV in which R$^2$ is

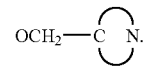

Within this embodiment, preferred compounds include those in which R$^1$ is halogen or cyano.

In another embodiment, the invention provides compounds of formula IV in which R$^2$ is O(CH$_2$)$_m$NR$^7$R$^8$. In such compounds, R$^7$ and R$^8$ can each independently be hydrogen, alkyl, or alkoxyalkyl or R$^7$ and R$^8$ can together with the nitrogen atom to which they are attached form a 6-membered heterocycle. For example, NR$^7$R$^8$ can form a morpholine or piperazine ring. Within this embodiment, preferred compounds are those in which R$^7$ and R$^8$ together with the nitrogen to which they are attached form a 6-membered heterocycle and R$^1$ is halogen or cyano.

Examples of such compounds include
5-(2-chlorophenyl)-1,2-dihydro-7-fluoro-8-(3-(4-morpholinyl)propoxy)-3-methyl-pyrazolo[3,4-b][1,4]benzodiazepine;
7-bromo-5-(2-chlorophenyl)-1,2-dihydro-8-(3-(4-morpholinyl)propoxy)-3-methyl-pyrazolo[3,4-b][1,4]benzodiazepine;
5-(2-chlorophenyl)-7-cyano-1,2-dihydro-8-(3-(4-morpholinyl)propoxy)-3-methyl-pyrazolo[3,4-b][1,4]benzodiazepine; and
5-(2-chlorophenyl)-7-cyano-1,2-dihydro-8-(2-(4-methyl-1-piperazinyl)ethoxy)-3-methyl-pyrazolo[3,4-b][1,4]benzodiazepine.

Also preferred are compounds in which R$^7$ and R$^8$ are each independently hydrogen, alkyl, or alkoxyalkyl and R$^3$ is halogen or cyano. An example of such a compound is 5-(2-chlorophenyl)-7-cyano-1,2-dihydro-8-(2-(2-methoxyethyl)methylamino-ethoxy)-3-methyl-pyrazolo[3,4-b][1,4]benzodiazepine.

In another embodiment, the invention provides compounds of formula IV in which R$^2$ is N(R$^6$)$_2$ where each R$^6$ is independently hydrogen or alkyl. Within this embodiment, compounds in which R$^1$ is either a halogen or cyano group are preferred, for example, the compound 5-(2-chlorophenyl)-1,2-dihydro-7-fluoro-8-N,N-dimethylamino-3-methyl-pyrazolo[3,4-b]benzodiazepine.

In another embodiment, the invention provides compounds of formula IV in which $R^2$ is halogen, alkyl, or alkyl substituted by halogen. Within this embodiment, preferred compounds are those in which $R^1$ is halogen, alkyl or alkoxy. Examples of such compounds include
5-(2-chlorophenyl)-1,2-dihydro-3,7,8-trimethyl-pyrazolo[3,4-b][1,4]benzodiazepine;
8-chloro-5-(2-chlorophenyl)-1,2-dihydro-7-methoxy-3-methyl-pyrazolo[3,4-b][1,4]benzodiazepine;
5-(2-chlorophenyl)-1,2-dihydro-8-fluoro-7-methoxy-3-methyl-pyrazolo[3,4-b][1,4]benzodiazepine;
5-(2-chlorophenyl)-1,2-dihydro-7-methoxy-3-methyl-8-trifluoromethyl-pyrazolo[3,4-b][1,4]benzodiazepine; and
8-chloro-5-(2-chlorophenyl)-1,2-dihydro-3,7-dimethyl-pyrazolo[3,4-b][1,4]benzodiazepine.

In another embodiment, the invention provides compounds of formula IV in which $R^2$ is hydroxy, alkoxy, or alkoxy substituted by halogen. Preferred compounds within this embodiment are those in which $R^1$ is alkyl, cyano, $NH_2C(O)$, or $O(CH_2)_nOCH_3$. Example of such compounds include
5-(2-chlorophenyl)-1,2-dihydro-8-methoxy-7-methoxyethoxy-3-methylpyrazolo[3,4-b][1,4]benzodiazepine;
5-(2-chlorophenyl)-7-cyano-1,2-dihydro-8-methoxy-3-methyl-pyrazolo[3,4-b][1,4]benzodiazepine; and
5-(2-chlorophenyl)-1,2-dihydro-3,7-dimethyl-8-methoxy-pyrazolo[3,4-b][1,4]benzodiazepine.

Other preferred compounds within this group are those in which $R^1$ is halogen. Examples of such compounds include
7-chloro-5-(2-chlorophenyl)-1,2-dihydro-8-methoxy-3-methyl-pyrazolo[3,4-b][1,4]benzodiazepine;
7-bromo-5-(2-chlorophenyl)-1,2-dihydro-8-methoxy-3-methyl-pyrazolo[3,4-b][1,4]benzodiazepine;
5-(2-chlorophenyl)-1,2-dihydro-7-fluoro-8-methoxy-3-methyl-pyrazolo[3,4-b][1,4]benzodiazepine;
5-(2-chlorophenyl)-1,2-dihydro-7-fluoro-8-ethoxy-3-methyl-pyrazolo[3,4-b][1,4]benzodiazepine; and
5-(2-chlorophenyl)-1,2-dihydro-7-fluoro-8-(1-methylethoxy)-3-methyl-pyrazolo[3,4-b][1,4]benzodiazepine.

Further preferred compounds within this group are those in which $R^1$ is alkoxy. Examples of such compounds include
5-(2-chlorophenyl)-1,2-dihydro-7,8-dimethoxy-3-methyl-pyrazolo[3,4-b][1,4]benzodiazepine;
1,2-dihydro-7,8-dimethoxy-5-(2-methoxyphenyl)-3-methyl-pyrazolo[3,4-b][1,4]benzodiazepine;
5-(2-chlorophenyl)-1,2-dihydro-7-methoxy-8-(1-methylethoxy)-3-methyl-pyrazolo[3,4-b][1,4]benzodiazepine; and
5-(2-chlorophenyl)-1,2-dihydro-8-methoxy-7-(1-methylethoxy)-3-methyl-pyrazolo[3,4-b][1,4]benzodiazepine.

In another embodiment, the invention provides compounds of formula IV in which $R^2$ is phenyl. Preferred compounds include those in which $R^1$ is alkoxy, for example, the compound 5-(2-chlorophenyl)-1,2-dihydro-7-methoxy-3-methyl-8-phenyl-pyrazolo[3,4-b][1,4]benzodiazepine.

In another embodiment, the invention provides compounds of formula IV wherein $R^2$ is $(OCH_2CH_2)_nOCH_3$. Preferred compounds within this embodiment are those in which $R^1$ is halogen, alkoxy, or cyano. Examples of such compounds include
5-(2-chlorophenyl)-1,2-dihydro-7-methoxy-8-methoxyethoxy-3-methyl-pyrazolo[3,4-b][1,4]benzodiazepine;
5-(2-chlorophenyl)-1,2-dihydro-7-fluoro-8-methoxyethoxy-3-methyl-pyrazolo[3,4-b][1,4]benzodiazepine;
5-(2-chlorophenyl)-7-cyano-1,2-dihydro-8-methoxyethoxy-3-methyl-pyrazolo[3,4-b][1,4]benzodiazepine; and
5-(2-chlorophenyl)-7-cyano-1,2-dihydro-8-(2-(2-methoxyethoxy)ethoxy)-3-methyl-pyrazolo[3,4-b][1,4]benzodiazepine.

In another embodiment, the invention provides compounds of formula IV wherein $R^1$ and $R^2$ together form an dioxolane ring. An example of such a compound is 5-(2-chlorophenyl)-8,10-dihydro-7-methyl-1,3-dioxolo[4,5-h]pyrazolo[3,4-b][1,4]benzodiazepine.

In another embodiment, the invention provides compounds of formula IV in which $R^1$ is halogen. Within this embodiment, preferred compounds are those in which $R^2$ is halogen; hydroxy; $N(R^6)_2$; $O(CH_2)_mNR^7R^8$, e.g., where $NR^7R^8$ forms a morpholine ring; alkoxy, e.g., methoxy or ethoxy; or

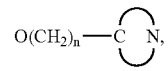

where n is 1 or 2.

In another embodiment, the invention provides compounds of formula IV in which $R^1$ is $(OCH_2CH_2)_nOCH_3$. Within this embodiment, preferred compounds are those in which $R^2$ is alkoxy.

In another embodiment, the invention provides compounds of formula IV in which $R^1$ is $NH_2C(O)$. Within this embodiment, preferred compounds are those in which $R^2$ is alkoxy.

In another embodiment, the invention provides compounds of formula IV in which $R^1$ is alkyl. Within this embodiment, preferred compounds are those in which $R^2$ is alkoxy, halogen, alkyl, or alkyl substituted by halogen.

In another embodiment, the invention provides compounds of formula IV in which $R^1$ is alkoxy. Within this embodiment, preferred compounds are those in which $R^2$ is alkoxy; halogen, e.g., chloro; phenyl; or $(OCH_2CH_2)_nOCH_3$, where n is 1 or 2.

In another embodiment, the invention provides compounds of formula IV in which $R^1$ is cyano. Within this embodiment, preferred compounds are those in which $R^2$ is hydroxy; alkoxy; $O(CH_2)_mNR^7R^8$ in particular where $NR^7R^8$ forms a morpholine ring; $(OCH_2CH_2)_nOCH_3$; or

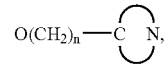

where n is 1 or 2, and m is 2.

In another embodiment, the invention provides compounds of formula IV wherein $R^3$ is hydrogen, i.e. compounds of formula XXII. Examples of such compounds include
5-(2-chlorophenyl)-1,2-dihydro-7-fluoro-8-methoxy-pyrazolo[3,4-b][1,4]benzodiazepine;
5-(2-chlorophenyl)-1,2-dihydro-8-methoxy-7-methyl-pyrazolo[3,4-b][1,4]benzodiazepine; and
5-(2-chlorophenyl)-1,2-dihydro-7-cyano-8-methoxy-pyrazolo[3,4-b][1,4]benzodiazepine.

Synthesis of the Compounds

The present invention provides methods for the synthesis of disubstituted pyrazolobenzodiazepines. Suitable processes for synthesizing compounds of the invention are provided in the examples. Generally, the compound of the invention can be prepared according to the synthesis schemes provided below.

The following synthetic schemes provide two general methods for preparation of compounds of the invention, i.e., compounds of formula IV. In method A, illustrated in schemes 1 and 2, a benzodiazepine of formula I is converted to a compound of formula IV.

form intermediate III, which on reaction with hydrazine forms the pyrazole derivative IV.

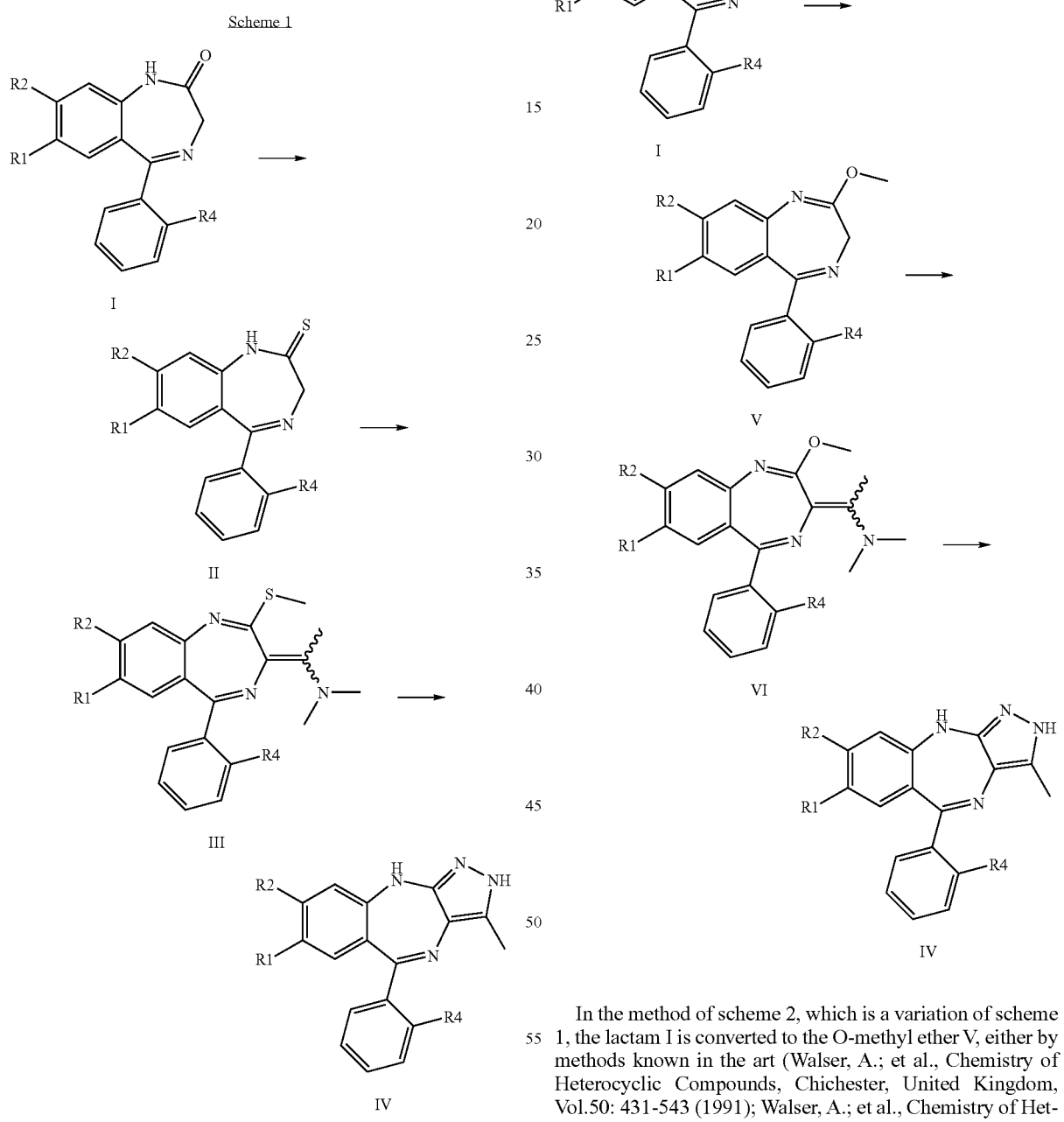

In the method of scheme 1, the lactam I is converted to the corresponding thiolactam II according to procedures known in the art (WO 2000/064900; Scheibye, S., et al., *Bulletin des Societes Chimiques Belges*, 87: 229-38 (1978); Jesberger, M., et al., *Synthesis*, 1929-1958 (2003)). Thiolactam II is reacted with the dimethyl acetal of N,N-dimethyl acetamide, preferably at an elevated temperature, for example, 60 to 130° C., to In the method of scheme 2, which is a variation of scheme 1, the lactam I is converted to the O-methyl ether V, either by methods known in the art (Walser, A.; et al., Chemistry of Heterocyclic Compounds, Chichester, United Kingdom, Vol.50: 431-543 (1991); Walser, A.; et al., Chemistry of Heterocyclic Compounds, Chichester, United Kingdom, vol. 50: 545-629 (1999) Walser, A.; et al., Chemistry of Heterocyclic Compounds, Chichester, United Kingdom, vol 50: 631-848 (1991); Walser, A.; et al., Chemistry of Heterocyclic Compounds, Chichester, United Kingdom, vol 50: 849-946 (1991); Archer, G. A.; et al., Chemical Reviews, 68: 747-84 (1968); Sternbach, L. H., et al., Journal of Organic Chemistry, 27: 3788-96 (1962); U.S. Pat. No. 3,681,341) or by reaction with phosphorous oxychloride followed by reaction with sodium methoxide. Reaction of ether V with the dimethyl acetal of N,N-dimethyl acetamide forms intermediate VI which on reaction with hydrazine forms the pyrazole derivative IV.

Methods for preparing compounds of formula I are well known in the benzodiazepine literature (Walser, A.; et al., Chemistry of Heterocyclic Compounds, Chichester, United Kingdom, vol. 50: 431-543 (1991); Walser, A.; et al., Chemistry of Heterocyclic Compounds, Chichester, United Kingdom, vol. 50: 545-629 (1991); Walser, A.; et al., Chemistry of Heterocyclic Compounds, Chichester, United Kingdom, vol 50: 631-848 (1991); Walser, A.; et al., Chemistry of Heterocyclic Compounds, Chichester, United Kingdom, vol 50: 849-946 (1991); Archer, G. A.; et al., Chemical Reviews, 68: 747-84 (1968); Sternbach, L. H., et al., Journal of Organic Chemistry, 27: 3788-96 (1962)).

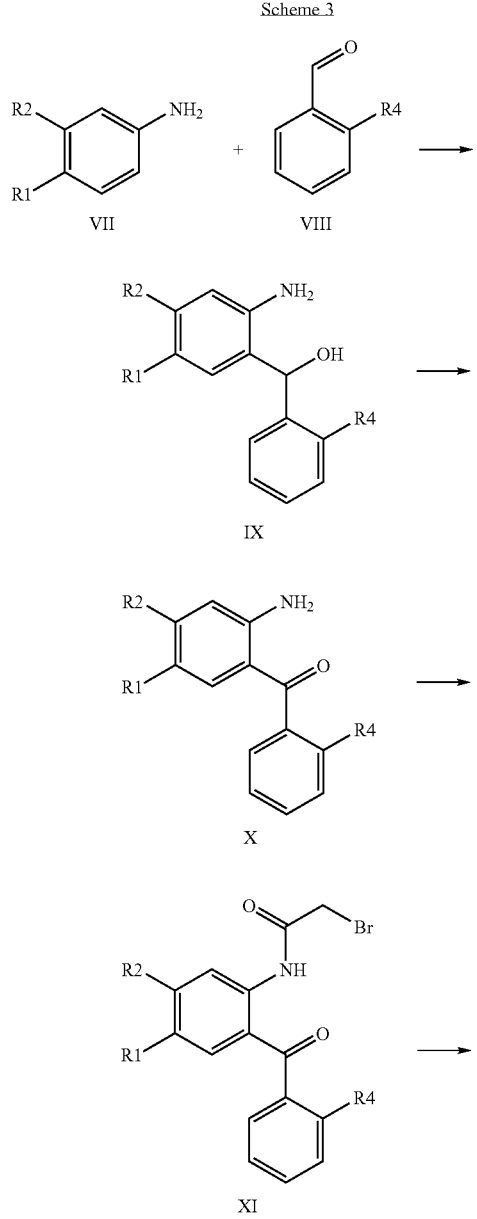

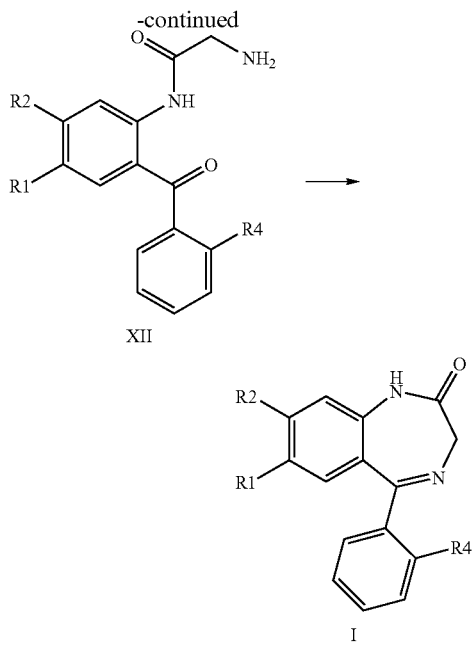

For examples of compounds of formula I where the substitution pattern has not been described previously, the preparation follows the method outlined in scheme 3, where the condensation of an aniline derivative VII with an aldehyde VIII in the presence of a Lewis acid according to the method described in Toyoda, T., et al., *Tetrahedron Letters*, 21: 173-6 (1980), generates an aminoalcohol IX.

Compounds of formula VIII are commercially available. Compounds of formula VIII are commercially available, or are known compounds prepared from commercially available materials by procedures known in the art. Compounds of formula VII, with the exception of VIIgg, VIIkk, VIIii, and VIIjj, are commercially available. Compounds of formula VIIgg and VIIkk can be prepared, for example, by the method of FR1573745. Compounds VIIii and VIIjj can be prepared by the following method, which is described in terms of VIIii. A mixture of 7.34 g (0.0347 mol) of 1-methoxy-4-nitro-2-isopropoxybenzene and 15 g of Raney-Nickel in 80 mL of tetrahydrofuran-ethanol (1:1) was shaken vigorously under a 50 psi atmosphere of hydrogen for 4 hours. The mixture was then filtered through Celite and concentrated under reduced pressure to giver 4.57 g of 3-methoxy-4-isopropoxyaniline, which was used directly for the next step. VIIjj can be prepared in a similar manner from 2-methoxy-4-nitro-1-isopropoxybenzene which can be prepared from commercially available materials using the procedure of Castello et al., *Tetrahedron Letters*, 26: 2489-92 (1985).

Oxidation of IX to the corresponding amino ketone X can be accomplished by methods known in the art (see, e.g., the Walser references described above; Sugasawa, T.; et al., Journal of Heterocyclic Chemistry, 16(3): 445-8 (1979); and Leroux, F., et al., Journal of Organic Chemistry, 68: 4693-4699 (2003)). Derivatization of X with a glycine equivalent is accomplished by reaction of X with bromoacetyl bromide followed by reaction either with ammonia to provide XII or by reaction with sodium azide followed by azide to amine reduction to provide XII, which then undergoes cyclization to lactam I (see, e.g., Walser references described above).

Scheme 4

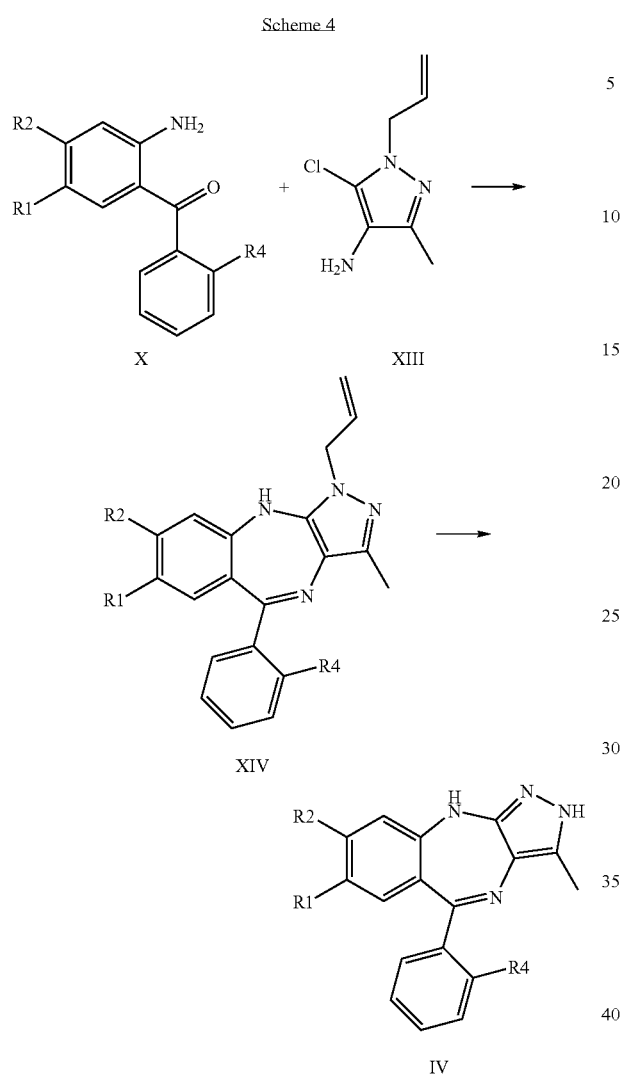

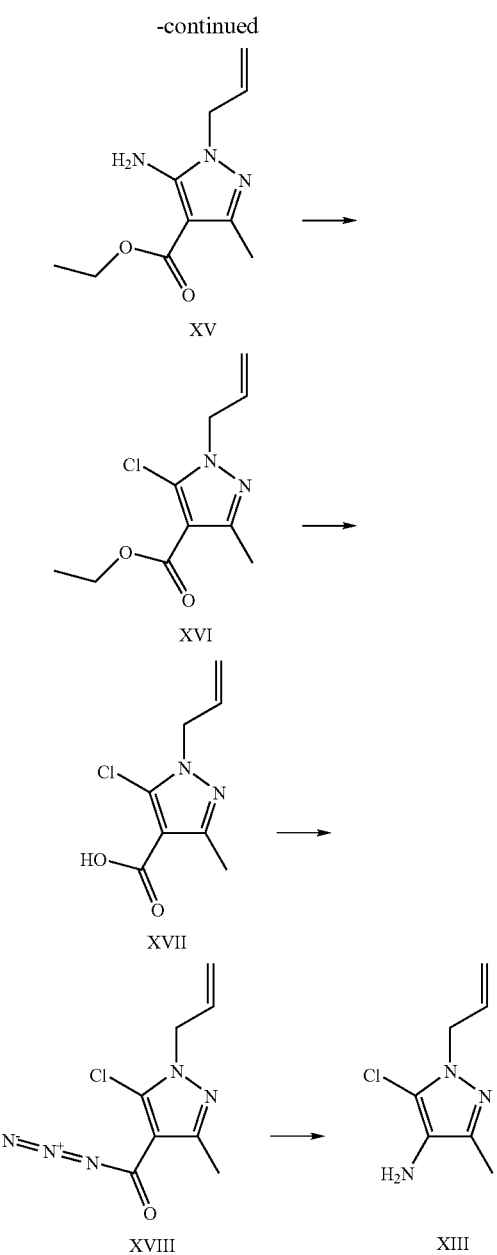

Alternatively, the pyrazole derivatives of formula IV may be formed by method B outlined in scheme 4. Intermediate X is reacted with amino-chloro-pyrazole derivative XIII to form intermediate XIV. Removal of the allyl group from XIV is accomplished by the general method described in Taniguchi, T., et al., *Tetrahedron Letters*, 39: 4679-4682 (1998), wherein intermediate XIV is reacted in the presence of diisobutylaluminum hydride and a nickel catalyst to generate the pyrazole derivative IV.

The amino-chloro-pyrazole derivative XIII is prepared by the methods outlined in scheme 5 and scheme 6.

Scheme 5

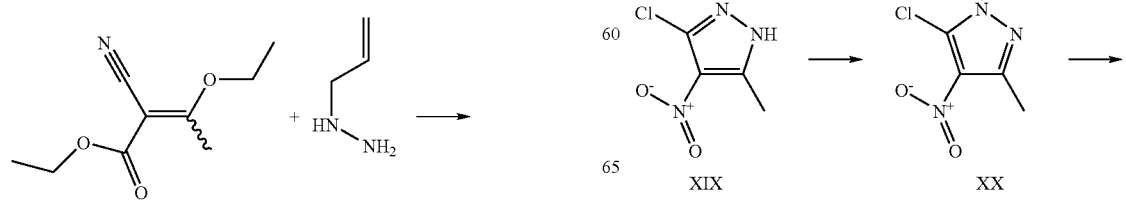

-continued

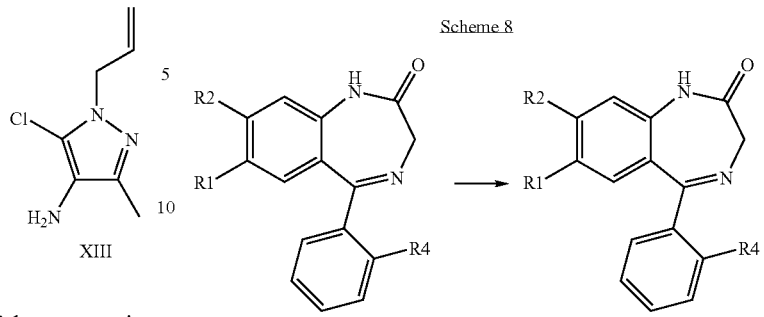

XIII

In scheme 5, ethyl-2-cyano-3-ethoxy-2-butenoate is reacted with 2-propenyl-hydrazine to form pyrazole intermediate XV. Ethyl-2-cyano-3-ethoxy-2-butenoate can be prepared from commercially available materials via the method described in U.S. Pat. No. 2,824,121. The amino ester XV is converted to the corresponding chloro derivative XVI by diazotization and reaction with chloride in the presence of copper salts. Hydrolysis of the ester under basic conditions provides the pyrazole acid intermediate XVII. The acid XVII is reacted with methyl chloroformate followed by azide to form the intermediate carbonyl azide pyrazole XVIII, which on heating, followed by workup provides the amino-chloro-pyrazole derivative XIII. Alternatively, amino-chloro-pyrazole derivative XIII may be prepared by allylation of nitropyrazole XIX (forming XX), followed by reduction of the nitro group to amino (scheme 6).

Additional substitutions for R¹ and R² can be obtained when either R¹ or R² is a functional group that can undergo further transformation. For example in cases where R¹ and R² are fluorine, monosubstitution is possible by reaction with an alcohol or amine in the presence of a base. These reactions are illustrated in schemes 7, 8 and 9.

Scheme 7

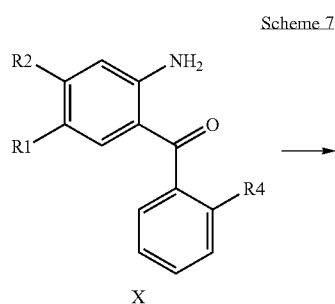

X

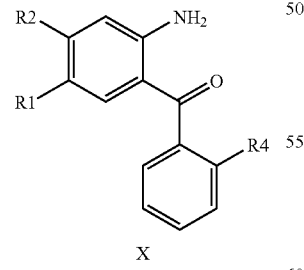

X

This reaction can be used to convert compounds such as (2-amino-4,5-difluorophenyl)-(2-chlorophenyl)-methanone (Xmm) to compounds such as (2-amino-5-fluoro-4-methoxyphenyl)-(2-chlorophenyl)-methanone (Xa) and (2-amino-5-fluoro-4-(3-(4-morpholinyl)propoxy)phenyl)-(2-chlorophenyl)-methanone (Xi).

Scheme 8

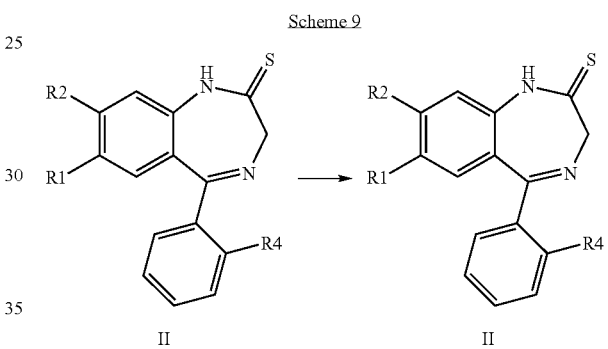

This reaction can be used to convert compounds such as 5-(2-chlorophenyl)-7,8-difluoro-1,3-dihydro-2H-1,4-benzodiazepin-2-one (1 mm) to compounds such as 5-(2-chlorophenyl)-1,3-dihydro-7-fluoro-8-methoxy-2H-1,4-benzodiazepin-2-one (Ia) and 5-(2-chlorophenyl)-7-cyano-1,3-dihydro-8-methoxy-2H-1,4-benzodiazepin-2-one (Ib).

Scheme 9

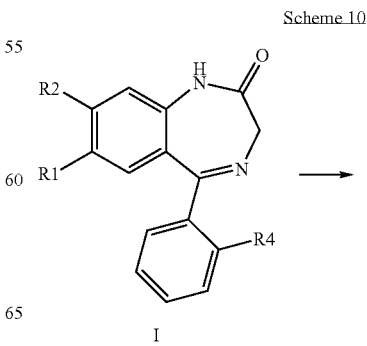

This reaction can be used to convert compounds such as 5-(2-chlorophenyl)-1,3-dihydro-7,8-difluoro-2H-1,4-benzodiazepin-2-thione (IImm) to compounds such as 5-(2-chlorophenyl)-1,3-dihydro-7-fluoro-8-methoxy-2H-1,4-benzodiazepin-2-thione (IIa), 5-(2-chlorophenyl)-1,3-dihydro-7-fluoro-8-methoxyethoxy-2H-1,4-benzodiazepin-2-thione (IIf), 5-(2-chlorophenyl)-1,3-dihydro-8-ethoxy-7-fluoro-2H-1,4-benzodiazepin-2-thione (IIg), and 5-(2-chlorophenyl)-1,3-dihydro-7-fluoro-8-(1-methylethoxy)-2H-1,4-benzodiazepin-2-thione (IIh).

In examples where R² is a methoxy group, the intermediate can be demethylated to the corresponding hydroxy derivative, which can then be further alkylated. This is outlined in scheme 10.

Scheme 10

-continued

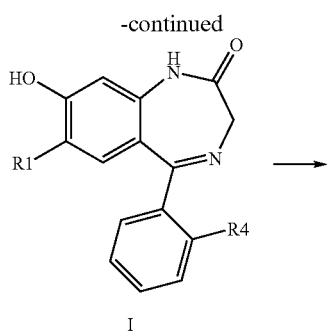

I

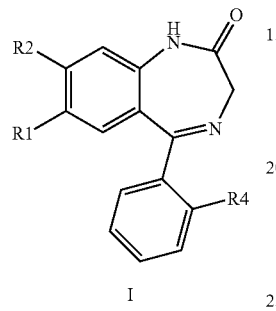

I

This reaction can be used, for example, to convert compounds such as 7-bromo-5-(2-chlorophenyl)-1,3-dihydro-8-methoxy-2H-1,4-benzodiazepin-2-one (Id) to compounds such as 7-bromo-5-(2-chlorophenyl)-1,3-dihydro-8-(3-(4-morpholinyl)propoxy)-2H-1,4-benzodiazepin-2-one (Ij), 7-bromo-5-(2-chlorophenyl)-1,3-dihydro-8-methoxy-ethoxy-2H-1,4-benzodiazepin-2-one (Inn), 7-bromo-5-(2-chlorophenyl)-1,3-dihydro-8-(2-(2-methoxyethoxy)ethoxy)-2H-1-4-benzodiazepin-2-one (Ioo), and 7-bromo-5-(2-chlorophenyl)-1,3-dihydro-8-hydroxy-2H-1,4-benzodiazepin-2-one (Ipp). This reaction also can be used to convert a compound of formula 5-(2-chlorophenyl)-7-cyano-1,3-dihydro-8-methoxy-2H-1,4-benzodiazepin-2-one (Ib) to compounds such as 5-(2-chlorophenyl)-7-cyano-1,3-dihydro-8-(3-(4-morpholinyl)propoxy)-2H-1,4-benzodiazepin-2-one (Ik), 5-(2-chlorophenyl)-7-cyano-1,3-dihydro-8-(2-((2-methoxyethyl)methylamino)-ethoxy)-2H-1,4-benzodiazepin-2-one (Iv) 5-(2-chlorophenyl)-7-cyano-1,3-dihydro-8-hydroxy-2H-1,4-benzodiazepin-2-one (Iqq), 5-(2-chlorophenyl)-7-cyano-1,3-dihydro-8-(1-t-butoxycarbonyl-4-piperidinyl)methoxy-2H-1,4-benzodiazepin-2-one (Irr) and 8-(2-chloroethoxy)-5-(2-chlorophenyl)-7-cyano-1,3-dihydro-2H-1,4-benzodiazepin-2-one (Iss).

Compounds of formula IV in which R1 are CN or C(O)N(R6)2 can be converted to compounds in which R1 is COOH or COOAlkyl via methods known in the art, for example, those described in U.S. Pat. No. 6,440,959.

For those compounds of formula IV where $R^3$ is H (Compounds of formula XXII), the compounds can be prepared according to the general method outlined in Scheme 11.

Scheme 11

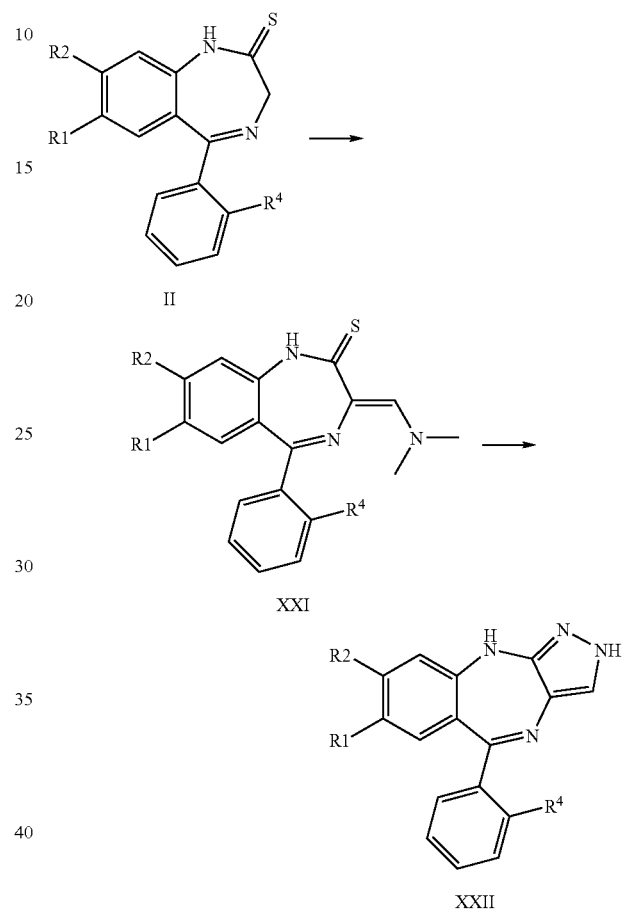

XXII

This process has been previously described for examples where $R^2$ is H in commonly owned U.S. Pat. No. 6,440,959. Thiolactam II is reacted with dimethylformamide diethyl acetal to produce intermediate XXI, which is then treated with hydrazine to yield the pyrazolobenzodiazepine XXII. Specific examples of this reaction can be found in Examples 90 to 92, below.

SUBSTITUTION TABLE

| | $R^1$ | $R^2$ | $R^3$ | $R^4$ |
|---|---|---|---|---|
| a | F | OCH$_3$ | CH$_3$ | Cl |
| b | CN | OCH$_3$ | CH$_3$ | Cl |
| c | H$_2$NCO | OCH$_3$ | CH$_3$ | Cl |
| d | Br | OCH$_3$ | CH$_3$ | Cl |
| e | CH$_3$ | OCH$_3$ | CH$_3$ | H |
| f | F | OCH$_2$CH$_2$OCH$_3$ | CH$_3$ | Cl |
| g | F | OCH$_2$CH$_3$ | CH$_3$ | Cl |
| h | F | OCH(CH$_3$)$_2$ | CH$_3$ | Cl |
| i | F | OCH$_2$CH$_2$CH$_2$N(CH$_2$CH$_2$)$_2$O | CH$_3$ | Cl |
| j | Br | OCH$_2$CH$_2$CH$_2$N(CH$_2$CH$_2$)$_2$O | CH$_3$ | Cl |

-continued

SUBSTITUTION TABLE

|  | $R^1$ | $R^2$ | $R^3$ | $R^4$ |
|---|---|---|---|---|
| k | CN | $OCH_2CH_2CH_2N(CH_2CH_2)_2O$ | $CH_3$ | Cl |
| l | F | $N(CH_3)_2$ | $CH_3$ | Cl |
| m | CN | $OCH_2CH_2OCH_3$ | $CH_3$ | Cl |
| n | CN | $OCH_2CH_2OCH_2CH_2OCH_3$ | $CH_3$ | Cl |
| o | F | $OCH_2CH(CH_2CH_2)_2NCH_3$ | $CH_3$ | Cl |
| p | CN | $OCH_2CH(CH_2CH_2)_2NCH_3$ | $CH_3$ | Cl |
| q | F | $OCH_2CH_2N(CH_2CH_2)_2O$ | $CH_3$ | Cl |
| r | CN | $OCH_2CH_2N(CH_2CH_2)_2O$ | $CH_3$ | Cl |
| s | F | $OCH_2CH_2N(CH_2CH_2)_2NCH_3$ | $CH_3$ | Cl |
| t | CN | $OCH_2CH_2N(CH_2CH_2)_2NCH_3$ | $CH_3$ | Cl |
| u | F | $OCH_2CH_2N(CH_3)CH_2CH_2OCH_3$ | $CH_3$ | Cl |
| v | CN | $OCH_2CH_2N(CH_3)CH_2CH2OCH_3$ | $CH_3$ | Cl |
| w | $CH_3$ | CH3 | $CH_3$ | Cl |
| x | $OCH_3$ | $OCH_3$ | $CH_3$ | Cl |
| y | $OCH_3$ | Cl | $CH_3$ | Cl |
| z | $CH_3$ | $OCH_3$ | $CH_3$ | Cl |
| aa | $OCH_3$ | $OCH_3$ | $CH_3$ | $OCH_3$ |
| bb |  | —$OCH_2O$— | $CH_3$ | Cl |
| cc | Cl | $OCH_3$ | $CH_3$ | Cl |
| dd | $OCH_3$ | F | $CH_3$ | Cl |
| ee | $OCH_3$ | $CF_3$ | $CH_3$ | Cl |
| ff | $OCH_3$ | Ph | $CH_3$ | Cl |
| gg | $OCH_3$ | $OCH_2CH_2OCH_3$ | $CH_3$ | Cl |
| hh | $CH_3$ | Cl | $CH_3$ | Cl |
| ii | $OCH_3$ | $OCH(CH_3)_2$ | $CH_3$ | Cl |
| jj | $OCH(CH_3)_2$ | $OCH_3$ | $CH_3$ | Cl |
| kk | $OCH_2CH_2OCH_3$ | $OCH_3$ | $CH_3$ | Cl |
| mm | F | F | $CH_3$ | Cl |
| nn | Br | $OCH_2CH_2OCH_3$ | $CH_3$ | Cl |
| oo | Br | $OCH_2CH_2OCH_2CH_2OCH_3$ | $CH_3$ | Cl |
| pp | Br | OH | $CH_3$ | Cl |
| qq | CN | OH | $CH_3$ | Cl |
| rr | CN | $OCH_2CH(CH_2CH_2)_2NCOOC(CH_3)_3$ | $CH_3$ | Cl |
| ss | CN | $OCH_2CH_2Cl$ | $CH_3$ | Cl |

Intermediates

Compounds of formula XIV

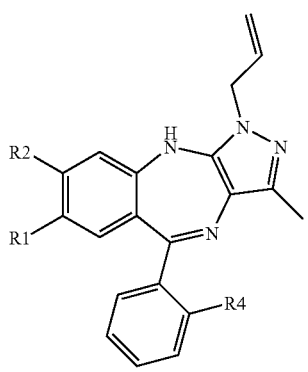

XIV wherein
$R^1$ is alkyl, alkoxy, halogen, COOH, COOAlkyl, CN, C(O)N($R^6$)$_2$, or $(OCH_2CH_2)_nOCH_3$;
$R^2$ is alkyl, halogen, alkyl substituted by halogen, OH, alkoxy, alkoxy substituted by halogen, phenyl, N($R^6$)$_2$, $(OCH_2CH_2)_nOCH_3$, $O(CH_2)_mNR^7R^8$ or

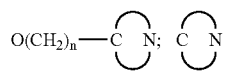

is a 6-membered heterocycle optionally substituted by alkyl or C(O)O$R^6$;

or $R^1$ and $R^2$ together form a 5-membered heterocyclic ring;
$R^4$ is hydrogen, halogen, CN, $NO_2$, alkyl, or alkoxy;
each $R^6$ is independently hydrogen or alkyl;
$R^7$ and $R^8$ are each independently hydrogen, alkyl, or alkoxyalkyl, or $R^7$ and $R^8$ taken together with the nitrogen atom to which they are attached form a 6-membered heterocycle which is optionally substituted by alkyl;
each n is independently 1, 2, or 3; and
m is 2, 3, or 4 are novel compounds useful as intermediates in the preparation of compounds of formula IV. In one embodiment, the present invention provides compounds of formula XIV. In another embodiment, the present invention provides the following specific compounds of formula XIV:

5-(2-chlorophenyl)-1,2-dihydro-3,7,8-trimethyl-1-(2-propenyl)-pyrazolo[3,4-b][1,4]benzodiazepine;

5-(2-chlorophenyl)-1,2-dihydro-7-fluoro-8-methoxy-3-methyl-1-(2-propenyl)-pyrazolo[3,4-b][1,4]benzodiazepine;

5-(2-chlorophenyl)-1,2-dihydro-7,8-dimethoxy-3-methyl-1-(2-propenyl)-pyrazolo[3,4-b][1,4]benzodiazepine;

8-chloro-5-(2-chlorophenyl)-1,2-dihydro-7-methoxy-3-methyl-1-(2-propenyl)-pyrazolo[3,4-b][1,4]benzodiazepine;

5-(2-chlorophenyl)-1,2-dihydro-8-methoxy-3,7-dimethyl-1-(2-propenyl)-pyrazolo[3,4-b][1,4]benzodiazepine;

1,2-dihydro-7,8-dimethoxy-5-(2-methoxyphenyl)-3-methyl-1-(2-propenyl)-pyrazolo[3,4-b][1,4]benzodiazepine;

5-(2-chlorophenyl)-8,10-dihydro-7-methyl-1,3-dioxolo[4,5-h]pyrazolo[3,4-b][1,4]benzodiazepine;

7-chloro-5-(2-chlorophenyl)-1,2-dihydro-8-methoxy-3-methyl-1-(2-propenyl)-pyrazolo[3,4-b][1,4]benzodiazepine;

5-(2-chlorophenyl)-1,2-dihydro-8-fluoro-7-methoxy-3-methyl-1-(2-propenyl)-pyrazolo[3,4-b][1,4]benzodiazepine;

5-(2-chlorophenyl)-1,2-dihydro-7-methoxy-3-methyl-1-(2-propenyl)-8-trifluoromethyl-pyrazolo[3,4-b][1,4]benzodiazepine;

5-(2-chlorophenyl)-1,2-dihydro-7-methoxy-3-methyl-8-phenyl-1-(2-propenyl)-pyrazolo[3,4-b][1,4]benzodiazepine;

5-(2-chlorophenyl)-1,2-dihydro-7-methoxy-8-methoxyethoxy-3-methyl-1-(2-propenyl)-pyrazolo[3,4-b][1,4]benzodiazepine;

8-chloro-5-(2-chlorophenyl)-1,2-dihydro-3,7-dimethyl-1-(2-propenyl)-pyrazolo[3,4-b][1,4]benzodiazepine;

5-(2-chlorophenyl)-1,2-dihydro-7-methoxy-8-(1-methylethoxy)-3-methyl-1-(2-propenyl)-pyrazolo[3,4-b][1,4]benzodiazepine;

5-(2-chlorophenyl)-1,2-dihydro-8-methoxy-7-(1-methylethoxy)-3-methyl-1-(2-propenyl)-pyrazolo[3,4-b][1,4]benzodiazepine; and 5-(2-chlorophenyl)-1,2-dihydro-8-methoxy-7-methoxyethoxy-3-methyl-1-(2-propenyl)-pyrazolo[3,4-b][1,4]benzodiazepine.

Compositions/Formulations

The present invention provides pharmaceutical compositions which comprise at least one compound of the present invention, e.g., a compound of formula IV, or a pharmaceutically acceptable salt thereof and a pharmaceutically acceptable carrier.

The pharmaceutical compositions of the invention can be administered orally, for example, in the form of tablets, coated tablets, dragees, hard or soft gelatin capsules, solutions, emulsions or suspensions. The compositions also can be administered rectally, for example, in the form of suppositories, or parenterally, for example, in the form of injectable solutions.

The pharmaceutical compositions of the present invention comprise one or more compounds of formula IV and/or pharmaceutically acceptable salts thereof. Such compositions can be manufactured in a manner that is known in the art, for example, by means of conventional mixing, encapsulating, dissolving, granulating, emulsifying, entrapping, dragee-making, or lyophilizing processes. These pharmaceutical compositions can be formulated with therapeutically inert inorganic or organic carriers. Lactose, corn starch or derivatives thereof, talc, steric acid or its salts can be used as such carriers for tablets, coated tablets, dragees, and hard gelatin capsules. Suitable carriers for soft gelatin capsules include vegetable oils, waxes and fats. Depending on the nature of the active substance, no carriers are generally required in the case of soft gelatin capsuls. Suitable carriers for the manufacture of solutions and syrups are water, polyols, saccharose, invert sugar and glucose. Suitable carriers for injection are water, alcohols, polyols, glycerine, vegetable oils, phospholipids, and surfactants. Suitable carriers for suppositories are natural or hardened oils, waxes, fats, and semi-liquid polyols.

The pharmaceutical compositions can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They also can contain other therapeutically valuable substances, including additional active ingredients other than those of formula IV.

Dosages

As mentioned above, the compounds of formula IV and their pharmaceutically acceptable salts and compositions containing these compounds are useful in the treatment or control of cell proliferative disorders, in particular oncological disorders. These compounds and formulations containing said compounds are particularly useful in the treatment or control of solid tumors, such as, for example, breast, prostate, lung, and colon tumors.

A therapeutically effective amount or dosage of a compound of formula IV can vary within wide limits and will be adjusted to the individual requirements in each particular case. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

EXAMPLES

General: In the examples temperatures are indicated in degrees C. For mass spectral data, values are given as the MH+/Z ion obtained in the positive mode, electrospray measured on a Micromass Platform II mass spectrometer.

Where an example is said to be performed in a manner analogous to another example, all of the conditions are the same as those specified in the original example except that in some cases different amounts of the materials were employed. Where a different amount of starting material is provided, the other ingredients employed in the example were used in an amount having the same proportion to the starting material as in the original example.

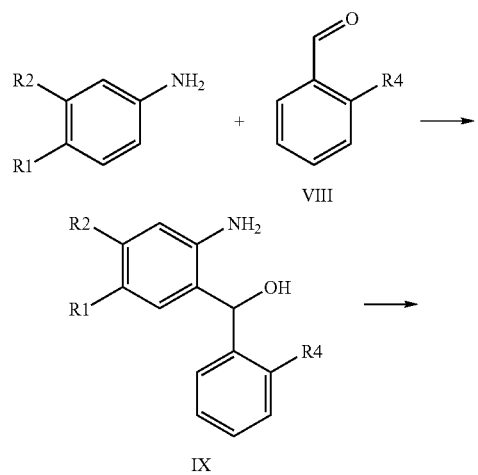

Preparation of aminobenzophenone intermediates X (scheme 3)

-continued

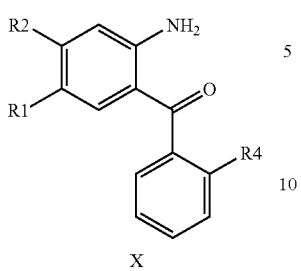

X

Example 1

Preparation of (2-amino-5-fluoro-4-methoxyphenyl)-(2-chlorophenyl)-methanone (Xa)

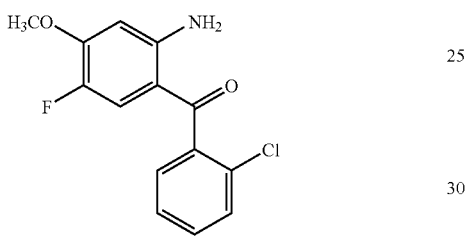

A solution of 2.0 g (0.0142 mole) of 4-fluoro-3-methoxyaniline in 20 mL of dichloromethane was added dropwise to 2.24 g (0.0142 mole) of dichlorophenylborane in 20 mL of dichloromethane at −20 to −30° C., followed by the addition of 3.59 g (0.0355 mole) of triethylamine in 10 mL of dichloromethane. The mixture was stirred for 30 minutes; then, 2.0 g (0.0142 mole) of 2-chlorobenzaldehyde in 30 mL of dichloromethane was added. The cooling bath was removed and the mixture stirred at room temperature for 4 hours. With rapid stirring, 100 mL of cold water was added to the reaction mixture, followed by 150 mL of brine. The dichloromethane layer was separated, dried over anhydrous sodium sulfate, filtered and concentrated under reduced pressure. The residue (4.5 g as a brown oil) was stirred at room temperature for 1 hour with 10 mL of diethyl ether and 30 mL of 2 M sodium hydroxide. The reaction mixture was extracted with ethyl acetate, and the ethyl acetate layer dried over anhydrous sodium sulfate, filtered, and concentrated under reduced pressure to give 3.6 g of the corresponding aminoalcohol IXa ($R^1$=F, $R^2$=OCH$_3$, $R^4$=Cl), which was used directly in the next step.

The aminoalcohol (3.6 g) obtained in the previous reaction was dissolved in 60 of dichloromethane and stirred with 6.09 g (0.071 mole) of manganese dioxide. After four hours, the mixture was filtered and concentrated under reduced pressure to give 4.2 g of the crude ketone (2-amino-5-fluoro-4-methoxyphenyl)-(2-chlorophenyl)-methanone (Xa) as a brown oil. The crude ketone was purified by silica gel chromatography, eluting with ethyl acetate-hexanes to give 2.03 g of (2-amino-5-fluoro-4-methoxyphenyl)-(2-chlorophenyl)-methanone (Xa).

MH+/Z=280.

Example 2

Preparation of (2-amino-5-bromo-4-methoxyphenyl)-(2-chlorophenyl)-methanone (Xd)

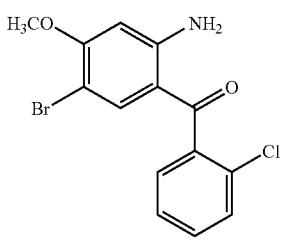

(2-amino-5-bromo-4-methoxyphenyl)-(2-chlorophenyl)-methanone (Xd) was prepared by reacting 2-chlorobenzaldehyde with 0.086 moles of 4-bromo-3-methoxy aniline in a manner analogous to Example 1. MH+/Z=340.

Example 3

Preparation of (2-amino-4,5-dimethylphenyl)-(2-chlorophenyl)-methanone (Xw)

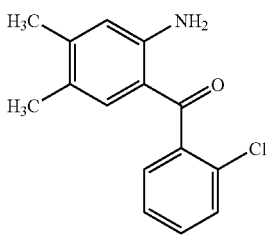

(2-amino-4,5-dimethylphenyl)-(2-chlorophenyl)-methanone (Xw) was prepared by reacting 2-chlorobenzaldehyde with 0.123 moles of 3,4-dimethyl aniline in a manner analogous to Example 1.

Example 4

Preparation of (2-amino-4,5-dimethoxyphenyl)-(2-chlorophenyl)-methanone (Xx)

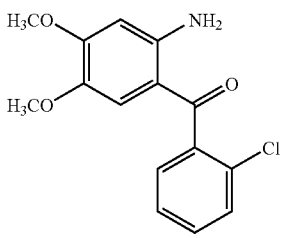

(2-amino-4,5-dimethoxyphenyl)-(2-chlorophenyl)-methanone (Xx) was prepared by reacting 2-chlorobenzaldehyde with 0.0196 moles of 3,4-dimethoxy aniline in a manner analogous to Example 1. MH+/Z=292.

Example 5

Preparation of (2-amino-4-chloro-5-methoxyphenyl)-(2-chlorophenyl)-methanone (Xy)

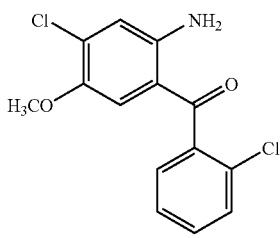

(2-amino-4-chloro-5-methoxyphenyl)-(2-chlorophenyl)-methanone (Xy) was prepared by reacting 2-chlorobenzaldehyde with 0.019 moles of 3-chloro-4-methoxy aniline in a manner analogous to Example 1. MH+/Z=296.

Example 6

Preparation of (2-amino-4-methoxy-5-methylphenyl)-(2-chlorophenyl)-methanone (Xz)

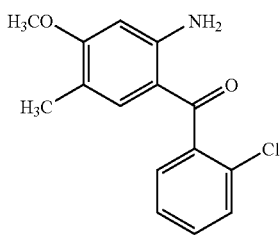

(2-amino-4-methoxy-5-methylphenyl)-(2-chlorophenyl)-methanone (Xz) was prepared by reacting 2-chlorobenzaldehyde with 0.0226 moles of 3-methoxy-4-methyl aniline in a manner analogous to Example 1. MH+/Z=276.

Example 7

Preparation of (2-amino-4,5-dimethoxyphenyl)-(2-methoxyphenyl)-methanone (Xaa)

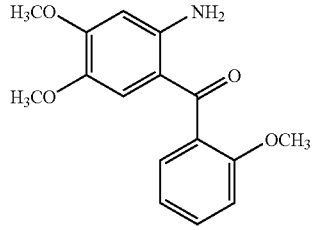

(2-amino-4,5-dimethoxyphenyl)-(2-methoxyphenyl)-methanone (Xaa) was prepared by reacting 2-methoxybenzaldehyde with 0.0196 moles of 3,4-dimethoxy aniline in a manner analogous to Example 1. MH+/Z=288.

Example 8

Preparation of (6-amino-1,3-benzodioxol-5-yl)-(2-chlorophenyl)-methanone (Xbb)

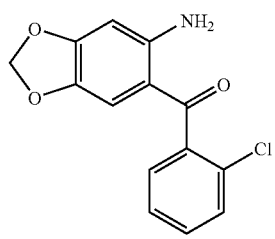

(6-amino-1,3-benzodioxol-5-yl)-(2-chlorophenyl)-methanone (Xbb) was prepared by reacting 2-chlorobenzaldehyde with 0.020 moles of 3,4-methylendioxy aniline in a manner analogous to Example 1. MH+/Z=276.

Example 9

Preparation of (2-amino-5-chloro-4-methoxy-phenyl)-(2-chlorophenyl)-methanone (Xcc)

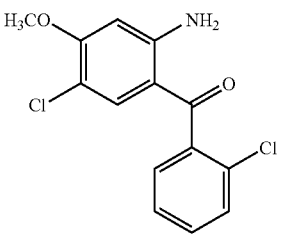

(2-amino-5-chloro-4-methoxyphenyl)-(2-chlorophenyl)-methanone (Xcc) was prepared by reacting 2-chlorobenzaldehyde with 0.019 moles of 3-methoxy-4-chloro aniline in a manner analogous to Example 1. MH+/Z=296.

Example 10

Preparation of (2-amino-4-fluoro-5-methoxyphenyl)-(2-chlorophenyl)-methanone (Xdd)

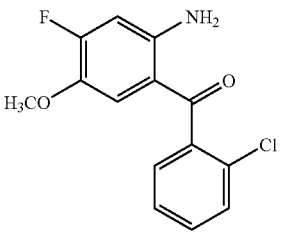

(2-amino-4-fluoro-5-methoxyphenyl)-(2-chlorophenyl)-methanone (Xdd) was prepared by reacting 2-chlorobenzaldehyde with 0.0223 moles of 3-fluoro-4-methoxy aniline in a manner analogous to Example 1. MH+/Z=280.

Example 11

Preparation of (2-amino-5-methoxy-4-trifluoromethylphenyl)-(2-chlorophenyl)-methanone (Xee)

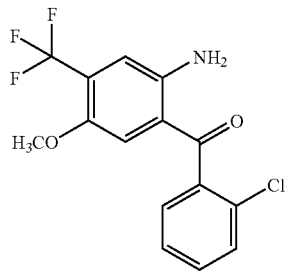

(2-amino-5-methoxy-4-trifluoromethylphenyl)-(2-chlorophenyl)-methanone (Xee) was prepared by reacting 2-chlorobenzaldehyde with 0.0263 moles of 4-methoxy-3-trifluoromethyl aniline in a manner analogous to Example 1. MH+/Z=330.

Example 12

Preparation of (2-amino-5-methoxy-4-phenylphenyl)-(2-chlorophenyl)-methanone (Xff)

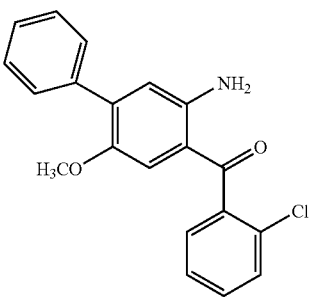

(2-amino-5-methoxy-4-phenylphenyl)-(2-chlorophenyl)-methanone (Xff) was prepared by reacting 2-chlorobenzaldehyde with 0.0226 moles of 4-methoxy-3-phenyl aniline in a manner analogous to the Example 1. MH+/Z=338.

Example 13

Preparation of (2-amino-5-methoxy-4-(2-methoxyethoxy)phenyl)-(2-chlorophenyl)-methanone

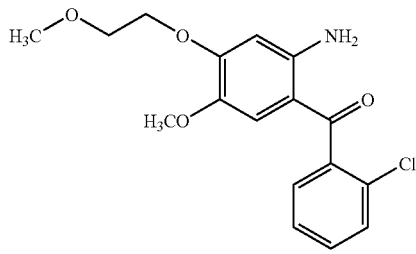

(2-amino-5-methoxy-4-(2-methoxyethoxy)phenyl)-(2-chlorophenyl)-methanone (Xgg) was prepared by reacting 2-chlorobenzaldehyde with 0.0296 moles of 4-methoxy-3-(2-methoxyethoxy) aniline in a manner analogous to Example 1. MH+/Z=336.

Example 14

Preparation of (2-amino-4-chloro-5-methylphenyl)-(2-chlorophenyl)-methanone (Xhh)

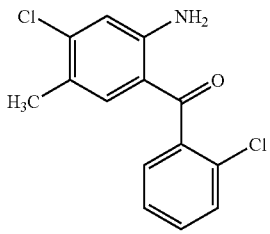

(2-amino-4-chloro-5-methylphenyl)-(2-chlorophenyl)-methanone (Xhh) was prepared by reacting 2-chlorobenzaldehyde with 0.0318 moles of 3-chloro-4-methyl aniline in a manner analogous to Example 1. MH+/Z=280.

Example 15

Preparation of (2-amino-5-methoxy-4-(1-methylethoxy)phenyl)-(2-chlorophenyl)-methanone (Xii)

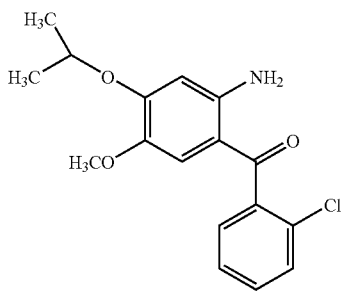

(2-amino-5-methoxy-4-(1-methylethoxy)phenyl)-(2-chlorophenyl)-methanone (Xii) was prepared by reacting 2-chlorobenzaldehyde with 0.0252 moles of 3-isopropoxy-4-methoxy aniline in a manner analogous to Example 1. MH+/Z=320.

Example 16

Preparation of (2-amino-4-methoxy-5-(1-methylethoxy)phenyl)-(2-chlorophenyl)-methanone

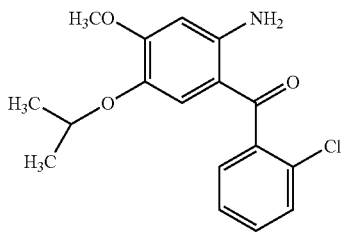

(2-amino-4-methoxy-5-(1-methylethoxy)phenyl)-(2-chlorophenyl)-methanone (Xjj) was prepared by reacting 2-chlorobenzaldehyde with 0.0267 moles of 4-isopropoxy-3-methoxy aniline in a manner analogous to Example 1. MH+/Z=320.

Example 17

Preparation of (2-amino-4-methoxy-5-(2-methoxyethoxy)phenyl)-(2-chlorophenyl)-methanone (Xkk)

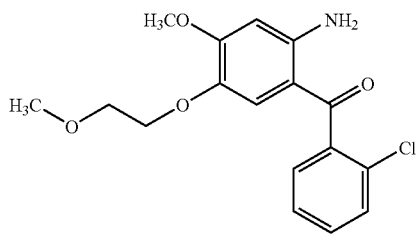

(2-amino-4-methoxy-5-(2-methoxyethoxy)phenyl)-(2-chlorophenyl)-methanone (Xkk) was prepared by reacting 2-chlorobenzaldehyde with 0.0242 moles of 3-methoxy-4-(2-methoxyethoxy) aniline in a manner analogous to Example 1. MH+/Z=336.

Example 18

Preparation of (2-amino-4,5-difluorophenyl)-(2-chlorophenyl)-methanone (Xmm)

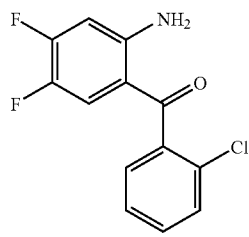

(2-amino-4,5-difluorophenyl)-(2-chlorophenyl)-methanone (Xmm) was prepared by reacting 2-chlorobenzaldehyde with 0.30 moles of 3,4-difluoro aniline in a manner analogous to Example 1. MH+/Z=268.

Example 19

Preparation of (2-amino-5-fluoro-4-methoxyphenyl)-(2-chlorophenyl)-methanone (Xa) from (2-amino-4,5-difluorophenyl)-(2-chlorophenyl)-methanone (Xmm)

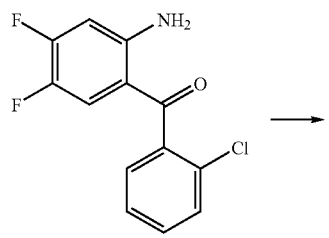

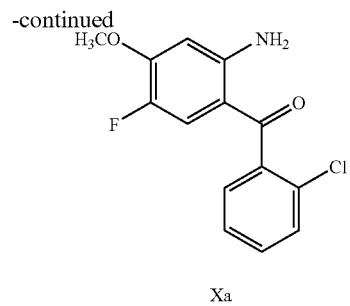

A solution of 2.01 g (0.0075 mole) of (2-amino-4,5-difluorophenyl)-(2-chlorophenyl)-methanone (Xmm), 24 mL of methanol and 2.08 mL of 25% sodium methoxide solution was heated to reflux under an inert atmosphere for 80 minutes. The mixture was then cooled, taken up in ethyl acetate and washed twice with brine. The ethyl acetate extract was dried over anhydrous sodium sulfate, filtered and concentrated under reduced pressure to yield 2.04 g of aminobenzophenone (2-amino-5-fluoro-4-methoxyphenyl)-(2-chlorophenyl)-methanone (Xa) as a crystalline yellow solid. MH+/Z=280.

Example 20

Preparation of (2-amino-5-fluoro-4-(3-(4-morpholinyl)propoxy)phenyl)-(2-chlorophenyl)-methanone (Xi)

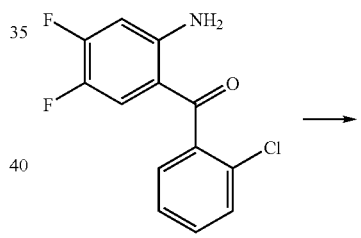

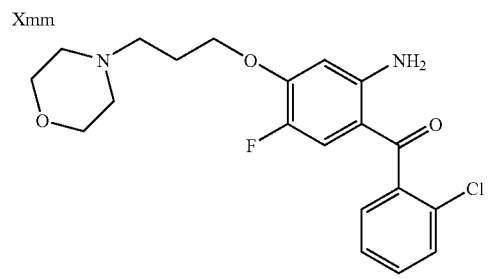

A mixture of 1.4 g (0.035 mole) of 60% sodium hydride, 25 mL of dioxane, 2.68 g (0.01 mole) of (2-amino-4,5-difluorophenyl)-(2-chlorophenyl)-methanone (Xmm) and 2.23 g (0.016 mole) of 4-morpholinepropanol was stirred at room temperature for 4 hours. The mixture was quenched by the addition of 50 mL of water. The mixture was extracted with ethyl acetate, and the extract washed with water, dried over anhydrous sodium sulfate, filtered and concentrated under reduced pressure. The residue was triturated with hexane and then recrystallized from hexane-ethyl acetate to give 2.55 g of (2-amino-5-fluoro-4-(3-(4-morpholinyl)propoxy)phenyl)-(2-chlorophenyl)-methanone (Xi). MH+/Z=393.

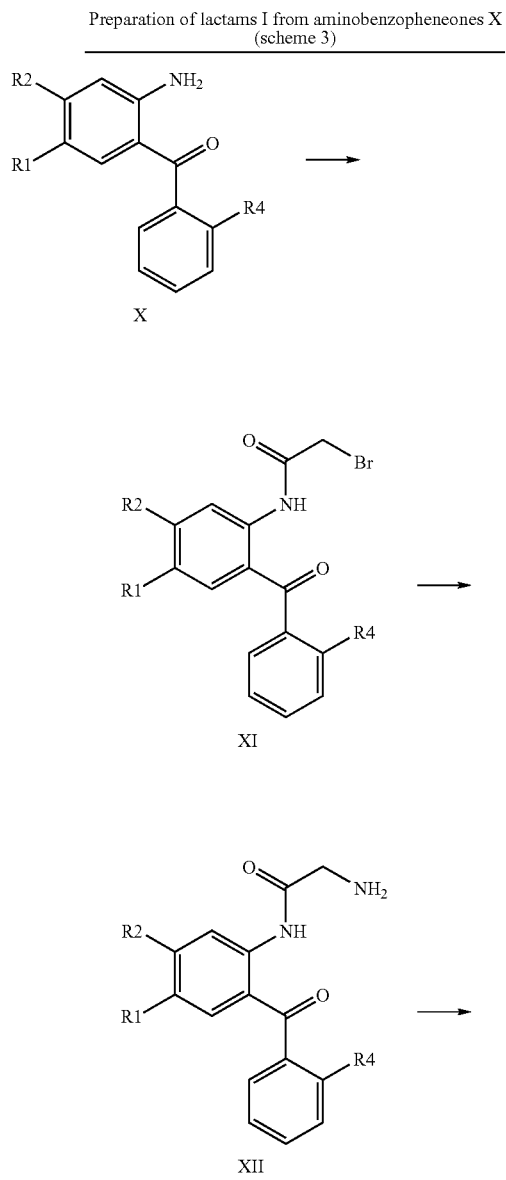

Example 21

Preparation of 7-bromo-5-(2-chlorophenyl)-1,3-dihydro-8-methoxy-2H-1,4-benzodiazepin-2-one (Id)

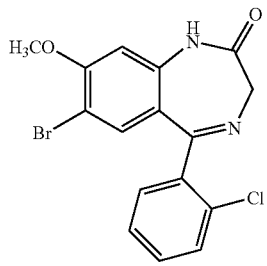

A solution of 3.5 mL (0.04 mole) of bromoacetyl bromide in 3.5 mL of dichloromethane was added to a cooled (0° C.) solution of 11.8 g (0.035 mole) of (2-amino-5-bromo-4-methoxyphenyl)-(2-chlorophenyl)-methanone (Xd), 2.94 mL of pyridine and 350 mL of dichloromethane over 30 minutes. The mixture was stirred an additional 1 hour at room temperature and then partitioned between water and dichloromethane. The dichloromethane layer was washed with saturated copper sulfate solution, dried over anhydrous sodium sulfate, filtered and concentrated under reduced pressure to give 16.5 g of bromoacetyl anilide XId.

The crude bromoacetanilide (XId) obtained above (16.5 g, 0.0357 mole) was dissolved in 250 mL, of tetrahydrofuran and 80 mL of methanol. The mixture was cooled to −78° C. and 35 mL of distilled ammonia was added. The mixture was stirred for 1.5 hours; then, the cooling bath was removed, and the mixture stirred at room temperature for another 2 hours, during which time the excess ammonia was allowed to boil off. The mixture was concentrated under reduced pressure, and the residue partitioned between ethyl acetate and water. The ethyl acetate layer was washed successively with water and then brine, dried over anhydrous sodium sulfate, filtered and concentrated under reduced pressure to provide 13.6 g of the crude amino-anilide XIId.

The crude XIId obtained in the previous reaction was suspended in 375 mL of ethanol, refluxed for 24 hours, and then cooled. The product was collected by filtration to yield 9.2 g of 7-bromo-5-(2-chlorophenyl)-1,3-dihydro-8-methoxy-2H-1,4-benzodiazepin-2-one (Id).

MH+/Z=379.

Example 22

Preparation of 5-(2-chlorophenyl)-1,3-dihydro-7-fluoro-8-methoxy-2H-1,4-benzodiazepin-2-one (Ia)

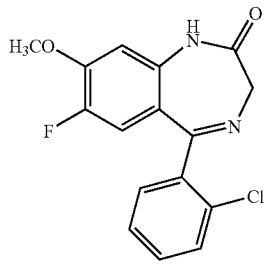

5-(2-chlorophenyl)-1,3-dihydro-7-fluoro-8-methoxy-2H-1,4-benzodiazepin-2-one (Ia) was prepared by reacting 0.125 moles of (2-amino-5-fluoro-4-methoxyphenyl)(2-chlorophenyl)-methanone (Xa) with bromoacetyl bromide in the manner of Example 21.

MH+/Z=319.

Example 23

Preparation of 5-(2-chlorophenyl)-1,3-dihydro-7-fluoro-8-(3-(4-morpholinyl)propoxy)-2H-1,4-benzodiazepin-2-one (Ii)

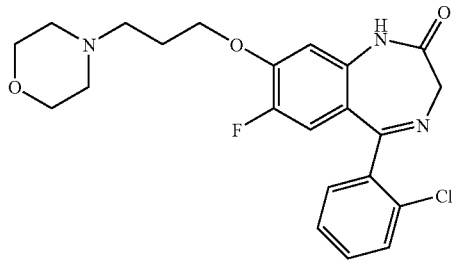

5-(2-chlorophenyl)-1,3-dihydro-7-fluoro-8-(3-(4-morpholinyl)propoxy)-2H-1,4-benzodiazepin-2-one (Ii) was prepared by reacting 0.0062 moles of (2-amino-5-fluoro-4-(3-(4-morpholinyl)propoxy)phenyl)-(2-chlorophenyl)-methanone (Xi) with bromoacetyl bromide in the manner of Example 21. MH+/Z=432.

Example 24

Preparation of 5-(2-chlorophenyl)-1,3-dihydro-8-methoxy-7-methyl-2H-1,4-benzodiazepin-2-one (Iz)

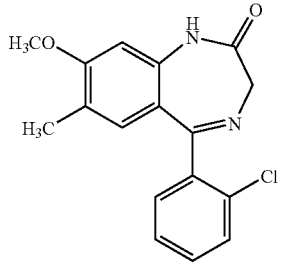

5-(2-chlorophenyl)-1,3-dihydro-8-methoxy-7-methyl-2H-1,4-benzodiazepin-2-one (Iz) was prepared by reacting 0.13 moles of (2-amino-4-methoxy-5-methylphenyl)-(2-chlorophenyl)-methanone (Xz) with bromoacetyl bromide in the manner of Example 21.

Example 25

Preparation of 5-(2-chlorophenyl)-7,8-difluoro-1,3-dihydro-2H-1,4-benzodiazepin-2-one (Imm)

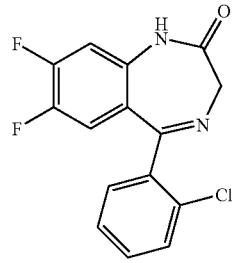

5-(2-chlorophenyl)-7,8-difluoro-1,3-dihydro-2H-1,4-benzodiazepin-2-one (Imm) was prepared by reacting 0.019 moles of (2-amino-4,5-difluorophenyl)-(2-chlorophenyl)-methanone (Xmm) with bromoacetyl bromide in the manner of Example 21. MH+/Z=307.

Conversions of lactams (scheme 8)

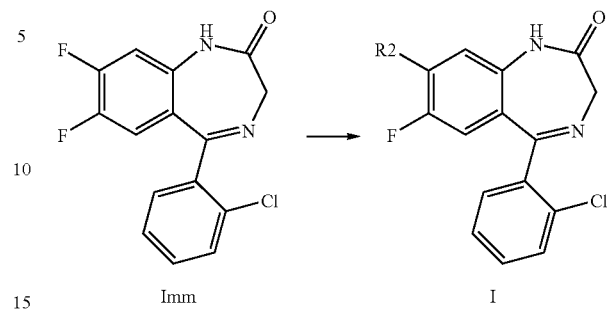

Example 26

Conversion of 5-(2-chlorophenyl)-7,8-difluoro-1,3-dihydro-2H-1,4-benzodiazepin-2-one (Imm) to 5-(2-chlorophenyl)-1,3-dihydro-7-fluoro-8-methoxy-2H-1,4-benzodiazepin-2-one (Ia)

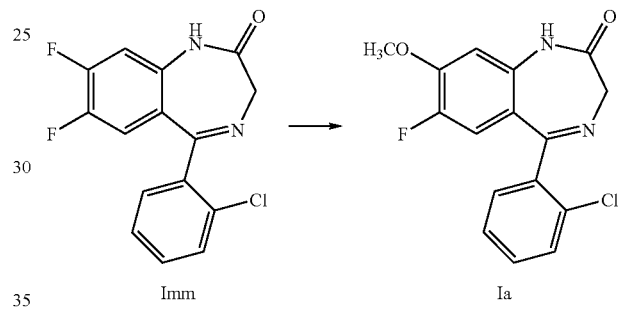

A mixture of 0.10 g (0.00033 mole) of 5-(2-chlorophenyl)-7,8-difluoro-1,3-dihydro-2H-1,4-benzodiazepin-2-one (Imm), 2 mL of methanol and 0.03 g of sodium hydride was heated at 100° C. for 40 minutes using microwave heating in a sealed reaction vessel. The mixture was then cooled. diluted with ethyl acetate and washed successively with water and then brine. The mixture was dried over anhydrous sodium sulfate, filtered and concentrated under reduced pressure to give 0.103 g of 5-(2-chlorophenyl)-1,3-dihydro-7-fluoro-8-methoxy-2H-1,4-benzodiazepin-2-one (Ia) as a white solid. MH+/Z=319.

Example 27

Conversion of 5-(2-chlorophenyl)-7,8-difluoro-1,3-dihydro-2H-1,4-benzodiazepin-2-one (Imm) to 5-(2-chlorophenyl)-8-N,N-dimethylamino-1,3-dihydro-7-fluoro-2H-1,4-benzodiazepin-2-one

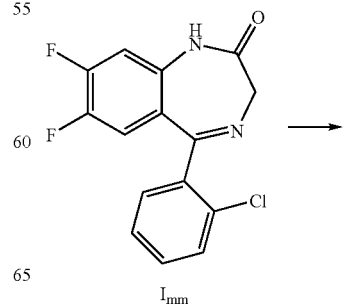

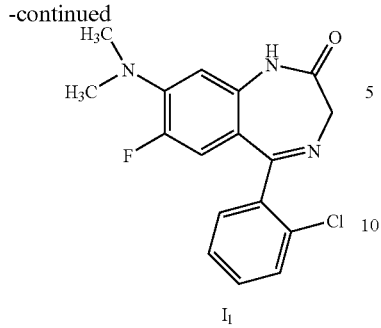

I₁

A mixture of 0.9201 g (0.003 mole) of 5-(2-chlorophenyl)-7,8-difluoro-1,3-dihydro-2H-1,4-benzodiazepin-2-one (Imm) and 3 mL of a 2.0 M solution of dimethylamine in tetrahydrofuran was heated at 150° C. for 30 minutes using microwave heating. The mixture was cooled and then concentrated under reduced pressure. The residue was triturated with ethyl acetate-hexane to give 0.63 g of 5-(2-chlorophenyl)-8-N,N-dimethylamino-1,3-dihydro-7-fluoro-2H-1,4-benzodiazepin-2-one (Il) as a yellow solid.
MH+/Z=332.

Conversion of lactams
(Scheme 10)

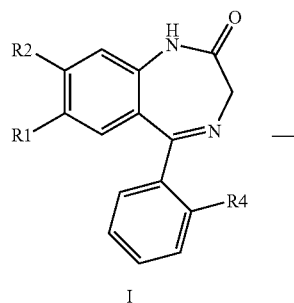

I

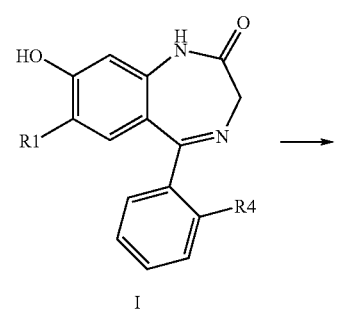

I

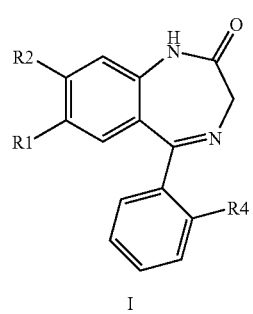

I

Example 28

Conversion of 7-bromo-5-(2-chlorophenyl)-1,3-dihydro-8-methoxy-2H-1,4-benzodiazepin-2-one (Id) to 7-bromo-5-(2-chlorophenyl)-1,3-dihydro-8-(3-(4-morpholinyl)propoxy)-2H-1,4-benzodiazepin-2-one (Ii)

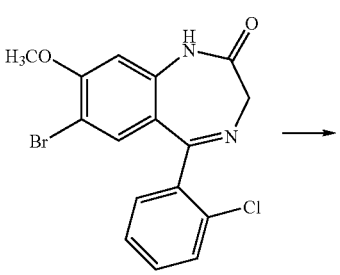

Id

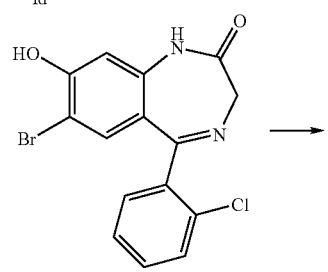

Ip

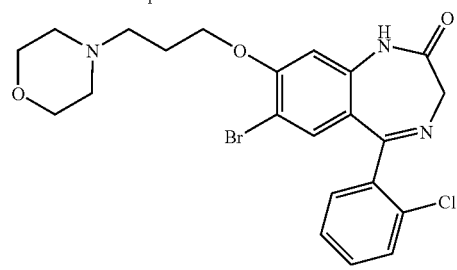

Ij

A solution of 1.00 g (0.0263 mole) of 7-bromo-5-(2-chlorophenyl)-1,3-dihydro-8-methoxy-2H-1,4-benzodiazepin-2-one (Id) in 85 mL of 1,2-dichloroethane was stirred overnight with 1.053 g (0.0079 mole) of aluminum trichloride. An additional 1.00 g of aluminum trichloride was added, and the mixture stirred overnight, after which time the mixture was poured into ice water. The mixture was extracted with dichloromethane-methanol, and the organic layer washed twice with water and then dried over anhydrous sodium sulfate. The solution was concentrated under reduced pressure to provide 0.700 g of 7-bromo-5-(2-chlorophenyl)-1,3-dihydro-8-hydroxy-2H-1,4-benzodiazepin-2-one (Ipp) (MH+/Z=465), which was of sufficient purity to be used in the next step.

A mixture of 1.8281 g (0.005 mole) of 7-bromo-5-(2-chlorophenyl)-1,3-dihydro-8-hydroxy-2H-1,4-benzodiazepin-2-one (Ipp) from the previous step, 0.636 g of sodium carbonate, 0.9818 g (0.006 mole) of 4-(3-chloropropyl)-morpholine and 50 mL of dimethylformamide was stirred at 50° C., under an argon atmosphere for 73 hours. The mixture was then cooled and partitioned between ethyl acetate and saturated sodium bicarbonate. The aqueous layer was then reextracted with ethyl acetate. The ethyl acetate layers were washed successively with saturated sodium bicarbonate, water, brine and then dried over anhydrous sodium sulfate, filtered and concentrated under reduced pressure to give the crude 7-bromo-5-(2-chlorophenyl)-1,3-dihydro-8-(3-(4-morpholinyl)propoxy)-2H-1,4-benzodiazepin-2-one (Ij). Pure 7-bromo-5-(2-chlorophenyl)-1,3-dihydro-8-(3-(4-morpholinyl)propoxy)-2H-1,4-benzodiazepin-2-one (Ij) (1.721 g) was obtained by silica gel chromatography eluting with ethyl acetate-methanol (90:10). MH+/Z=492.

Example 29

Conversion of 5-(2-chlorophenyl)-7-cyano-1,3-dihydro-8-methoxy-2H-1,4-benzodiazepin-2-one (Ib) to 5-(2-chlorophenyl)-7-cyano-1,3-dihydro-8-(3-(4-morpholinyl)propoxy)-2H-1,4-benzodiazepin-2-one (Ik)

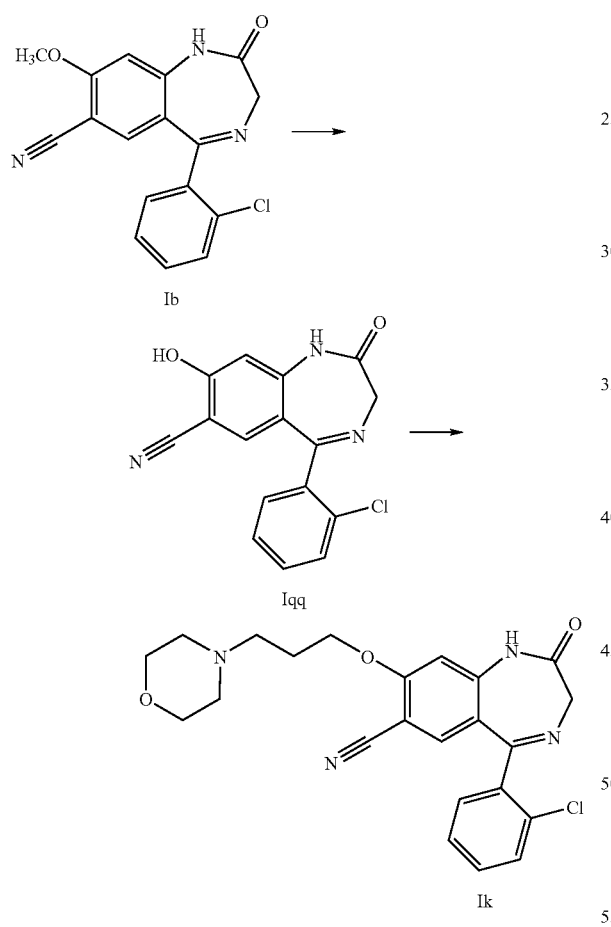

A solution of 1.2 g (0.0037 mole) of 5-(2-chlorophenyl)-7-cyano-1,3-dihydro-8-methoxy-2H-1,4-benzodiazepin-2-one (Ib, prepared in Example 30) in 100 mL of 1,2-dichloroethane was stirred with 2.5 g (0.0187 mole) of aluminum trichloride at 42° C. for 8 hours, after which an additional 2.5 g of aluminum trichloride was added. Heating and stirring was continued for another 48 hours after which time an additional 2.5 g of aluminum trichloride was added. After 6 hours, the mixture was cooled and then poured onto ice water. The water was extracted with dichloromethane-methanol-tetrahydrofuran (80:10:10), and the extract washed with water, dried over anhydrous sodium sulfate, filtered and concentrated under reduced pressure to give 1.6 g of crude 5-(2-chlorophenyl)-7-cyano-1,3-dihydro-8-hydroxy-2H-1,4-benzodiazepin-2-one (Iqq). Purification by silica gel chromatography, eluting with ethyl acetate-methanol (90:10) yielded 1.17 g of 5-(2-chlorophenyl)-7-cyano-1,3-dihydro-8-hydroxy-2H-1,4-benzodiazepin-2-one (Iqq) (MH+/Z=312) which was of sufficient purity for use in the next step.

A mixture of 0.322 g (0.00103 mole) of 5-(2-chlorophenyl)-7-cyano-1,3-dihydro-8-hydroxy-2H-1,4-benzodiazepin-2-one (Iqq), 6 mL of dimethylformamide, 0.132 g (0.00124 mole) of sodium carbonate and 0.2028 g (0.00124 mole) of 4-(3-chloropropyl)-morpholine was stirred 50° C. under an atmosphere of argon for 24 hours. The mixture was then cooled and partitioned between ethyl acetate and water. The aqueous phase was reextracted with ethyl acetate and the ethyl acetate extracts were then dried over anhydrous sodium sulfate, filtered and concentrated under reduced pressure. The residue was purified by chromatography on silica gel eluting with acetonitrile-methanol (90:10), to provide 0.199 g of 5-(2-chlorophenyl)-7-cyano-1,3-dihydro-8-(3-(4-morpholinyl)propoxy)-2H-1,4-benzodiazepin-2-one (Ik). MH+/Z=439.

Example 30

Conversion of 7-bromo-5-(2-chlorophenyl)-1,3-dihydro-8-methoxy-2H-1,4-benzodiazepin-2-one (Id) to 5-(2-chlorophenyl)-7-cyano-1,3-dihydro-8-methoxy-2H-1,4-benzodiazepin-2-one (Ib)

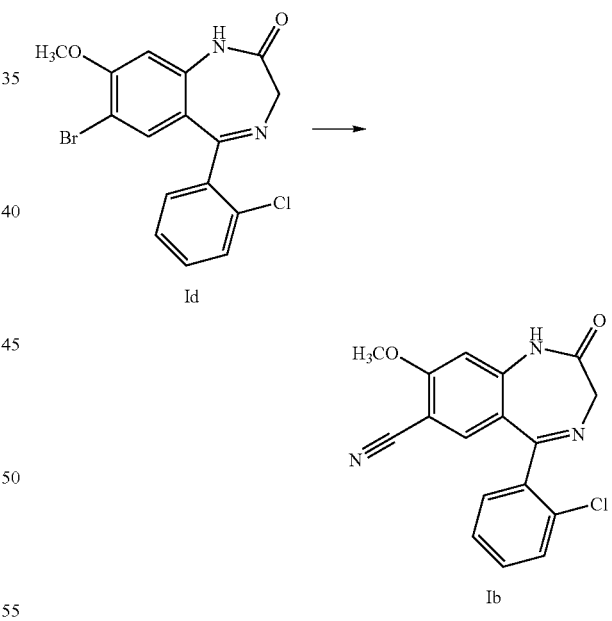

5-(2-chlorophenyl)-7-cyano-1,3-dihydro-8-methoxy-2H-1,4-benzodiazepin-2-one (Ib) was prepared from 7-bromo-5-(2-chlorophenyl)-1,3-dihydro-8-methoxy-2H-1,4-benzodiazepin-2-one (Id) by reaction with zinc cyanide in the presence of a palladium catalyst (tetrakistriphenyl phosphine palladium) according to conditions similar to those described by Tschaen et al., Synthetic Communications, 24:887-90 (1994). A mixture of 0.9491 g (0.0025 mole) of 7-bromo-5-(2-chlorophenyl)-1,3-dihydro-8-methoxy-2H-1,4-benzodiazepin-2-one (Id), 0.176 g (0.0015 mole) of zinc cyanide, 4 mL of dimethylformamide and 0.289 g (0.00025 mole) of tetrakistriphenyl phosphine palladium was heated at 110° C.

under an argon atmosphere for 24 hours. The mixture was then cooled, taken up in ethyl acetate and washed with 0.2 M sodium carbonate solution. The aqueous phase was reextracted with ethyl acetate, and the ethyl acetate layers washed with water, dried over anhydrous sodium sulfate, filtered and concentrated under reduced pressure. The residue was chromatographed on silica gel eluting with ethyl acetate-hexane (4:1) to give 0.620 g of 5-(2-chlorophenyl)-7-cyano-1,3-dihydro-8-methoxy-2H-1,4-benzodiazepin-2-one (Ib). MH+/Z=326.

Example 31

Conversion of 7-bromo-5-(2-chlorophenyl)-1,3-dihydro-8-methoxyethoxy-2H-1,4-benzodiazepin-2-one (Inn) to 5-(2-chlorophenyl)-7-cyano-1,3-dihydro-8-methoxyethoxy-2H-1,4-benzodiazepin-2-one (Im)

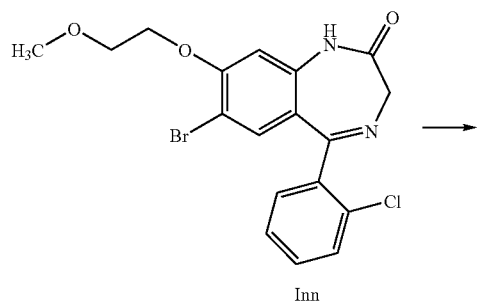

5-(2-chlorophenyl)-7-cyano-1,3-dihydro-8-methoxyethoxy-2H-1,4-benzodiazepin-2-one (Im) was prepared by reacting 0.001 moles of 7-bromo-5-(2-chlorophenyl)-1,3-dihydro-8-methoxyethoxy-2H-1,4-benzodiazepin-2-one (Inn) with zinc cyanide, in the presence of tetrakistriphenyl phosphine palladium in a manner analogous to Example 30. MH+/Z=370.

Example 32

Conversion of 7-bromo-5-(2-chlorophenyl)-1,3-dihydro-8-(2-(2-methoxyethoxy)ethoxy)-2H-1,4-benzodiazepin-2-one (Ioo) to 5-(2-chlorophenyl)-7-cyano-1,3-dihydro-8-(2-(2-methoxyethoxy)ethoxy)-2H-1,4-benzodiazepin-2-one (In)

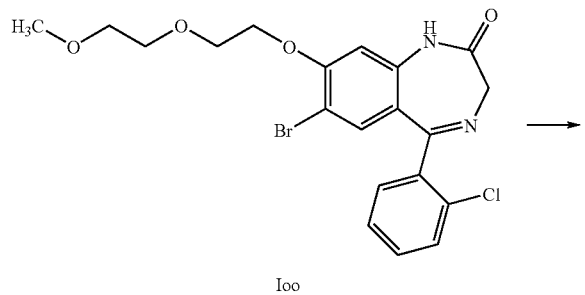

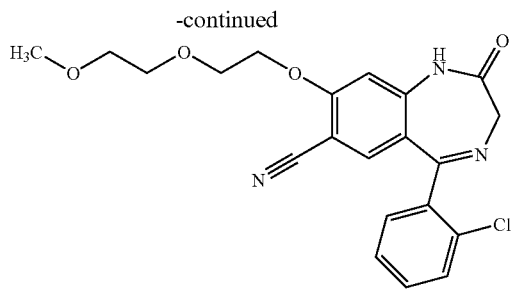

5-(2-chlorophenyl)-7-cyano-1,3-dihydro-8-(2-(2-methoxyethoxy)ethoxy)-2H-1,4-benzodiazepin-2-one (In) was prepared by reacting 0.0017 moles of 7-bromo-5-(2-chlorophenyl)-1,3-dihydro-8-(2-(2-methoxyethoxy)ethoxy)-2H-1,4-benzodiazepin-2-one (Ioo) with zinc cyanide, in the presence of tetrakistriphenyl phosphine palladium in a manner analogous to Example 30. MH+/Z=414.

Example 33

Preparation of 7-bromo-5-(2-chlorophenyl)-1,3-dihydro-8-methoxyethoxy-2H-1,4-benzodiazepin-2-one (Inn) from 7-bromo-5-(2-chlorophenyl)-1,3-dihydro-8-hydroxy-2H-1,4-benzodiazepin-2-one (Ipp)

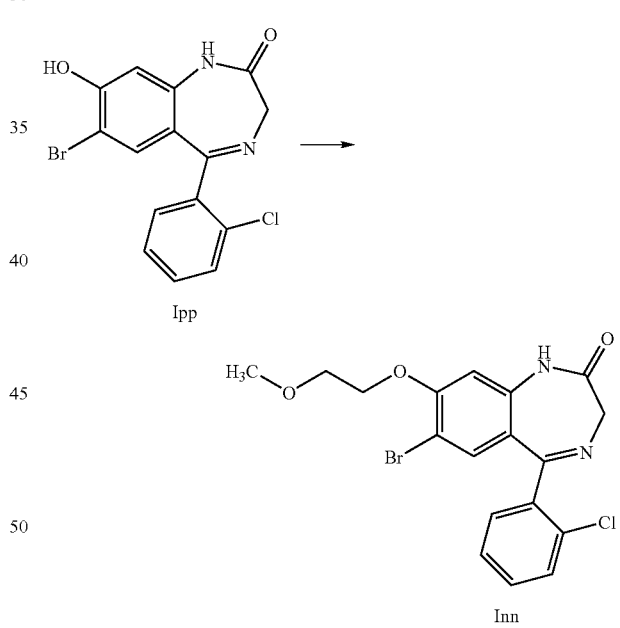

To a stirred mixture of 0.300 g (0.00082 mole) 7-bromo-5-(2-chlorophenyl)-1,3-dihydro-8-hydroxy-2H-1,4-benzodiazepin-2-one (Ipp) prepared in Example 28, 60 mL of tetrahydrofuran, 0.070 mL of 2-methoxy ethanol, and 0.2586 g of triphenyl phosphine was added 0.194 mL (0.00099 mole) of diisopropyl azodicarboxylate. The mixture was stirred overnight; then, an additional 0.2586 g of triphenyl phosphine, 0.070 mL of 2-methoxy ethanol and 0.194 mL of diisopropyl azodicarboxylate was added. The mixture stirred for an additional hour and then concentrated under reduced pressure. The residue was chromatographed on silica gel eluting with dichloromethane-methanol (98:2) to yield 0.212 g of 7-bromo-5-(2-chlorophenyl)-1,3-dihydro-8-methoxy-ethoxy-2H-1,4-benzodiazepin-2-one (Inn). MH+/Z=423.

Example 34

Preparation of 7-bromo-5-(2-chlorophenyl)-1,3-dihydro-8-(2-(2-methoxyethoxy)ethoxy)-2H-1,4-benzodiazepin-2-one (Ioo) from 7-bromo-5-(2-chlorophenyl)-1,3-dihydro-8-hydroxy-2H-1,4-benzodiazepin-2-one (Ipp)

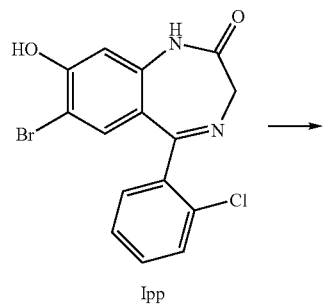

Ipp

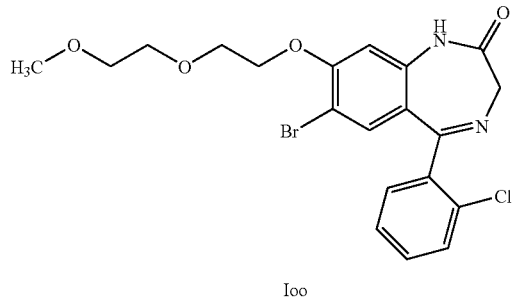

Ioo 7-bromo-5-(2-chlorophenyl)-1,3-dihydro-8-(2-(2-methoxyethoxy)ethoxy)-2H-1,4-benzodiazepin-2-one (Ioo) was prepared by reacting 0.00238 moles of 7-bromo-5-(2-chlorophenyl)-1,3-dihydro-8-hydroxy-2H-1,4-benzodiazepin-2-one (Ipp) with 2-(2-methoxyethoxy)ethanol in a manner analogous to Example 33. MH+/Z=467.

Example 35

Preparation of 8-(2-chloroethoxy)-5-(2-chlorophenyl)-7-cyano-1,3-dihydro-2H-1,4-benzodiazepin-2-one (Iss) from 5-(2-chlorophenyl)-7-cyano-1,3-dihydro-8-hydroxy-2H-1,4-benzodiazepin-2-one (Iqq)

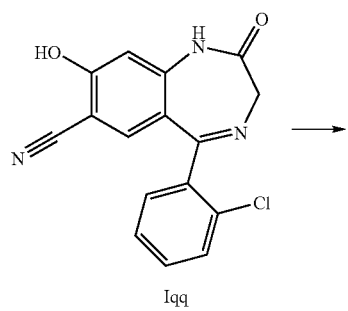

Iqq

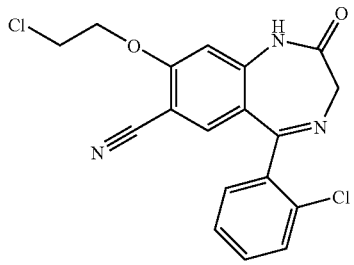

Iss 8-(2-chloroethoxy)-5-(2-chlorophenyl)-7-cyano-1,3-dihydro-2H-1,4-benzodiazepin-2-one (Iss) was prepared by reacting 0.0031 moles of 5-(2-chlorophenyl)-7-cyano-1,3-dihydro-8-hydroxy-2H-1,4-benzodiazepin-2-one (Iqq) with 2-chloroethanol in a manner analogous to Example 33. MH+/Z=374.

Example 36

Preparation of 5-(2-chlorophenyl)-7-cyano-1,3-dihydro-8-(2-((2-methoxyethyl)methylamino)-ethoxy)-2H-1,4-benzodiazepin-2-one (Iv)

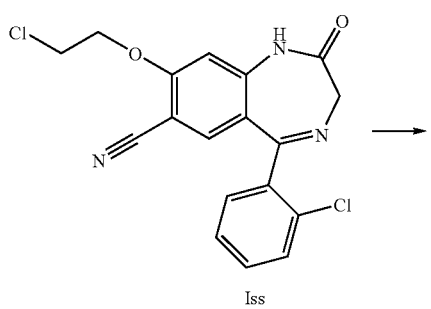

Iss

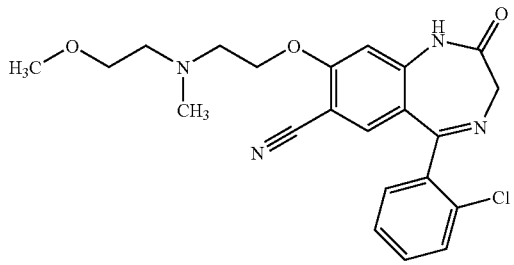

Iv

A mixture of 1.2 g (0.0032 mole) of 8-(2-chloroethoxy)-5-(2-chlorophenyl)-7-cyano-1,3-dihydro-2H-1,4-benzodiazepin-2-one (Iss, prepared in Example 35), 2.85 g (0.032 mole) of 2-((2-methoxyethyl)methylamino) ethanol, 20 mL of tetrahydrofuran and 4.8 g (0.032 mole) of sodium iodide was heated in an oil bath at 83° C. under an argon atmosphere for 20 hours. The mixture was cooled and then partitioned between ethyl acetate and 0.6 M sodium bicarbonate solution. The ethyl acetate layer was washed with brine, dried over anhydrous sodium sulfate, filtered and concentrated under reduced pressure. The residue was chromatographed on silica gel, eluting with acetonitrile-methanol (80:20) to give 0.233 g of 5-(2-chlorophenyl)-7-cyano-1,3-dihydro-8-(2-((2-methoxyethyl)methylamino)-ethoxy)-2H-1,4-benzodiazepin-2-one (Iv).

MH+/Z=427.

Example 37

Preparation of 5-(2-chlorophenyl)-7-cyano-1,3-dihydro-8-(2-((2-(4-methyl-1-piperazinyl)ethoxy))-2H-1,4-benzodiazepin-2-one (It)

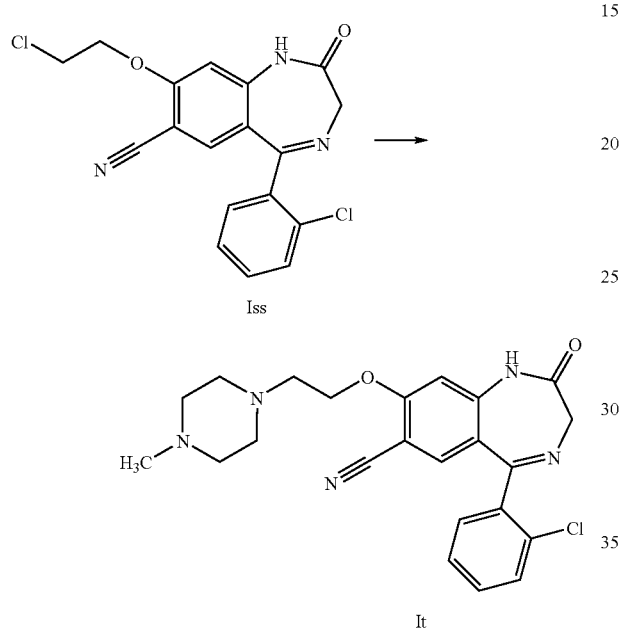

5-(2-chlorophenyl)-7-cyano-1,3-dihydro-8-(2-((2-(4-methyl-1-piperazinyl)ethoxy))-2H-1,4-benzodiazepin-2-one (It) was prepared by reacting 0.00414 moles of 8-(2-chloroethoxy)-5-(2-chlorophenyl)-7-cyano-1,3-dihydro-2H-1,4-benzodiazepin-2-one (Iss) with N-methyl piperazine in a manner analogous to Example 36.

Formation of thiolactams (II) from lactams (I) (scheme 1)

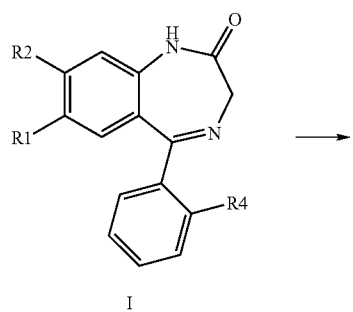

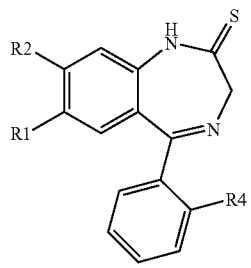

Example 38

Preparation of 7-bromo-5-(2-chlorophenyl)-1,3-dihydro-8-methoxy-2H-1,4-benzodiazepin-2-thione (IId)

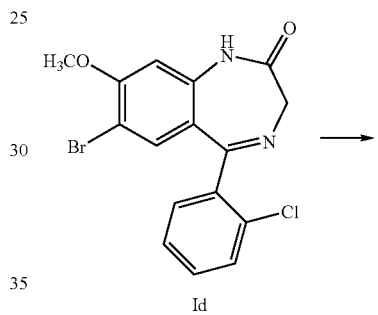

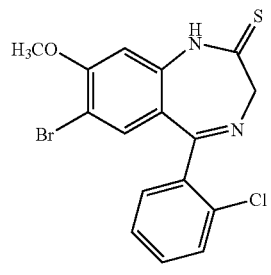

A mixture of 2.0 g (0.0053 mole) of 7-bromo-5-(2-chlorophenyl)-1,3-dihydro-8-methoxy-2H-1,4-benzodiazepin-2-one (Id), 200 mL of 1,2-dimethoxyethane and 2.13 g (0.0053 mole) of Lawesson's reagent (2,4-bis(4-methoxyphenyl)-2,4-disulfide-1,3,2,4-dithiadiphosphetane) was heated at 85° C. for 1 hour, then cooled and poured onto ice cold sodium bicarbonate solution. The mixture was extracted twice with ethyl acetate-methanol (9:1), and the organic layers washed successively with water and brine. The combined extracts were dried over anhydrous sodium sulfate, filtered and concentrated under reduced pressure. Trituration of the residue with ethyl acetate provided 1.7 g of 7-bromo-5-(2-chlorophenyl)-1,3-dihydro-8-methoxy-2H-1,4-benzodiazepin-2-thione (IId). MH+/Z=395.

Example 39

Preparation of 5-(2-chlorophenyl)-1,3-dihydro-7-fluoro-8-methoxy-2H-1,4-benzodiazepin-2-thione (IIa)

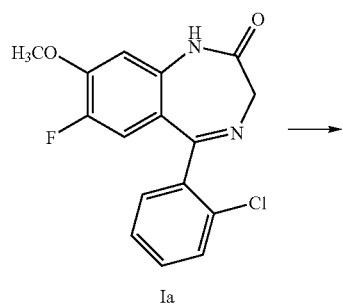

Ia

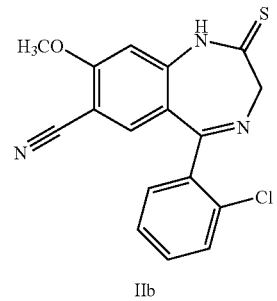

IIb 5-(2-chlorophenyl)-7-cyano-1,3-dihydro-8-methoxy-2H-1,4-benzodiazepin-2-thione (IIb) was prepared by reacting 0.0019 moles of 5-(2-chlorophenyl)-7-cyano-1,3-dihydro-8-methoxy-2H-1,4-benzodiazepin-2-one (Ib) with Lawesson's reagent in a manner analogous to Example 38. MH+/Z=342.

Example 41

Preparation of 5-(2-chlorophenyl)-1,3-dihydro-7-fluoro-8-(3-(4-morpholinyl)propoxy)-2H-1,4-benzodiazepin-2-thione (IIi)

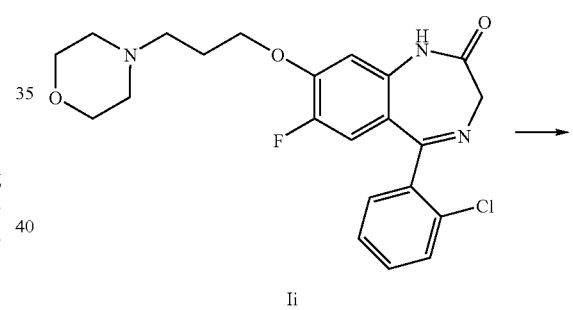

Ii

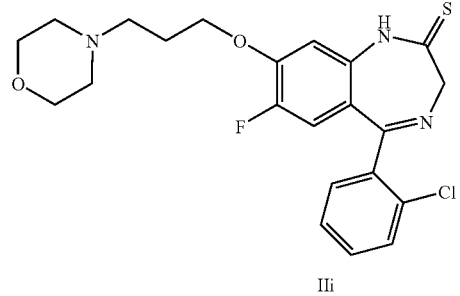

IIi 5-(2-chlorophenyl)-1,3-dihydro-7-fluoro-8-(3-(4-morpholinyl)propoxy)-2H-1,4-benzodiazepin-2-thione (IIi) was prepared by reacting 0.0053 moles of 5-(2-chlorophenyl)-1,3-dihydro-7-fluoro-8-(3-(4-morpholinyl)propoxy)-2H-1,4-benzodiazepin-2-one (lactam Ii) with Lawesson's reagent in a manner analogous to Example 38.

MH+/Z=448.

IIa 5-(2-chlorophenyl)-1,3-dihydro-7-fluoro-8-methoxy-2H-1,4-benzodiazepin-2-thione (IIa) was prepared by reacting 0.0284 moles of 5-(2-chlorophenyl)-1,3-dihydro-7-fluoro-8-methoxy-2H-1,4-benzodiazepin-2-one (Ia) with Lawesson's reagent in a manner analogous to Example 38.

MH+/Z=335.

Example 40

Preparation of 5-(2-chlorophenyl)-7-cyano-1,3-dihydro-8-methoxy-2H-1,4-benzodiazepin-2-thione (IIb)

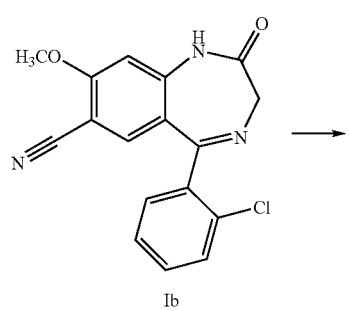

Ib

Example 42

Preparation of 7-bromo-5-(2-chlorophenyl)-1,3-dihydro-8-(3-(4-morpholinyl)propoxy)-2H-1,4-benzodiazepin-2-thione (IIi)

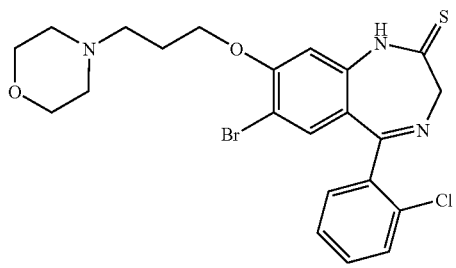

7-bromo-5-(2-chlorophenyl)-1,3-dihydro-8-(3-(4-morpholinyl)propoxy)-2H-1,4benzodiazepin-2-thione (IIj) was prepared by reacting 0.0011 moles of 7-bromo-5-(2-chlorophenyl)-1,3-dihydro-8-(3-(4-morpholinyl)propoxy)-2H-1,4-benzodiazepin-2-one (Ij) with Lawesson's reagent in a manner analogous to Example 38. MH+/Z=508.

Example 43

Preparation of 5-(2-chlorophenyl)-7-cyano-1,3-dihydro-8-(3-(4-morpholinyl)propoxy)-2H-1,4-benzodiazepin-2-thione (IIk)

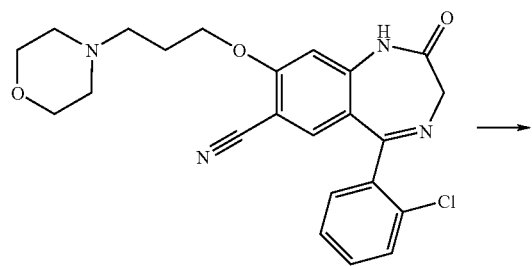

Ik

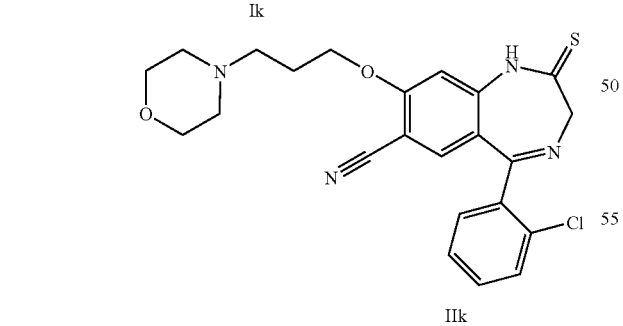

IIk 5-(2-chlorophenyl)-7-cyano-1,3-dihydro-8-(3-(4-morpholinyl)propoxy)-2H-1,4-benzodiazepin-2-thione (Ik) was prepared by reacting 0.00057 moles of 5-(2-chlorophenyl)-7-cyano-1,3-dihydro-8-(3-(4-morpholinyl)propoxy)-2H-1,4-benzodiazepin-2-one (Ik) with Lawesson's reagent in a manner analogous to Example 38. MH+/Z=455.

Example 44

Preparation of 5-(2-chlorophenyl)-8-N,N-dimethylamino-1,3-dihydro-7-fluoro-2H-1,4-benzodiazepin-2-thione (III)

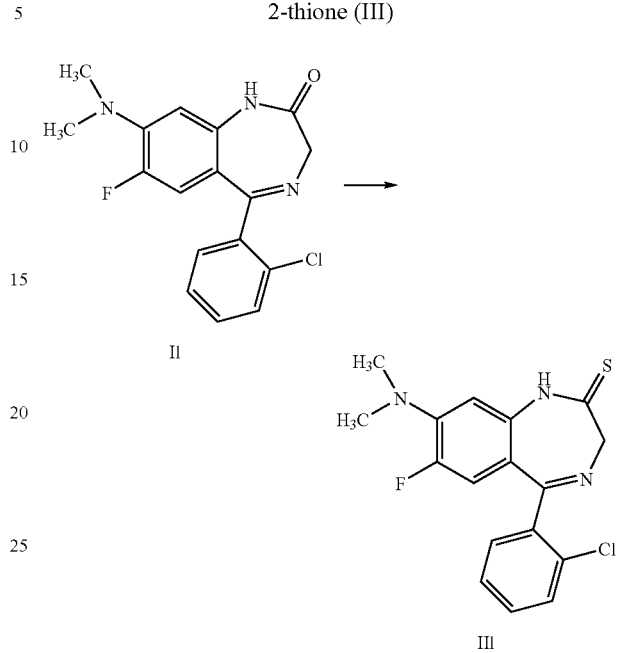

Il

III 5-(2-chlorophenyl)-8-N,N-dimethylamino-1,3-dihydro-7-fluoro-2H-1,4-benzodiazepin-2-thione (III) was prepared by reacting 0.006 moles of 5-(2-chlorophenyl)-8-N,N-dimethylamino-1,3-dihydro-7-fluoro-2H-1,4-benzodiazepin-2-one (Il) with Lawesson's reagent in a manner analogous to Example 38. MH+/Z=348.

Example 45

Preparation of 5-(2-chlorophenyl)-7-cyano-1,3-dihydro-8-methoxyethoxy-2H-1,4-benzodiazepin-2-thione (IIm)

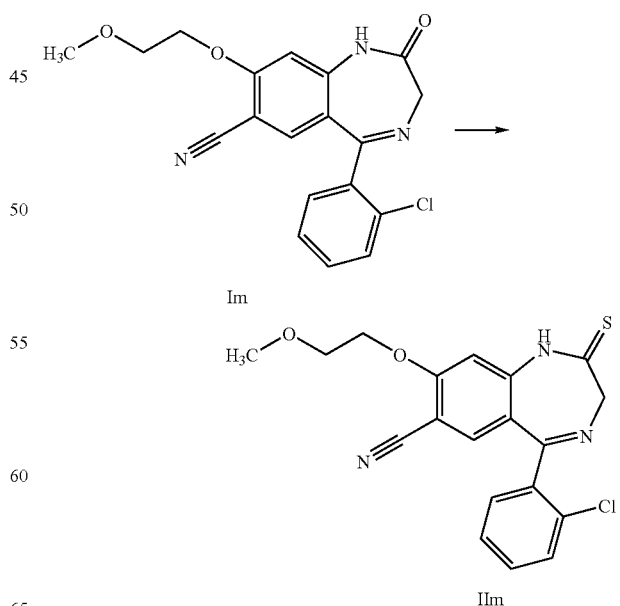

Im

IIm 5-(2-chlorophenyl)-7-cyano-1,3-dihydro-8-methoxyethoxy-2H-1,4-benzodiazepin-2-thione (IIm) was prepared by reacting 0.00081 moles of 5-(2-chlorophenyl)-7-cyano-1,3-dihydro-8-methoxyethoxy-2H-1,4-benzodiazepin-2-one (Im) with Lawesson's reagent in a manner analogous to Example 38. MH+/Z=386.

Example 46

Preparation of 5-(2-chlorophenyl)-7-cyano-1,3-dihydro-8-(2-(2-methoxyethoxy)ethoxy)-2H-1,4-benzodiazepin-2-thione (IIn)

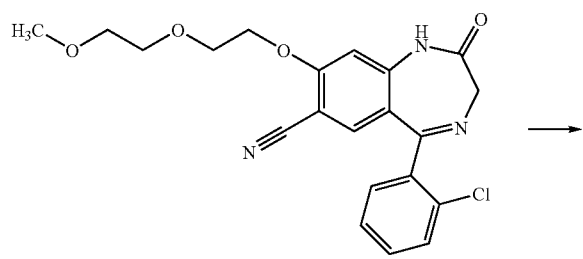

In

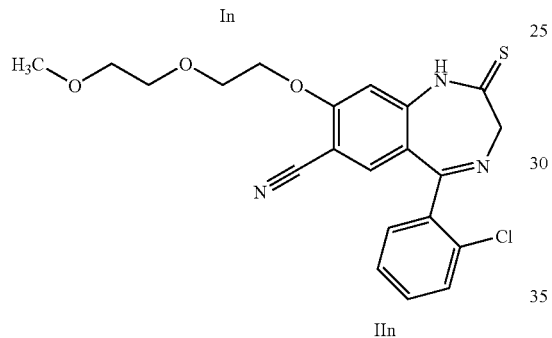

IIn 5-(2-chlorophenyl)-7-cyano-1,3-dihydro-8-(2-(2-methoxyethoxy)ethoxy)-2H-1,4-benzodiazepin-2-thione (IIn) was prepared by reacting 0.00089 moles of 5-(2-chlorophenyl)-7-cyano-1,3-dihydro-8-(2-(2-methoxyethoxy)ethoxy)-2H-1,4-benzodiazepin-2-one (lactam In) with Lawesson's reagent in a manner analogous to Example 38. MH+/Z=430.

Example 47

Preparation of 5-(2-chlorophenyl)-7-cyano-1,3-dihydro-8-(2-(2-(4-methyl-1-piperazinyl)ethoxy))-2H-1,4-benzodiazepin-2-thione (IIt)

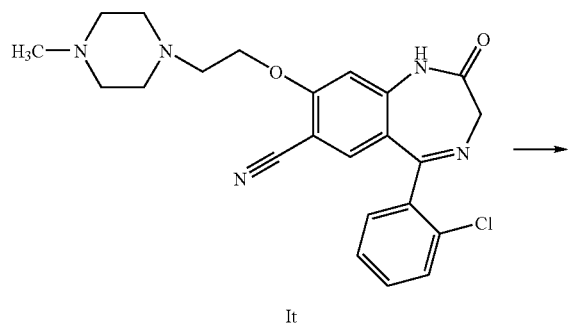

It

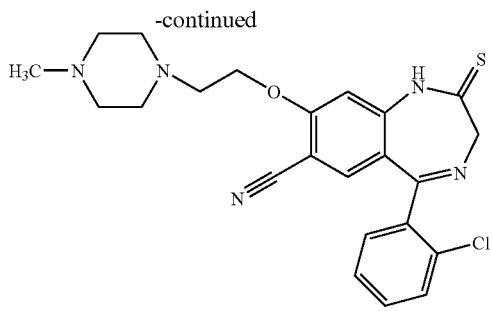

IIt 5-(2-chlorophenyl)-7-cyano-1,3-dihydro-8-(2-(2-(4-methyl-1-piperazinyl)ethoxy))-2H-1,4-benzodiazepin-2-thione (IIt) was prepared by reacting 0.00069 moles of 5-(2-chlorophenyl)-7-cyano-1,3-dihydro-8-(2-(2-(4-methyl-1-piperazinyl)ethoxy))-2H-1,4-benzodiazepin-2-one (It) with Lawesson's reagent in a manner analogous to Example 38.

Example 48

Preparation of 5-(2-chlorophenyl)-7-cyano-1,3-dihydro-8-(2-((2-methoxyethyl)methylamino)-ethoxy)-2H-1,4-benzodiazepin-2-thione (IIv)

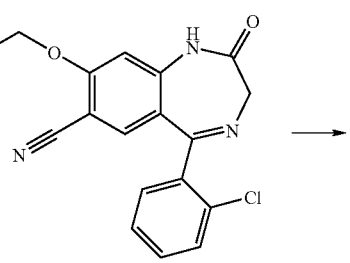

Iv

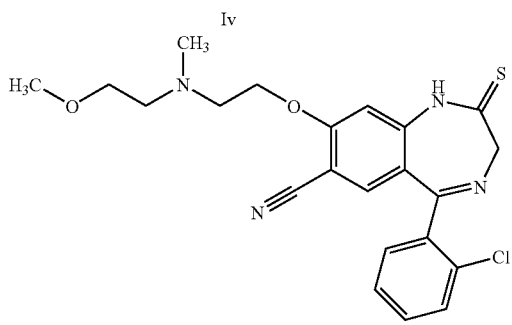

IIv 5-(2-chlorophenyl)-7-cyano-1,3-dihydro-8-(2-((2-methoxyethyl)methylamino)-ethoxy)-2H-1,4-benzodiazepin-2-thione (IIv) was prepared by reacting 0.00052 moles of 5-(2-chlorophenyl)-7-cyano-1,3-dihydro-8-(2-((2-methoxyethyl)methylamino)-ethoxy)-2H-1,4-benzodiazepin-2-one (Iv) with Lawesson's reagent in a manner analogous to Example 38

MH+/Z=443. .

Example 49

Preparation of 5-(2-chlorophenyl)-1,3-dihydro-7,8-dimethyl-2H-1,4-benzodiazepin-2-thione (IIw)

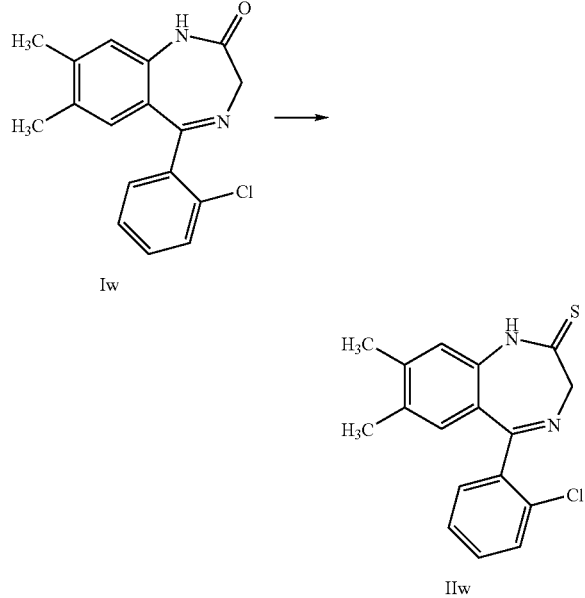

5-(2-chlorophenyl)-1,3-dihydro-7,8-dimethyl-2H-1,4-benzodiazepin-2-thione (Iw) was prepared by reacting 0.0006 moles of 5-(2-chlorophenyl)-1,3-dihydro-7,8-dimethyl-2H-1,4-benzodiazepin-2-one (Iw) with Lawesson's reagent in a manner analogous to Example 38.

MH+/Z=315.

Example 50

Preparation of 5-(2-chlorophenyl)-1,3-dihydro-8-methoxy-7-methyl-2H-1,4-benzodiazepin-2-thione (IIz)

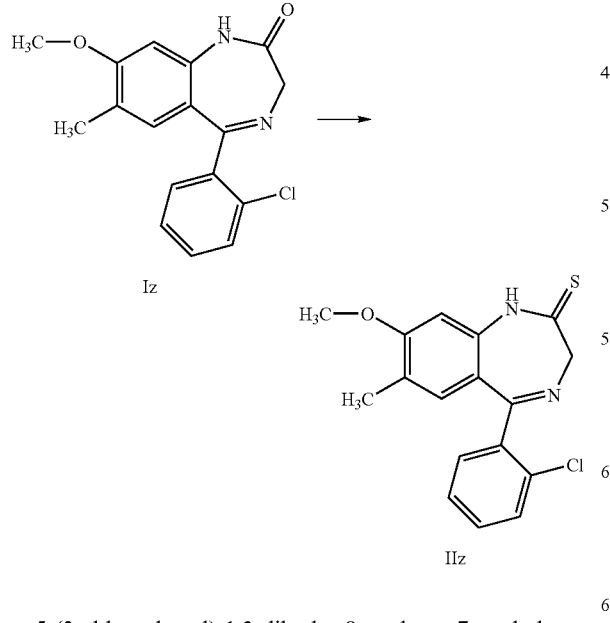

5-(2-chlorophenyl)-1,3-dihydro-8-methoxy-7-methyl-2H-1,4-benzodiazepin-2-thione (IIz) was prepared by react-ing 0.0064 moles of 5-(2-chlorophenyl)-1,3-dihydro-8-methoxy-7-methyl-2H-1,4-benzodiazepin-2-one (Iz) with Lawesson's reagent in a manner analogous to Example 38.

MH+/Z=331.

Example 51

Preparation of 5-(2-chlorophenyl)-1,3-dihydro-7,8-difluoro-2H-1,4-benzodiazepin-2-thione (IImm)

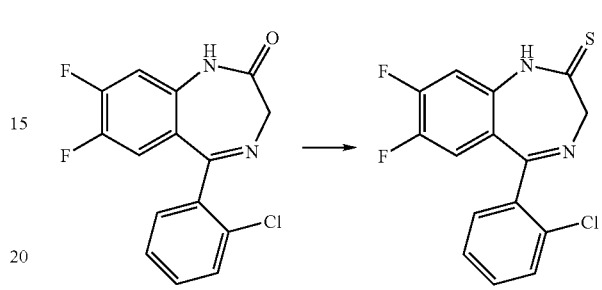

5-(2-chlorophenyl)-1,3-dihydro-7,8-difluoro-2H-1,4-benzodiazepin-2-thione (IImm) was prepared by reacting 0.003 moles of 5-(2-chlorophenyl)-1,3-dihydro-7,8-difluoro-2H-1,4-benzodiazepin-2-one (Imm) with Lawesson's reagent in a manner analogous to Example 38.

MH+/Z=332.

Conversion of thiolactams
(scheme 9)

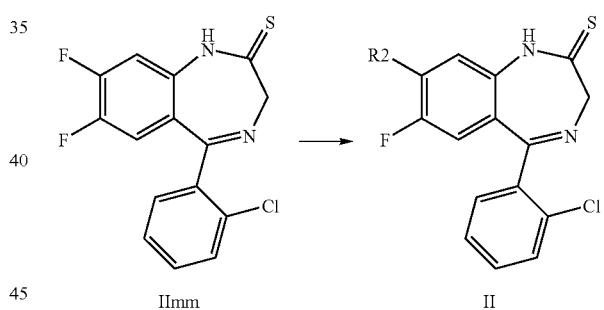

Example 52

Preparation of 5-(2-chlorophenyl)-1,3-dihydro-7-fluoro-8-methoxyethoxy-2H-1,4-benzodiazepin-2-thione (IIf)

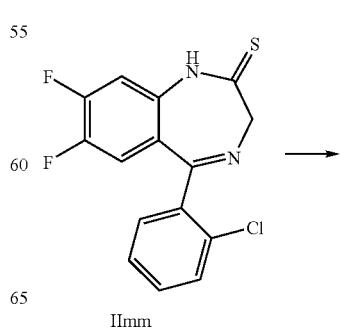

-continued

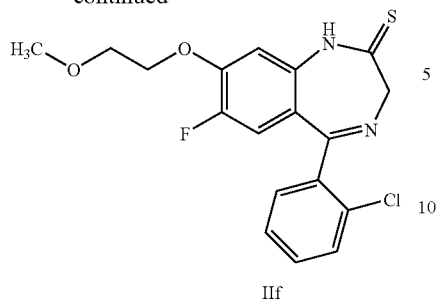

IIf

A mixture of 1.0 g (0.0031 mole) of 5-(2-chlorophenyl)-1,3-dihydro-7,8-difluoro-2H-1,4-benzodiazepin-2-thione (IImm), 0.372 g of sodium hydride and 20 mL of 2-methoxyethanol was heated in a microwave vessel at 120° C. for 30 minutes, cooled and then diluted with ethyl acetate. The mixture was washed successively with water and brine, dried over anhydrous sodium sulfate, filtered and concentrated under reduced pressure. The residue was triturated with ethyl acetate to give 0.74 g of 5-(2-chlorophenyl)-1,3-dihydro-7-fluoro-8-methoxyethoxy-2H-1,4-benzodiazepin-2-thione (IIf) as a white solid, which was then used to prepare 5-(2-chlorophenyl)-1,2-dihydro-7-fluoro-8-methoxyethoxy-3-methyl-pyrazolo[3,4-b][1,4]benzodiazepine (IVf) in accordance with Example 58 without further purification. MH+/Z=379.

Example 53

Preparation of 5-(2-chlorophenyl)-1,3-dihydro-8-ethoxy-7-fluoro-2H-1,4-benzodiazepin-2-thione (IIg)

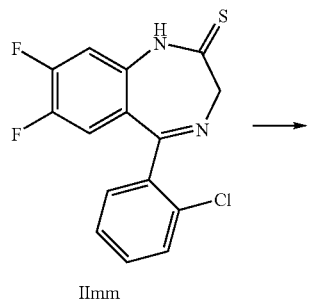

IImm

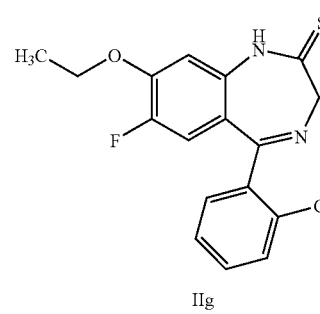

IIg

A mixture of 0.5 g (0.00155 mole) of 5-(2-chlorophenyl)-1,3-dihydro-7,8-difluoro-2H-1,4-benzodiazepin-2-thione (IImm), 10 mL of ethanol and 0.62 g of 60% sodium hydride was heated at reflux for 24 hours. The mixture was cooled, diluted with ethyl acetate and washed successively with water and then brine. The ethyl acetate extract was dried over anhydrous sodium sulfate, filtered and concentrated under reduced pressure to give 0.52 g of 5-(2-chlorophenyl)-1,3-dihydro-8-ethoxy-7-fluoro-2H-1,4-benzodiazepin-2-thione (IIg) as a yellow solid. MH+/Z=349.

Example 54

Preparation of 5-(2-chlorophenyl)-1,3-dihydro-7-fluoro-8-(1-methylethoxy)-2H-1,4-benzodiazepin-2-thione (IIh)

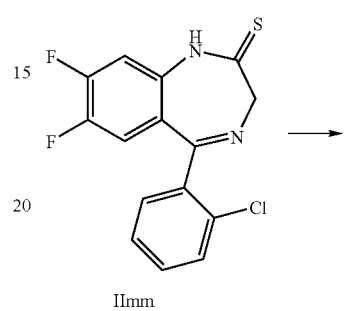

IImm

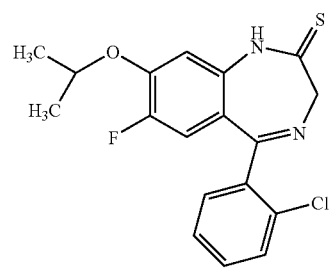

IIh

A mixture of 1.0 g (0.0031 mole) of 5-(2-chlorophenyl)-1,3-dihydro-7,8-difluoro-2H-1,4-benzodiazepin-2-thione (IImm), 10 mL of isopropanol and 0.62 g of 60% sodium hydride was heated at reflux for 5 hours. The mixture was cooled, diluted with ethyl acetate and washed successively with water and then brine. The ethyl acetate extract was dried over anhydrous sodium sulfate, filtered and concentrated under reduced pressure to give 1.2 g of residue which was triturated with hexane and ethyl acetate to give 0.76 g of 5-(2-chlorophenyl)-1,3-dihydro-7-fluoro-8-(1-methylethoxy)-2H-1,4-benzodiazepin-2-thione (IIh) as a white solid. MH+/Z=363.

Preparation of pyrazolobenzodiazepines IV from thiolactams II (scheme 2).

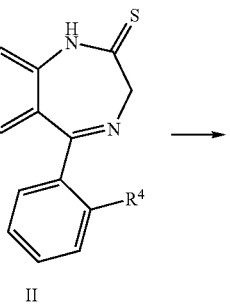

II

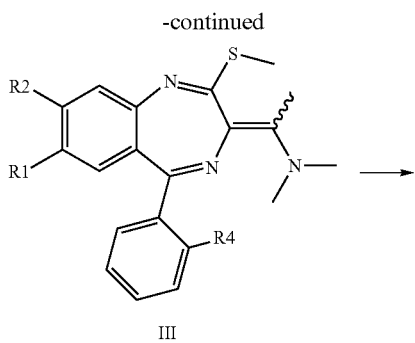

III

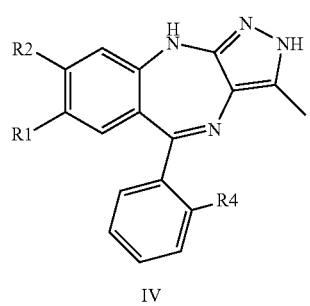

IV

Example 55

Preparation of 7-bromo-5-(2-chlorophenyl)-1,2-dihydro-8-methoxy-3-methyl-pyrazolo[3,4-b][1,4]benzodiazepine (IVd)

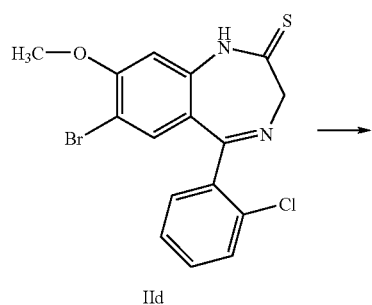

IId

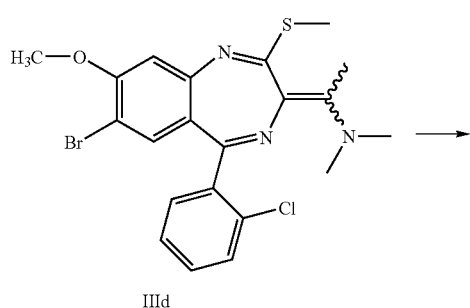

IIId

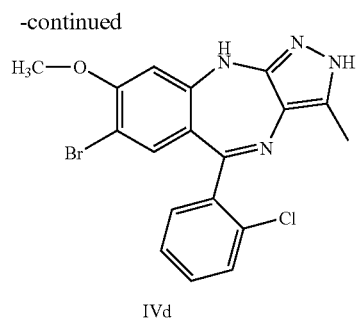

IVd

A mixture of 1.8 g (0.00455 mole) of 7-bromo-5-(2-chlorophenyl)-1,3-dihydro-8-methoxy-2H-1,4-benzodiazepin-2-thione (IId), 2.26 mL of 1,1-dimethoxy-N,N-dimethyl-ethanamine and 20 mL of dimethylformamide was stirred at room temperature for 1.5 hours, then at 110° C. for 5 hours. The mixture was cooled and concentrated under reduced pressure. The crude intermediate, IIId, was stirred with a solution of 0.713 mL of anhydrous hydrazine, 9 mL of methanol and 24 mL of dichloromethane for 26 hours and then partitioned between ethyl acetate and water. The ethyl acetate layer was washed with water, dried over anhydrous sodium sulfate, filtered and concentrated under reduced pressure. Chromatography on silica gel, eluting with ethyl acetate yielded 0.690 g of 7-bromo-5-(2-chlorophenyl)-1,2-dihydro-8-methoxy-3-methyl-pyrazolo[3,4-b][1,4]benzodiazepine (IVd). Recrystallization from dichloromethane provided the crystalline 7-bromo-5-(2-chlorophenyl)-1,2-dihydro-8-methoxy-3-methyl-pyrazolo[3,4-b][1,4]benzodiazepine (IVd), mp 210-211° C. MH+/Z=417.

Example 56

Preparation of 5-(2-chlorophenyl)-1,2-dihydro-7-fluoro-8-methoxy-3-methyl-pyrazolo[3,4-b][1,4]benzodiazepine (IVa)

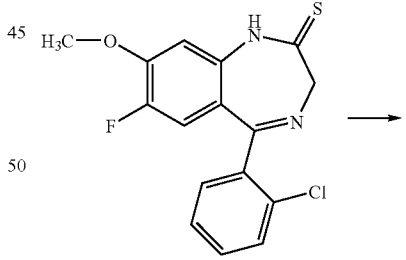

IIa

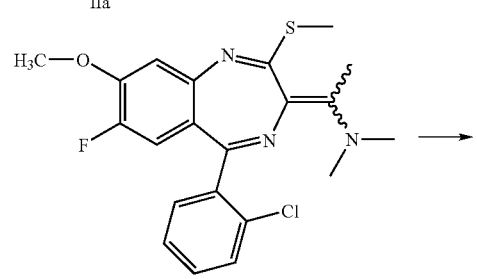

IIIa

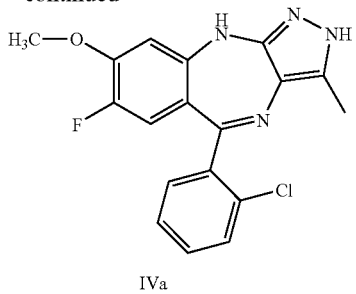

IVa 5-(2-chlorophenyl)-1,2-dihydro-7-fluoro-8-methoxy-3-methyl-pyrazolo[3,4-b][1,4]benzodiazepine (IVa) was prepared by reacting 0.0224 moles of 5-(2-chlorophenyl)-1,3-dihydro-7-fluoro-8-methoxy-2H-1,4-benzodiazepin-2-thione (IIa) with 1,1-dimethoxy-N,N-dimethyl-ethanamine and then hydrazine in a manner analogous to Example 55. MH+/Z=357.

Example 57

Preparation of 5-(2-chlorophenyl)-7-cyano-1,2-dihydro-8-methoxy-3-methyl-pyrazolo[3,4-b][1,4]benzodiazepine (IVb)

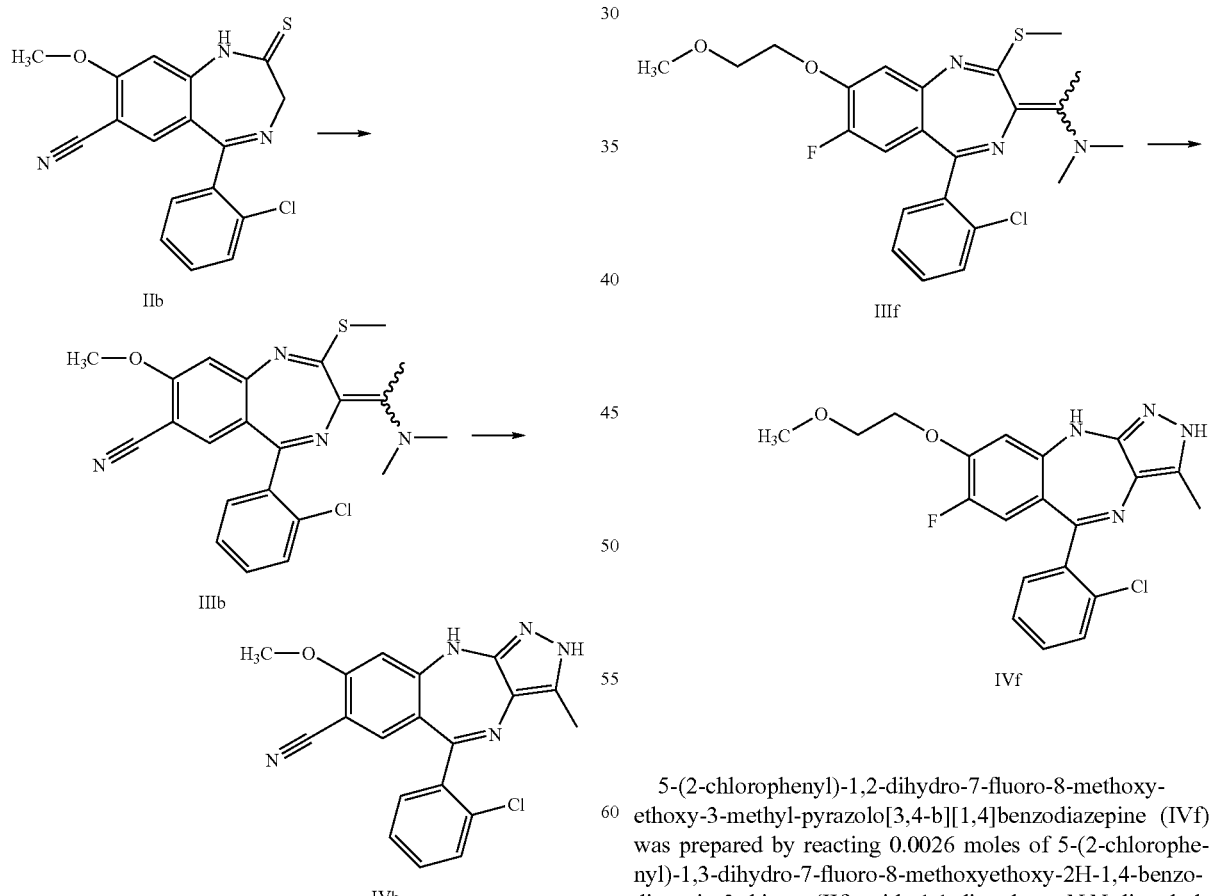

IIb

IIIb

IVb 5-(2-chlorophenyl)-7-cyano-1,2-dihydro-8-methoxy-3-methyl-pyrazolo[3,4-b][1,4]benzodiazepine (IVb) was prepared by reacting 0.0016 moles of 5-(2-chlorophenyl)-7-cyano-1,3-dihydro-8-methoxy-2H-1,4-benzodiazepin-2-thione (IIb) with 1,1-dimethoxy-N,N-dimethyl-ethanamine and then hydrazine in a manner analogous to Example 55. MH+/Z=364.

Example 58

Preparation of 5-(2-chlorophenyl)-1,2-dihydro-7-fluoro-8-methoxyethoxy-3-methyl-pyrazolo[3,4-b][1,4]benzodiazepine (IVf)

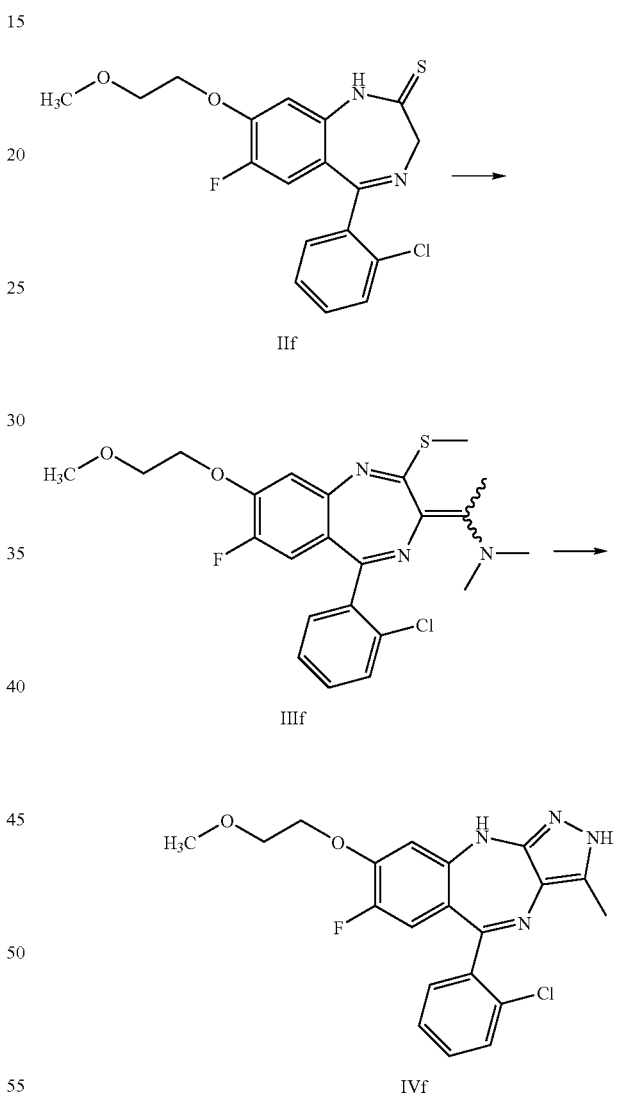

IIf

IIIf

IVf 5-(2-chlorophenyl)-1,2-dihydro-7-fluoro-8-methoxyethoxy-3-methyl-pyrazolo[3,4-b][1,4]benzodiazepine (IVf) was prepared by reacting 0.0026 moles of 5-(2-chlorophenyl)-1,3-dihydro-7-fluoro-8-methoxyethoxy-2H-1,4-benzodiazepin-2-thione (IIf) with 1,1-dimethoxy-N,N-dimethyl-ethanamine and then hydrazine in a manner analogous to Example 55.

MH+/Z=401.

Example 59

Preparation of 5-(2-chlorophenyl)-1,2-dihydro-7-fluoro-8-ethoxy-3-methyl-pyrazolo[3,4-b][1,4]benzodiazepine (IVg)

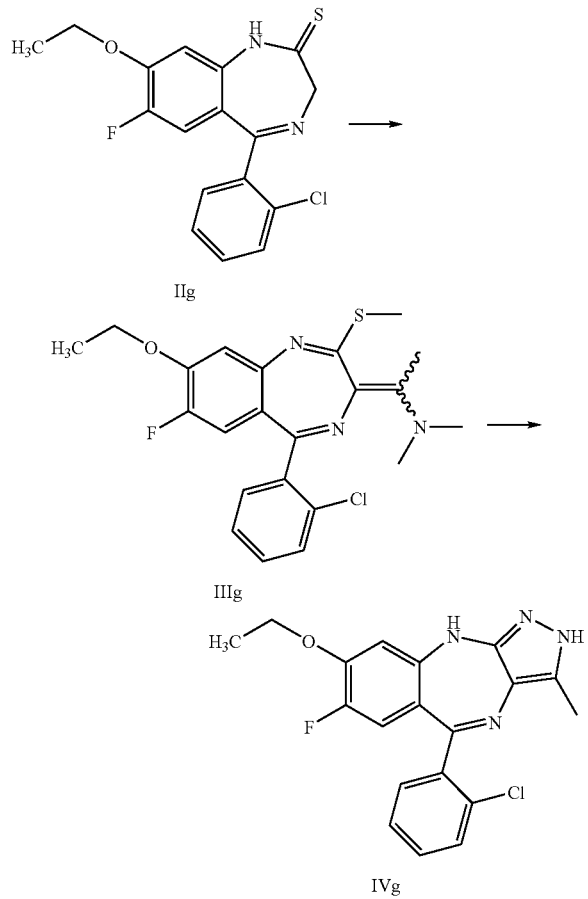

5-(2-chlorophenyl)-1,2-dihydro-7-fluoro-8-ethoxy-3-methyl-pyrazolo[3,4-b][1,4]benzodiazepine (IVg) was prepared by reacting 0.0016 moles of 5-(2-chlorophenyl)-1,3-dihydro-8-ethoxy-7-fluoro-2H-1,4-benzodiazepin-2-thione (IIg) with 1,1-dimethoxy-N,N-dimethyl-ethanamine and then hydrazine in a manner analogous to Example 55. MH+/Z=371.

Example 60

Preparation of 5-(2-chlorophenyl)-1,2-dihydro-7-fluoro-8-(1-methylethoxy)-3-methyl-pyrazolo[3,4-b][1,4]benzodiazepine (IVh)

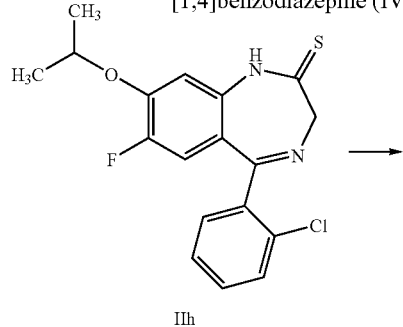

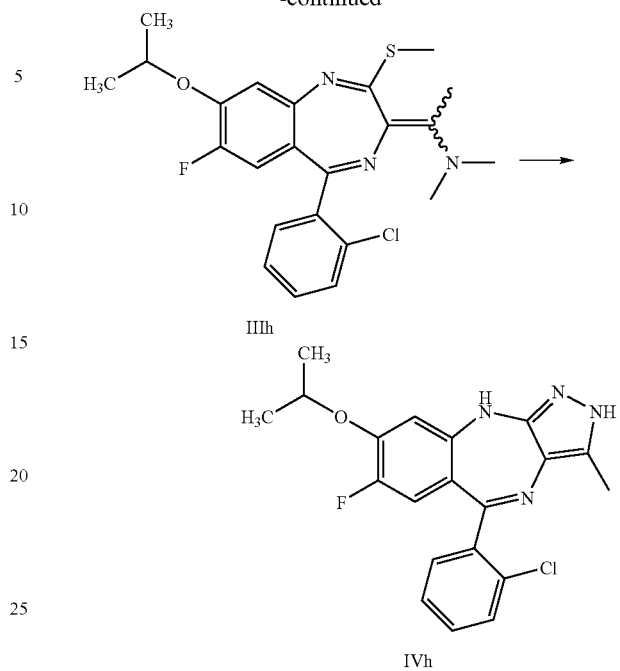

5-(2-chlorophenyl)-1,2-dihydro-7-fluoro-8-(1-methylethoxy)-3-methyl-pyrazolo[3,4-b][1,4]benzodiazepine (IVh) was prepared by reacting 0.00198 moles of 5-(2-chlorophenyl)-1,3-dihydro-7-fluoro-8-(1-methylethoxy)-2H-1,4-benzodiazepin-2-thione (IIh) with 1,1-dimethoxy-N,N-dimethyl-ethanamine and then hydrazine in a manner analogous to Example 55. MH+/Z=385.

Example 61

Preparation of 5-(2-chlorophenyl)-1,2-dihydro-7-fluoro-8-(3-(4-morpholinyl)propoxy)-3-methyl-pyrazolo[3,4-b][1,4]benzodiazepine (IVi)

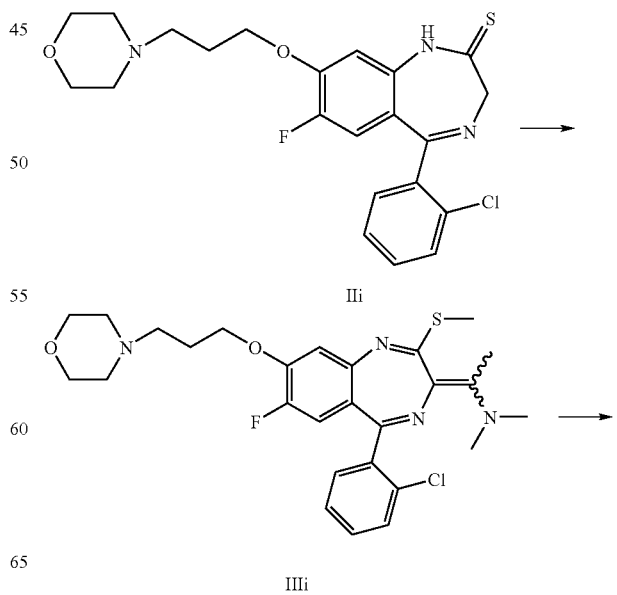

-continued

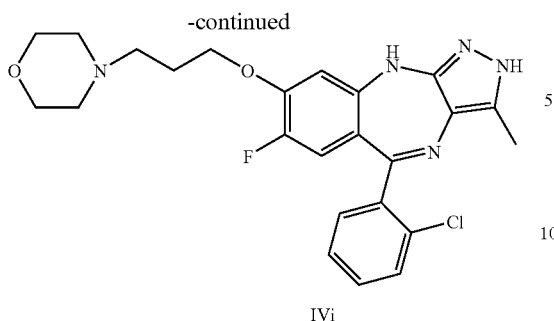

IVi 5-(2-chlorophenyl)-1,2-dihydro-7-fluoro-8-(3-(4-morpholinyl)propoxy)-3-methyl-pyrazolo[3,4-b][1,4]benzodiazepine (IVi) was prepared by reacting 0.0045 moles of 5-(2-chlorophenyl)-1,3-dihydro-7-fluoro-8-(3-(4-morpholinyl)propoxy)-2H-1,4-benzodiazepin-2-thione (thiolactam IIi) with 1,1-dimethoxy-N,N-dimethyl-ethanamine and then hydrazine in a manner analogous to Example 55. MH+/Z=470.

Example 62

Preparation of 7-bromo-5-(2-chlorophenyl)-1,2-dihydro-8-(3-(4-morpholinyl)propoxy)-3-methyl-pyrazolo[3,4-b][1,4]benzodiazepine (IVj)

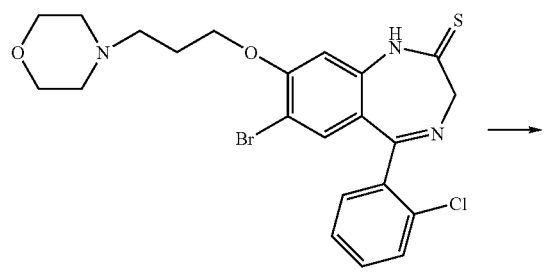

IIj

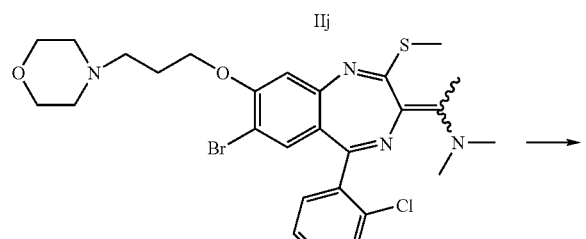

IIIj

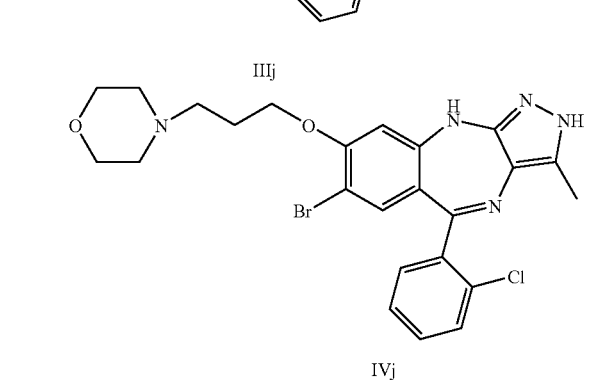

IVj 7-bromo-5-(2-chlorophenyl)-1,2-dihydro-8-(3-(4-morpholinyl)propoxy)-3-methyl-pyrazolo[3,4-b][1,4]benzodiazepine (IVj) was prepared by reacting 0.0011 moles of 7-bromo-5-(2-chlorophenyl)-1,3-dihydro-8-(3-(4-morpholinyl)propoxy)-2H-1,4-benzodiazepin-2-thione (IIj) with 1,1-dimethoxy-N,N-dimethyl-ethanamine and then hydrazine in a manner analogous to Example 55. MH+/Z=530.

Example 63

Preparation of 5-(2-chlorophenyl)-7-cyano-1,2-dihydro-8-(3-(4-morpholinyl)propoxy)-3-methyl-pyrazolo[3,4-b][1,4]benzodiazepine (IVk)

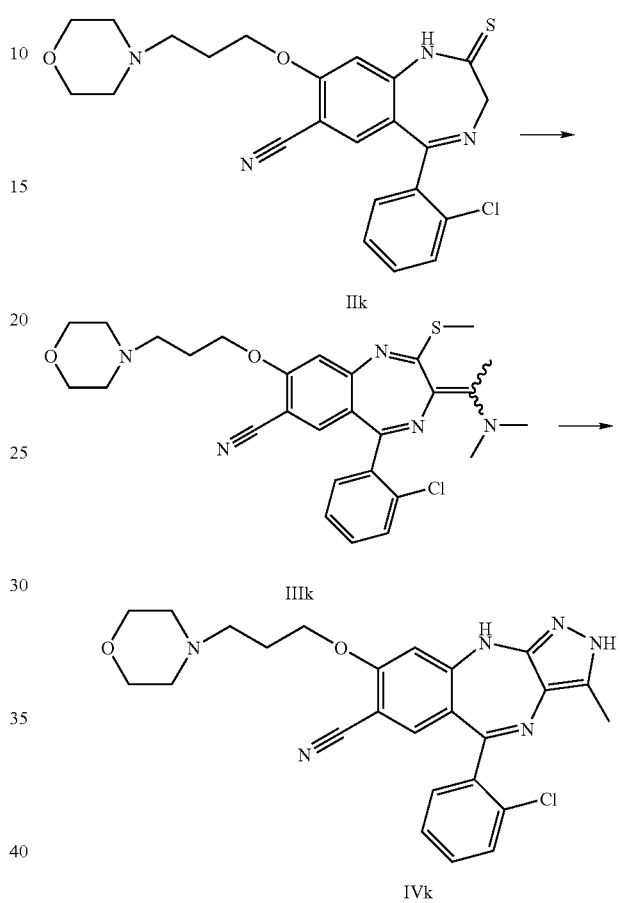

5-(2-chlorophenyl)-7-cyano-1,2-dihydro-8-(3-(4-morpholinyl)propoxy)-3-methyl-pyrazolo[3,4-b][1,4]benzodiazepine (IVk) was prepared by reacting 0.00054 moles of 5-(2-chlorophenyl)-7-cyano-1,3-dihydro-8-(3-(4-morpholinyl)propoxy)-2H-1,4-benzodiazepin-2-thione (thiolactam IIk) with 1,1-dimethoxy-N,N-dimethyl-ethanamine and then hydrazine in a manner analogous to Example 55. MH+/Z=477.

Example 64

Preparation of 5-(2-chlorophenyl)-1,2-dihydro-7-fluoro-8-N,N-dimethylamino-3-methyl-pyrazolo[3,4-b][1,4]benzodiazepine (IVl)

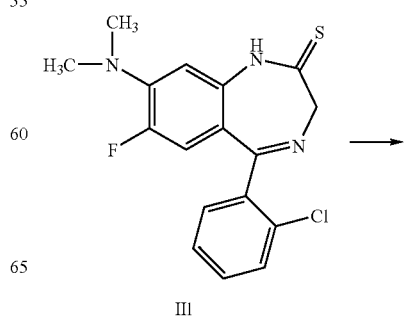

III

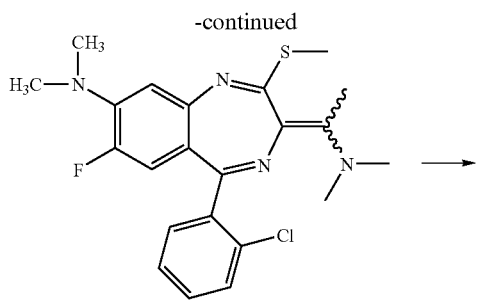

IIIl

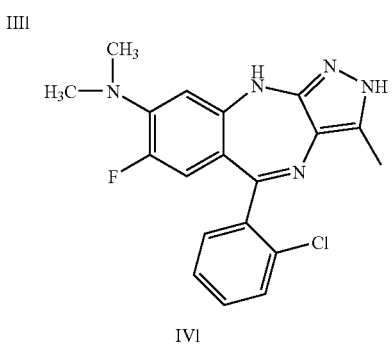

IVl 5-(2-chlorophenyl)-1,2-dihydro-7-fluoro-8-N,N-dimethylamino-3-methyl-pyrazolo[3,4-b][1,4]benzodiazepine (IVl) was prepared by reacting 0.00187 moles of 5-(2-chlorophenyl)-8-N,N-dimethylamino-1,3-dihydro-7-fluoro-2H-1,4-benzodiazepin-2-thione (III) with 1,1-dimethoxy-N,N-dimethyl-ethanamine and then hydrazine in a manner analogous to Example 55.

MH+/Z=370.

Example 65

Preparation of 5-(2-chlorophenyl)-7-cyano-1,2-dihydro-8-methoxyethoxy-3-methyl-pyrazolo[3,4-b][1,4] benzodiazepine (IVm)

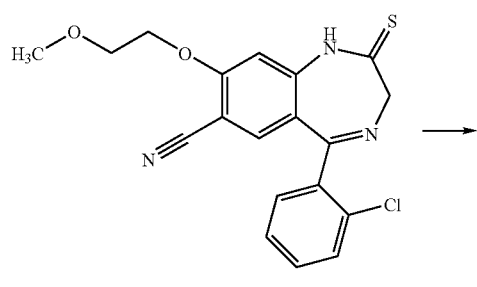

IIm

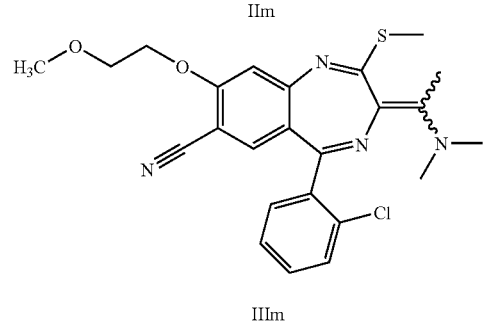

IIIm

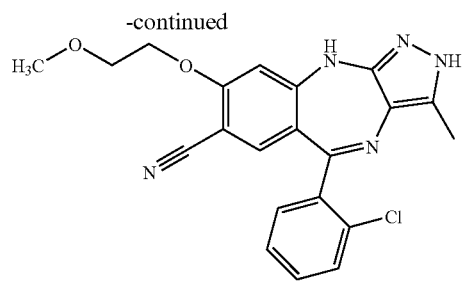

IVm 5-(2-chlorophenyl)-7-cyano-1,2-dihydro-8-methoxyethoxy-3-methyl-pyrazolo[3,4-b][1,4]benzodiazepine (IVm) was prepared by reacting 0.00048 moles of 5-(2-chlorophenyl)-7-cyano-1,3-dihydro-8-methoxyethoxy-2H-1,4-benzodiazepin-2-thione (IIm) with 1,1-dimethoxy-N,N-dimethyl-ethanamine and then hydrazine in a manner analogous to Example 55.

MH+/Z=408.

Example 66

Preparation of 5-(2-chlorophenyl)-7-cyano-1,2-dihydro-8-(2-(2-methoxyethoxy)ethoxy)-3-methyl-pyrazolo[3,4-b][1,4]benzodiazepine (IVn)

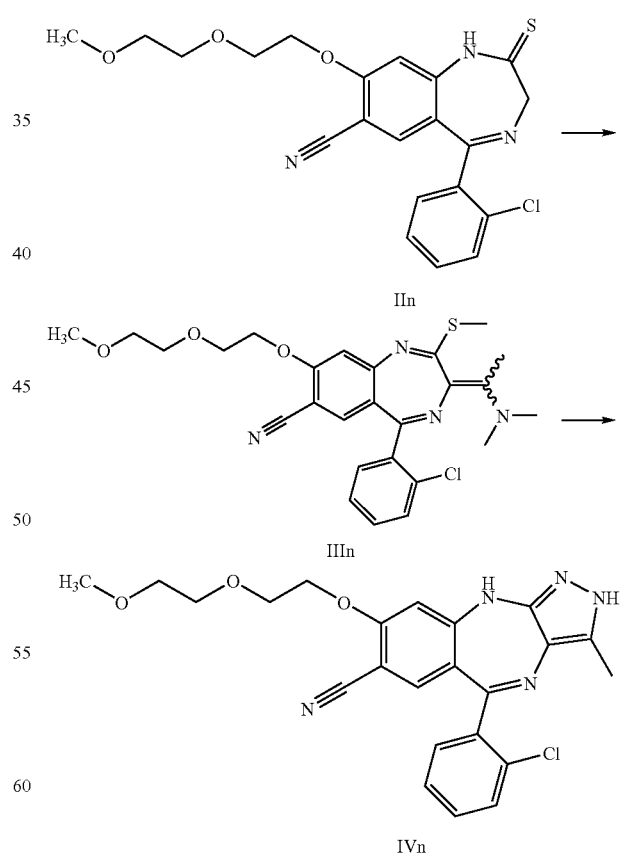

5-(2-chlorophenyl)-7-cyano-1,2-dihydro-8-(2-(2-methoxyethoxy)ethoxy)-3-methyl-pyrazolo[3,4-b][1,4]benzodiazepine (IVn) was prepared by reacting 0.00067 moles of 5-(2-chlorophenyl)-7-cyano-1,3-dihydro-8-(2-(2-methoxyethoxy)ethoxy)-2H-1,4-benzodiazepin-2-thione (IIn) with 1,1-dimethoxy-N,N-dimethyl-ethanamine and then hydrazine in a manner analogous to Example 55. MH+/Z=452.

Example 67

Preparation of 5-(2-chlorophenyl)-7-cyano-1,2-dihydro-8-(2-(4-methyl-1-piperazinyl)ethoxy)-3-methyl-pyrazolo[3,4-b][1,4]benzodiazepine (IVt)

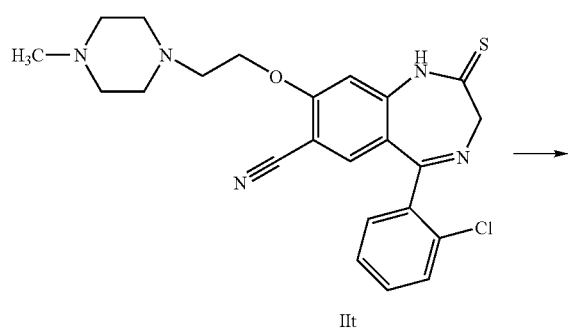

IIt

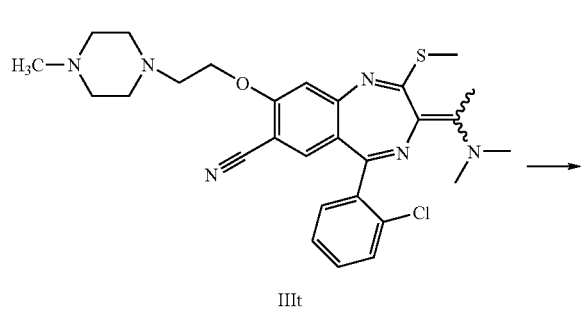

IIIt

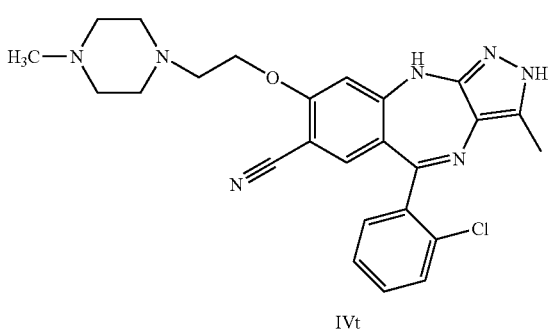

IVt 5-(2-chlorophenyl)-7-cyano-1,2-dihydro-8-(2-(4-methyl-1-piperazinyl)ethoxy)-3-methyl-pyrazolo[3,4-b][1,4]benzodiazepine (IVt) was prepared by reacting 0.00062 moles of 5-(2-chlorophenyl)-7-cyano-1,3-dihydro-8-(2-((2-(4-methyl-1-piperazinyl)ethoxy))-2H-1,4-benzodiazepin-2-thione (IIt) with 1,1-dimethoxy-N,N-dimethyl-ethanamine and then hydrazine in a manner analogous to Example 55. MH+/Z=476.

Example 68

Preparation of 5-(2-chlorophenyl)-7-cyano-1,2-dihydro-8-(2-((2-methoxyethyl)methylamino)-ethoxy)-3-methyl-pyrazolo[3,4-b][1,4]benzodiazepine (IVv)

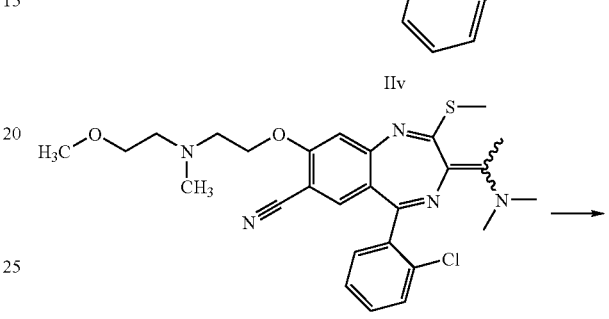

IIv

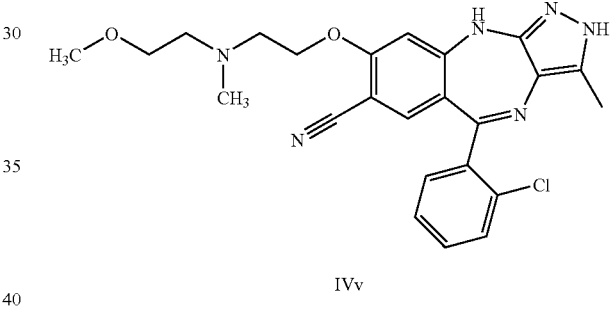

IIIv

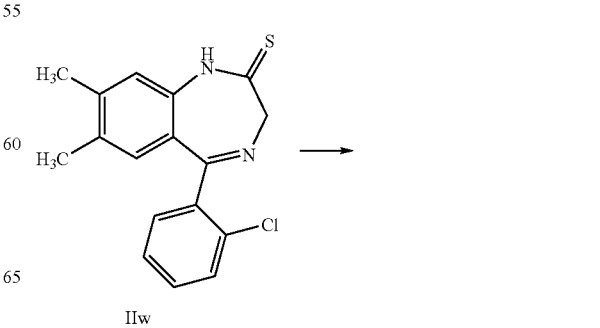

IVv 5-(2-chlorophenyl)-7-cyano-1,2-dihydro-8-(2-((2-methoxyethyl)methylamino)-ethoxy)-3-methyl-pyrazolo[3,4-b][1,4]benzodiazepine (IVv) was prepared by reacting 0.0005 moles of 5-(2-chlorophenyl)-7-cyano-1,3-dihydro-8-(2-((2-methoxyethyl)methylamino)-ethoxy)-2H-1,4-benzodiazepin-2-thione (IIv) with 1,1-dimethoxy-N,N-dimethyl-ethanamine and then hydrazine in a manner analogous to Example 55. MH+/Z=465.

Example 69

Preparation of 5-(2-chlorophenyl)-1,2-dihydro-3,7,8-trimethyl-pyrazolo[3,4-b][1,4]benzodiazepine (IVw)

IIw

-continued

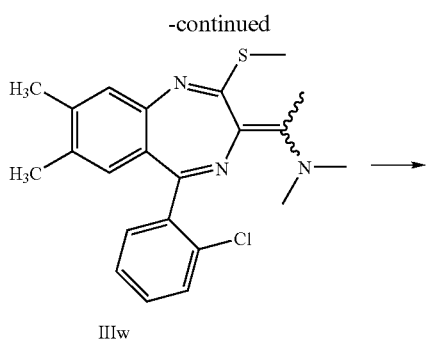

IIIw

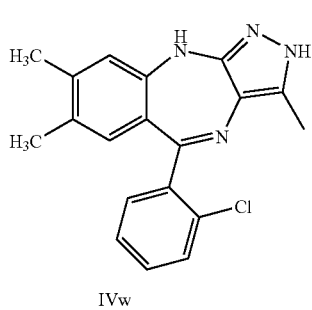

IVw 5-(2-chlorophenyl)-1,2-dihydro-3,7,8-trimethyl-pyrazolo[3,4-b][1,4]benzodiazepine (IVw) was prepared by reacting 0.0005 moles of 5-(2-chlorophenyl)-1,3-dihydro-7,8-dimethyl-2H-1,4-benzodiazepin-2-thione (IIw) with 1,1-dimethoxy-N,N-dimethyl-ethanamine and then hydrazine in a manner analogous to Example 55. MH+/Z=337.

Example 70

Preparation of 5-(2-chlorophenyl)-1,2-dihydro-3,7-dimethyl-8-methoxy-pyrazolo[3,4-b][1,4]benzodiazepine (IVz)

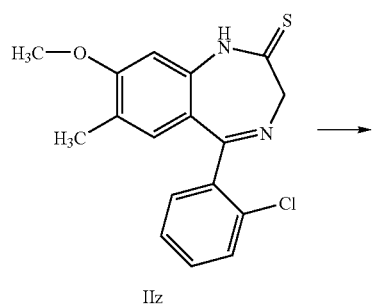

IIz

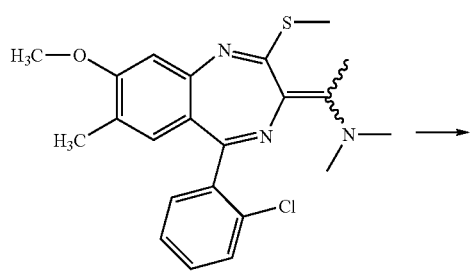

IIIz

-continued

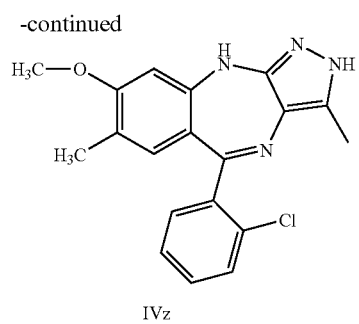

IVz 5-(2-chlorophenyl)-1,2-dihydro-3,7-dimethyl-8-methoxy-pyrazolo[3,4-b][1,4]benzodiazepine (IVz) was prepared by reacting 0.0005 moles of 5-(2-chlorophenyl)-1,3-dihydro-8-methoxy-7-methyl-2H-1,4-benzodiazepin-2-thione (IIz) with 1,1-dimethoxy-N,N-dimethyl-ethanamine and then hydrazine in a manner analogous to Example 55. MH+/Z=353.

Preparation of pyrazolobenzodiazepine IV from lactam I (scheme 2)

Preparation of pyrazolobenzodiazepine IV from lactam I (scheme 2)

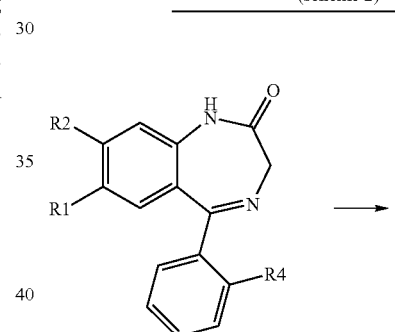

I

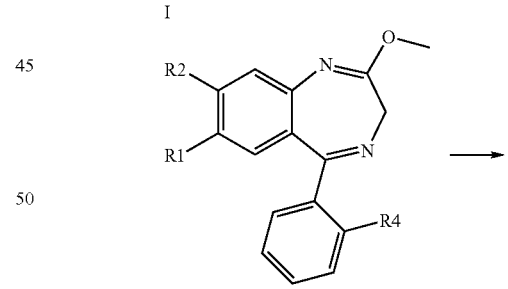

V

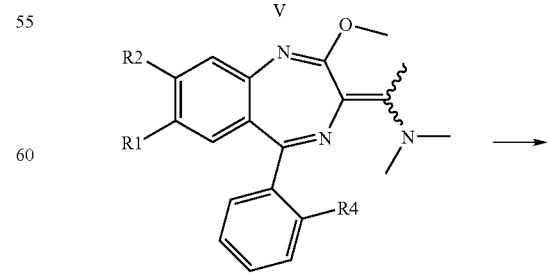

VI

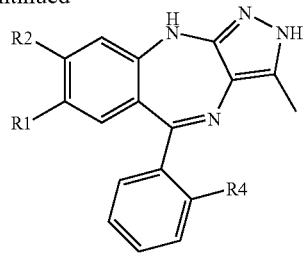

IV

Example 71

Preparation of 5-(2-chlorophenyl)-1,2-dihydro-7-fluoro-8-methoxy-3-methyl-pyrazolo[3,4-b][1,4]benzodiazepine (IVa)

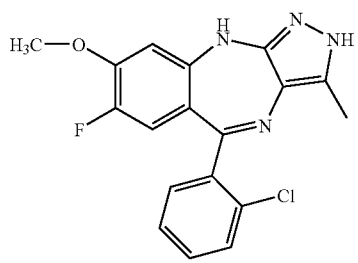

IVa

To a mixture of 3.0 g (0.0094 mole) of 5-(2-chlorophenyl)-1,3-dihydro-7-fluoro-8-methoxy-2H-1,4-benzodiazepin-2-one (Ia), 11.8 mL of ethyl diisopropyl amine, 4.62 g of 1,2,4-triazole and 45 mL of tetrahydrofuran at 0° C., was added 1.575 mL of phosphorous oxychloride. After 20 minutes, the cooling bath was removed, and the mixture was stirred at room temperature for another 60 minutes. Then, 17 mL of 4.37 M sodium methoxide in methanol solution was added to the reaction mixture. After stirring for 2 hours, another 5 mL of sodium methoxide solution was added, and the mixture stirred overnight. The mixture was then partitioned between ethyl acetate and water. The ethyl acetate layer was washed successively with water and brine, dried over anhydrous sodium sulfate, filtered and concentrated under reduced pressure to yield 3.2 g of 5-(2-chlorophenyl)-7-fluoro-2,8-dimethoxy-3H-1,4-benzodiazepine (intermediate Va), which was of sufficient purity to use in the next step.

A mixture of 3.0 g of intermediate Va prepared above, 30 mL of dimethylformamide and 13.2 mL of 1,1-dimethoxy-N,N-dimethyl-ethanamine was heated at 110° C. for 24 hours and then cooled. The mixture was concentrated under reduced pressure to give the crude intermediate VIa which was used directly in the next step. The residue was dissolved in 48 mL of dichloromethane and 15 mL of methanol, and reacted with 1.41 mL of anhydrous hydrazine for 30 hours. The mixture was partitioned between water and ethyl acetate. The aqueous phase was reextracted with ethyl acetate and the ethyl acetate layers washed with water, dried over anhydrous sodium sulfate, filtered and concentrated under reduced pressure. The residue was chromatographed on silica gel, eluting with ethyl acetate-hexane (8:1) to give 2.05 g of 5-(2-chlorophenyl)-1,2-dihydro-7-fluoro-8-methoxy-3-methyl-pyrazolo[3,4-b][1,4]benzodiazepine (IVa). The material was crystallized from hexane-dichloromethane to yield IVa as a yellow solid, mp 217-218° C. MH+/Z=357.

Preparation of pyrazolobenzodiazepines IV from the aminobenzophenones X with pyrazole XIII (scheme 4).

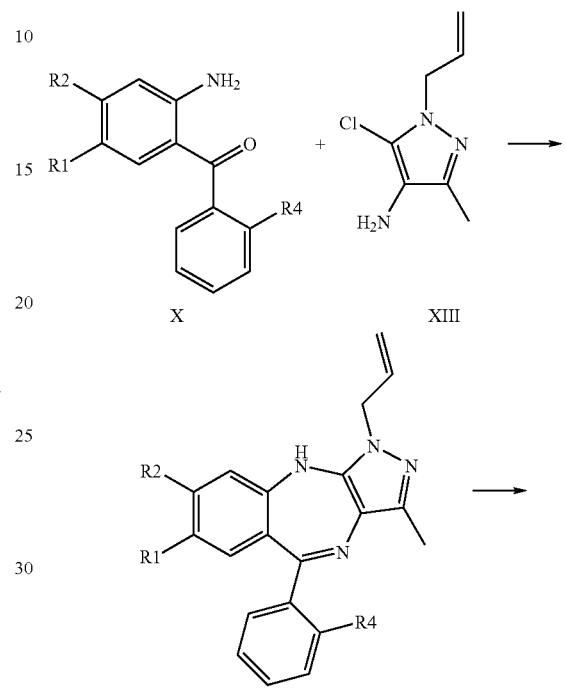

Example 72

Preparation of 5-(2-chlorophenyl)-1,2-dihydro-3,7,8-trimethyl-pyrazolo[3,4-b][1,4]benzodiazepine (IVw)$_{IVw}$

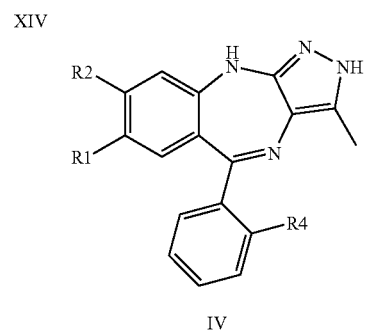

A mixture of 3.0 g (0.0116 mole) of (2-amino-4,5-dimethylphenyl)-(2-chlorophenyl)-methanone (Xw), 2.0 g (0.0116 mole) of 4-amino-5-chloro-3-methyl-1-(2-propenyl)-1H-pyrazole (XIII), 2.21 g (0.0116 mole) of p-toluenesulfonic acid monohydrate and 40 mL of isopropanol was heated in a sealed tube at 170° C. for 90 minutes. The mixture was concentrated under reduced pressure, and the residue was diluted with ethyl acetate and then washed twice with saturated sodium bicarbonate solution. The aqueous washes were reextracted with ethyl acetate, and the combined ethyl acetate layers were dried over anhydrous sodium sulfate, filtered and concentrated under reduced pressure. Trituration of the residue with hexane gave the intermediate 5-(2-chlorophenyl)-1,2-dihydro-3,7,8-trimethyl-1-(2-propenyl)-pyrazolo[3,4-b][1,4]benzodiazepine (XIVw), as a yellow solid. Purification of the filtrates by silica gel chromatography, eluting with ethyl acetate-dichloromethane (1:1) provided additional XIVw and was combined with the material obtained above for a total yield of 2.7 g of XIVw as a yellow solid, which was used directly in the next step.

To a solution of 2.7 g (0.00716 mole) of 5-(2-chlorophenyl)-1,2-dihydro-3,7,8-trimethyl-1-(2-propenyl)-pyrazolo[3,4-b][1,4]benzodiazepine (XIVw), 0.155 g (0.00029 mole) of 1,3-bis(diphenylphosphino)propane nickel (II) chloride and 140 mL of anhydrous tetrahydrofuran at −40° C. was added 43 mL of 1M diisobutylaluminum hydride in toluene. The mixture was stirred at 0° C. for 6 hours and then quenched by the careful addition of ice water. The mixture was extracted twice with ethyl acetate. The combined ethyl acetate extracts were dried over anhydrous sodium sulfate, filtered and concentrated under reduced pressure. The residue was purified by silica gel chromatography, eluting with ethyl acetate-dichloromethane (1:1) to give 1.5 g of 5-(2-chlorophenyl)-1,2-dihydro-3,7,8-trimethyl-pyrazolo[3,4-b][1,4]benzodiazepine (IVw) as an orange solid. MH+/Z=337.

Example 73

Preparation of 5-(2-chlorophenyl)-1,2-dihydro-7-fluoro-8-methoxy-3-methyl-pyrazolo[3,4-b][1,4]benzodiazepine (IVa)

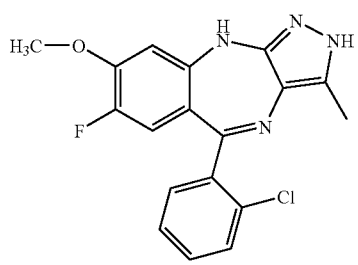

IVa 5-(2-chlorophenyl)-1,2-dihydro-7-fluoro-8-methoxy-3-methyl-pyrazolo[3,4-b][1,4]benzodiazepine (IVa) was prepared by reacting 0.0014 moles of (2-amino-5-fluoro-4-methoxyphenyl)(2-chlorophenyl)-methanone (Xa) with 4-amino-5-chloro-3-methyl-1-(2-propenyl)-1H-pyrazole (XIII), and subsequent dealkylation of the intermediate, 5-(2-chlorophenyl)-1,2-dihydro-7-fluoro-8-methoxy-3-methyl-1-(2-propenyl)-pyrazolo[3,4-b][1,4]benzodiazepine (XIVa) with diisobutylaluminum hydride in a manner analogous to Example 72. MH+/Z=357.

Example 74

Preparation of 5-(2-chlorophenyl)-1,2-dihydro-7,8-dimethoxy-3-methyl-pyrazolo[3,4-b][1,4]benzodiazepine (IVx)

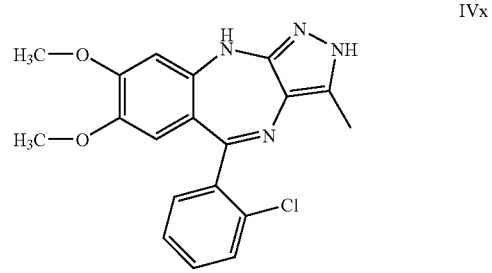

IVx 5-(2-chlorophenyl)-1,2-dihydro-7,8-dimethoxy-3-methyl-pyrazolo[3,4-b][1,4]benzodiazepine (IVx) was prepared by reacting 0.00093 moles of (2-amino-4,5-dimethoxyphenyl)(2-chlorophenyl)-methanone (Xx) with 4-amino-5-chloro-3-methyl-1-(2-propenyl)-1H-pyrazole (XIII), and subsequent dealkylation of the intermediate, 5-(2-chlorophenyl)-1,2-dihydro-7,8-dimethoxy-3-methyl-1-(2-propenyl)-pyrazolo[3,4-b][1,4]benzodiazepine (XIVx) with diisobutylaluminum hydride in a manner analogous to Example 72. MH+/Z=369.

Example 75

Preparation of 8-chloro-5-(2-chlorophenyl)-1,2-dihydro-7-methoxy-3-methyl-pyrazolo[3,4-b][1,4]benzodiazepine (IVy)

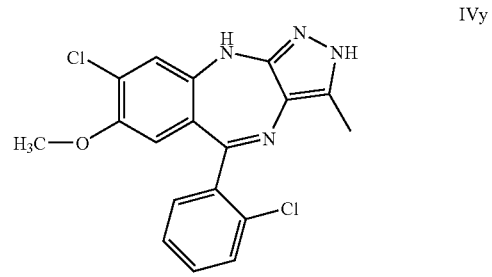

IVy 8-chloro-5-(2-chlorophenyl)-1,2-dihydro-7-methoxy-3-methyl-pyrazolo[3,4-b][1,4]benzodiazepine (IVy) was prepared by reacting 0.0012 moles of (2-amino-4-chloro-5-methoxyphenyl)(2-chlorophenyl)-methanone (Xy) with 4-amino-5-chloro-3-methyl-1-(2-propenyl)-1H-pyrazole (XIII), and subsequent dealkylation of the intermediate, 8-chloro-5-(2-chlorophenyl)-1,2-dihydro-7-methoxy-3-methyl-1-(2-propenyl)-pyrazolo[3,4-b][1,4]benzodiazepine (XIVy) with diisobutylaluminum hydride in a manner analogous to Example 72. MH+/Z=373.

Example 76

Preparation of 5-(2-chlorophenyl)-1,2-dihydro-8-methoxy-3,7-dimethyl-pyrazolo[3,4-b][1,4]benzodiazepine (IVz)

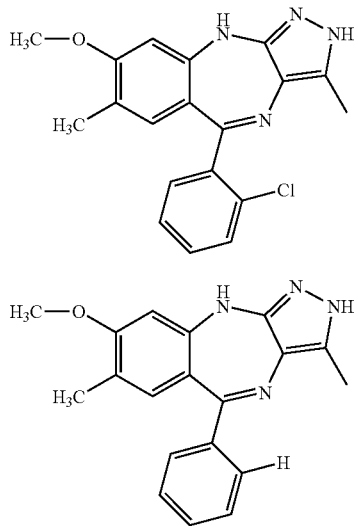

5-(2-chlorophenyl)-1,2-dihydro-8-methoxy-3,7-dimethyl-pyrazolo[3,4-b][1,4]benzodiazepine (IVz) was prepared by reacting 0.0012 moles of (2-amino-4-methoxy-5-methylphenyl)-(2-chlorophenyl)-methanone (Xz) with 4-amino-5-chloro-3-methyl-1-(2-propenyl)-1H-pyrazole (XIII), and subsequent dealkylation of the intermediate, 5-(2-chlorophenyl)-1,2-dihydro-8-methoxy-3,7-dimethyl-1-(2-propenyl)-pyrazolo[3,4-b][1,4]benzodiazepine (XIVz) with diisobutylaluminum hydride in a manner analogous to Example 72. MH+/Z=353.

In addition, 0.4% of 1,2-dihydro-3,7-dimethyl-8-methoxy-5-phenyl-pyrazolo[3,4-b][1,4]benzodiazepine (IVe) was also isolated from the dealkylation reaction. MH+/Z=319.

Example 77

Preparation of 1,2-dihydro-7,8-dimethoxy-5-(2-methoxyphenyl)-3-methyl-pyrazolo[3,4-b][1,4]benzodiazepine (IVaa)

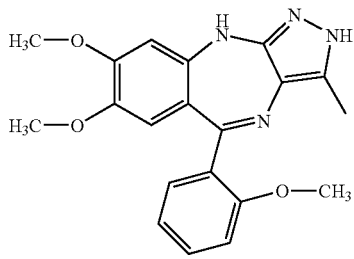

1,2-dihydro-7,8-dimethoxy-5-(2-methoxyphenyl)-3-methyl-pyrazolo[3,4-b][1,4]benzodiazepine (IVaa) was prepared by reacting 0.0023 moles of (2-amino-4,5-dimethoxyphenyl)-(2-methoxyphenyl)-methanone (Xaa) with 4-amino-5-chloro-3-methyl-1-(2-propenyl)-1H-pyrazole (XIII), and subsequent dealkylation of the intermediate, 1,2-dihydro-7,8-dimethoxy-5-(2-methoxyphenyl)-3-methyl-1-(2-propenyl)-pyrazolo[3,4-b][1,4]benzodiazepine (XIVaa) with diisobutylaluminum hydride in a manner analogous to Example 72. MH+/Z=365.

Example 78

Preparation of 5-(2-chlorophenyl)-8,10-dihydro-7-methyl-1,3-dioxolo[4,5-h]pyrazolo[3,4-b][1,4]benzodiazepine (IVbb)

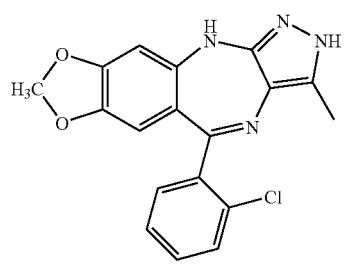

b 5-(2-chlorophenyl)-8,10-dihydro-7-methyl-1,3-dioxolo[4,5-h]pyrazolo[3,4-b][1,4]benzodiazepine (IVbb) was prepared by reacting 0.0023 moles of (6-amino-1,3-benzodioxol-5-yl)-(2-chlorophenyl)-methanone (Xbb) with 4-amino-5-chloro-3-methyl-1-(2-propenyl)-1H-pyrazole (XIII), and subsequent dealkylation of the intermediate, 5-(2-chlorophenyl)-8,10-dihydro-7-methyl-1,3-dioxolo-1-(2-propenyl)-[4,5-h]pyrazolo[3,4-b][1,4]benzodiazepine (XIVbb) with diisobutylaluminum hydride in a manner analogous to Example 72. MH+/Z=353.

Example 79

Preparation of 7-chloro-5-(2-chlorophenyl)-1,2-dihydro-8-methoxy-3-methyl-pyrazolo[3,4-b][1,4]benzodiazepine (IVcc)

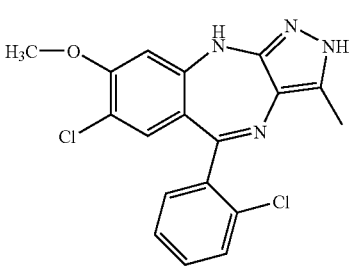

7-chloro-5-(2-chlorophenyl)-1,2-dihydro-8-methoxy-3-methyl-pyrazolo[3,4-b][1,4]benzodiazepine (IVcc) was prepared by reacting 0.0023 moles of (2-amino-5-chloro-4-methoxyphenyl)-(2-chlorophenyl)-methanone (Xcc) with 4-amino-5-chloro-3-methyl-1-(2-propenyl)-1H-pyrazole (XIII), and subsequent dealkylation of the intermediate, 7-chloro-5-(2-chlorophenyl)-1,2-dihydro-8-methoxy-3-methyl-1-(2-propenyl)-pyrazolo[3,4-b][1,4]benzodiazepine (XIVcc) with diisobutylaluminum hydride in a manner analogous to Example 72. MH+/Z=373.

Example 80

Preparation of 5-(2-chlorophenyl)-1,2-dihydro-8-fluoro-7-methoxy-3-methyl-pyrazolo[3,4-b][1,4]benzodiazepine (IVdd)

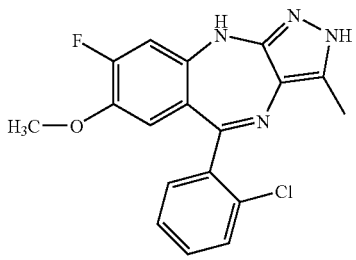

IVdd 5-(2-chlorophenyl)-1,2-dihydro-8-fluoro-7-methoxy-3-methyl-pyrazolo[3,4-b][1,4]benzodiazepine (IVdd) was prepared by reacting 0.0023 moles of (2-amino-4-fluoro-5-methoxyphenyl)-(2-chlorophenyl)-methanone (Xdd) with 4-amino-5-chloro-3-methyl-1-(2-propenyl)-1 H-pyrazole (XIII), and subsequent dealkylation of the intermediate, 5-(2-chlorophenyl)-1,2-dihydro-8-fluoro-7-methoxy-3-methyl-1-(2-propenyl)-pyrazolo[3,4-b][1,4]benzodiazepine (XIVdd) with diisobutylaluminum hydride in a manner analogous to Example 72. MH+/Z=357.

Example 81

Preparation of 5-(2-chlorophenyl)-1,2-dihydro-7-methoxy-3-methyl-8-trifluoromethyl-pyrazolo[3,4-b][1,4]benzodiazepine (IVee)

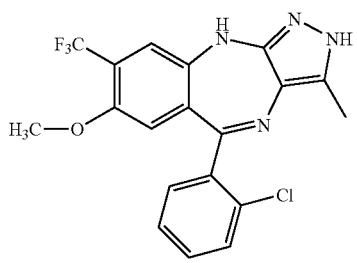

IVee 5-(2-chlorophenyl)-1,2-dihydro-7-methoxy-3-methyl-8-trifluoromethyl-pyrazolo[3,4-b][1,4]benzodiazepine (IVee) was prepared by reacting 0.0023 moles of (2-amino-5-methoxy-4-trifluoromethylphenyl)-(2-chlorophenyl)-methanone (Xee) with 4-amino-5-chloro-3-methyl-1-(2-propenyl)-1H-pyrazole (XIII), and subsequent dealkylation of the intermediate, 5-(2-chlorophenyl)-1,2-dihydro-7-methoxy-3-methyl-1-(2-propenyl)-8-trifluoromethyl-pyrazolo[3,4-b][1,4]benzodiazepine (XIVee) with diisobutylaluminum hydride in a manner analogous to Example 72. MH+/Z=407.

Example 82

Preparation of 5-(2-chlorophenyl)-1,2-dihydro-7-methoxy-3-methyl-8-phenyl-pyrazolo[3,4-b][1,4]benzodiazepine (IVff)

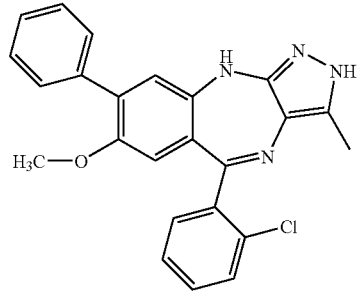

IVff 5-(2-chlorophenyl)-1,2-dihydro-7-methoxy-3-methyl-8-phenyl-pyrazolo[3,4-b][1,4]benzodiazepine (IVff) was prepared by reacting 0.0023 moles of (2-amino-5-methoxy-4-phenylphenyl)-(2-chlorophenyl)-methanone (Xff) with 4-amino-5-chloro-3-methyl-1-(2-propenyl)-1H-pyrazole (XIII), and subsequent dealkylation of the intermediate, 5-(2-chlorophenyl)-1,2-dihydro-7-methoxy-3-methyl-8-phenyl-1-(2-propenyl)-pyrazolo[3,4-b][1,4]benzodiazepine (XIVff) with diisobutylaluminum hydride in a manner analogous to Example 72. MH+/Z=415.

Example 83

Preparation of 5-(2-chlorophenyl)-1,2-dihydro-7-methoxy-8-methoxyethoxy-3-methyl-pyrazolo[3,4-b][1,4]benzodiazepine (IVgg)

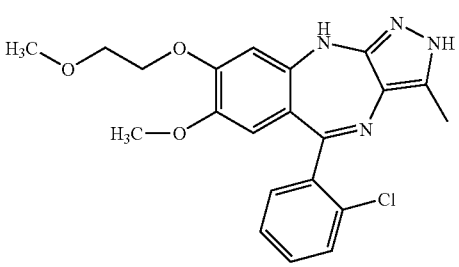

IVgg 5-(2-chlorophenyl)-1,2-dihydro-7-methoxy-8-methoxyethoxy-3-methyl-pyrazolo[3,4-b][1,4]benzodiazepine (IVgg) was prepared by reacting 0.0023 moles of (2-amino-5-methoxy-4-(2-methoxyethoxy)phenyl)-(2-chlorophenyl)-methanone (Xgg) with 4-amino-5-chloro-3-methyl-1-(2-propenyl)-1H-pyrazole (XIII), and subsequent dealkylation of the intermediate, 5-(2-chlorophenyl)-1,2-dihydro-7-methoxy-8-methoxyethoxy-3-methyl-1-(2-propenyl)-pyrazolo[3,4-b][1,4]benzodiazepine (XIVgg) with diisobutylaluminum hydride in a manner analogous to Example 72. MH+/Z=413.

Example 84

Preparation of 8-chloro-5-(2-chlorophenyl)-1,2-dihydro-3,7-dimethyl-pyrazolo[3,4-b][1,4]benzodiazepine (IVhh)

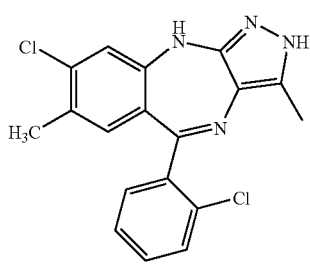

IVhh 8-chloro-5-(2-chlorophenyl)-1,2-dihydro-3,7-dimethyl-pyrazolo[3,4-b][1,4]benzodiazepine (IVhh) was prepared by reacting 0.0023 moles of (2-amino-4-chloro-5-methylphenyl)-(2-chlorophenyl)-methanone (Xhh) with 4-amino-5-chloro-3-methyl-1-(2-propenyl)-1H-pyrazole (XIII), and subsequent dealkylation of the intermediate, 8-chloro-5-(2-chlorophenyl)-1,2-dihydro-3,7-dimethyl-1-(2-propenyl)-pyrazolo[3,4-b][1,4]benzodiazepine (XIVhh) with diisobutylaluminum hydride in a manner analogous to Example 72. MH+/Z=357.

Example 85

Preparation of 5-(2-chlorophenyl)-1,2-dihydro-7-methoxy-8-(1-methylethoxy)-3-methyl-pyrazolo[3,4-b][1,4]benzodiazepine (IVii)

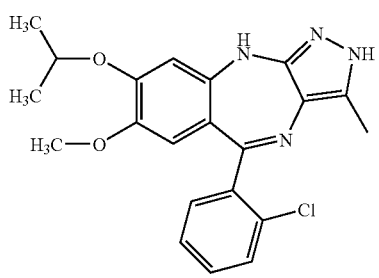

IVii 5-(2-chlorophenyl)-1,2-dihydro-7-methoxy-8-(1-methylethoxy)-3-methyl-pyrazolo[3,4-b][1,4]benzodiazepine (IVii) was prepared by reacting 0.0023 moles of (2-amino-5-methoxy-4-(1-methylethoxy)phenyl)-(2-chlorophenyl)-methanone (Xii) with 4-amino-5-chloro-3-methyl-1-(2-propenyl)-1H-pyrazole (XIII), and subsequent dealkylation of the intermediate, 5-(2-chlorophenyl)-1,2-dihydro-7-methoxy-8-(1-methylethoxy)-3-methyl-1-(2-propenyl)-pyrazolo[3,4-b][1,4]benzodiazepine (XIVii) with diisobutylaluminum hydride in a manner analogous to Example 72. MH+/Z=397.

Example 86

Preparation of 5-(2-chlorophenyl)-1,2-dihydro-8-methoxy-7-(1-methylethoxy)-3-methyl-pyrazolo[3,4-b][1,4]benzodiazepine (IVjj)

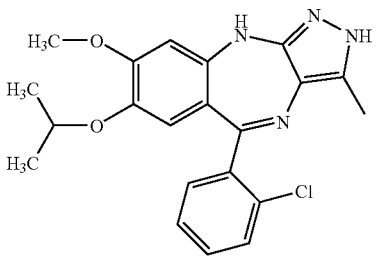

IVjj 5-(2-chlorophenyl)-1,2-dihydro-8-methoxy-7-(1-methylethoxy)-3-methyl-pyrazolo[3,4-b][1,4]benzodiazepine (IVjj) was prepared by reacting 0.0023 moles of (2-amino-4-methoxy-5-(1-methylethoxy)phenyl)-(2-chlorophenyl)-methanone (Xjj) with 4-amino-5-chloro-3-methyl-1-(2-propenyl)-1H-pyrazole (XIII), and subsequent dealkylation of the intermediate, 5-(2-chlorophenyl)-1,2-dihydro-8-methoxy-7-(1-methylethoxy)-3-methyl-1-(2-propenyl)-pyrazolo[3,4-b][1,4]benzodiazepine (XIVjj) with diisobutylaluminum hydride in a manner analogous to Example 72. MH+/Z=397.

Example 87

Preparation of 5-(2-chlorophenyl)-1,2-dihydro-8-methoxy-7-methoxyethoxy-3-methyl-pyrazolo[3,4-b][1,4]benzodiazepine (IVkk)

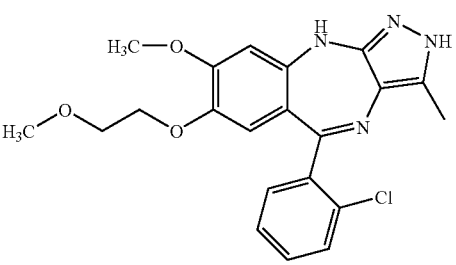

IVkk 5-(2-chlorophenyl)-1,2-dihydro-8-methoxy-7-methoxyethoxy-3-methyl-pyrazolo[3,4-b][1,4]benzodiazepine (IVkk) was prepared by reacting 0.0014 moles of (2-amino-4-methoxy-5-(2-methoxyethoxy)phenyl)-(2-chlorophenyl)-methanone (Xkk) with 4-amino-5-chloro-3-methyl-1-(2-propenyl)-1H-pyrazole (XIII), and subsequent dealkylation of the intermediate, 5-(2-chlorophenyl)-1,2-dihydro-8-methoxy-7-methoxyethoxy-3-methyl-1-(2-propenyl)-pyrazolo[3,4-b][1,4]benzodiazepine (XIVkk) with diisobutylaluminum hydride in a manner analogous to Example 72. MH+/Z=413.

Example 88

Preparation of 4-amino-5-chloro-3-methyl-1-(2-propenyl)-1H-pyrazole (XIII), method 1
(scheme 5)

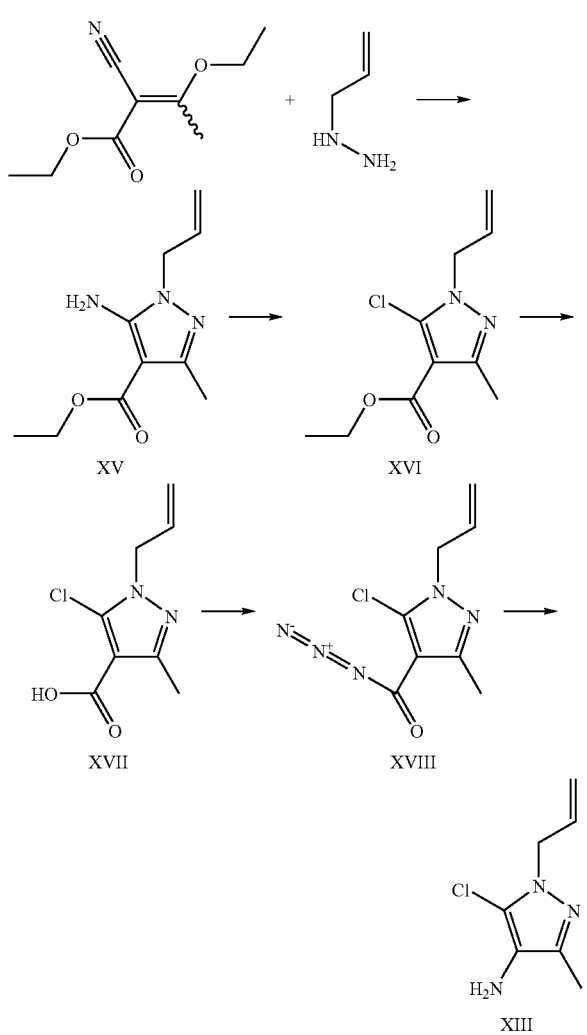

Step 1: Preparation of ethyl 5-amino-3-methyl-1-(2-propenyl)-1H-pyrazole-4-carboxylate (XV)

To a solution of 10.3 g (0.056 mole) of ethyl 2-cyano-3-ethoxy-2-butenoate in 250 mL of methanol was added 8.9 g (0.0616 mole) of allylhydrazine dihydrochloride and 39 mL of triethylamine. The reaction mixture was refluxed at 80° C. for 3 hours, and then concentrated under reduced pressure. The residue was purified by silica gel chromatography, eluting with ethyl acetate-hexane (1:1) to give 6.7 g of ethyl 5-amino-3-methyl-1-(2-propenyl)-1H-pyrazole-4-carboxylate (XV) as a yellow oil.

Step 2: Preparation of ethyl 5-chloro-3-methyl-1-(2-propenyl)-1H-pyrazole-4-carboxylate (XVI)

To a solution of 6.7 g (0.032 mole) of ethyl 5-amino-3-methyl-1-(2-propenyl)-1H-pyrazole-4-carboxylate (XV) in 30 mL of concentrated hydrochloric acid was added 8.6 g (0.064 mole) of copper (II) chloride. The mixture was cooled to 0° C. and 2.65 g (0.038 mole) of sodium nitrite was added portionwise over 20 minutes. The mixture was stirred at room temperature for 1 hour, and then at 40° C. for 2 hours. The mixture was diluted with 50 mL of water and extracted twice with chloroform. The chloroform extracts were dried over anhydrous sodium sulfate, filtered and concentrated under reduced pressure. The residue was purified by silica gel chromatography, eluting with ethyl acetate-hexane (1:4) to give 5.0 g of ethyl 5-chloro-3-methyl-1-(2-propenyl)-1H-pyrazole-4-carboxylate (XVI) as a light yellow oil.

Step 3: Preparation of 5-chloro-3-methyl-1-(2-propenyl)-1H-pyrazole-4-carboxylic acid (XVII)

To a solution of 5.0 g (0.0249 mole) of ethyl 5-chloro-3-methyl-1-(2-propenyl)-1H-pyrazole-4-carboxylate (XVI) in 40 mL of tetrahydrofuran-water-methanol (3:1:1) was added 5 mL of 10 M sodium hydroxide solution. The mixture was heated at 65° C. for 4 hours and then concentrated to a smaller volume under reduced pressure. The pH was adjusted to 1-2 by the addition of hydrochloric acid. The product was collected by filtration, washed with water and dried to yield 4.7 g of 5-chloro-3-methyl-1-(2-propenyl)-1H-pyrazole-4-carboxylic acid (XVII) as a tan solid.

Step 4: Preparation of 5-chloro-3-methyl-1-(2-propenyl)-1H-pyrazole-4-carbonyl azide (XVIII)

To a solution of 6.0 g (0.030 mole) of 5-chloro-3-methyl-1-(2-propenyl)-1H-pyrazole-4-carboxylic Acid (XVII), 4.2 mL (0.030 mole) of triethylamine and 100 mL of acetone at −10° C. was added 2.9 mL (0.030 mole) of ethyl chloroformate. After 30 minutes, 5.8 g (0.090 mole) of sodium azide in 50 mL of water was added. The mixture was stirred at room temperature for 1 hour and then concentrated under reduced pressure to ca. half the original volume. The mixture was extracted twice with chloroform, and the extracts were dried over anhydrous sodium sulfate, filtered, and concentrated under reduced pressure to give 4.7 g of preparation of 5-chloro-3-methyl-1-(2-propenyl)-1H-pyrazole-4-carbonyl azide (XVIII) as a white solid.

Step 5: Preparation of 4-amino-5-chloro-3-methyl-1-(2-propenyl)-1H-pyrazole (XIII)

A solution of 12.3 g (0.0545 mole) of 5-chloro-3-methyl-1-(2-propenyl)-1H-pyrazole-4-carbonyl azide (XVIII) in 120 mL of toluene was heated at 100° C. for 1 hour. 20 mL of hydrochloric acid was added and the mixture was heated at 110° C. for 2 hours and then cooled. The mixture was concentrated under reduced pressure, and then stirred at room temperature with 50 mL of dichloromethane and 10 mL of triethylamine. The mixture was filtered and the filtrate concentrated under reduced pressure. The residue was purified by silica gel chromatography, eluting with ethyl acetate-hexane (1:1) to give 6.0 g of 4-amino-5-chloro-3-methyl-1-(2-propenyl)-1H-pyrazole (XIII) as an orange oil. MS MH+/Z 172

This material was of sufficient purity for use in the subsequent reactions.

Example 89

Preparation or 4-amino-5-chloro-3-methyl-1-(2-propenyl)-1H-pyrazole (XIII), method 2
(scheme 6)

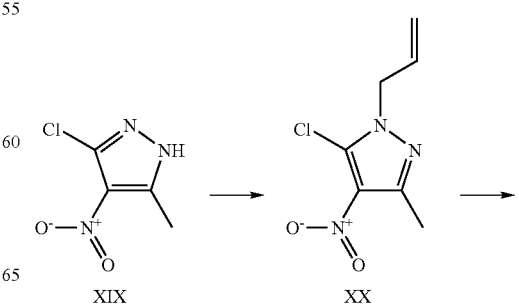

-continued

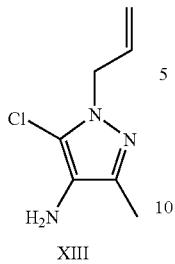

XIII

Step 1: Preparation of 5-chloro-3-methyl-4-nitro-1-(2-propenyl)-1H-pyrazole (XX)

To a solution of 5.0 g (0.031 mole) of 5-chloro-3-methyl-4-nitro-1H-pyrazole in 100 mL of anhydrous tetrahydrofuran under argon, was added 0.37 g (0.0464 mole) of lithium hydride. The mixture was stirred at room temperature for 15 minutes. Then 5.6 g (0.0464 mole) of allyl bromide was added, and the mixture was heated at 80° C. for 10 hours. The mixture was cooled, poured onto ice and extracted twice with ethyl acetate. The combined ethyl acetate layers were dried over anhydrous sodium sulfate, filtered and concentrated under reduced pressure. The residue was purified by silica gel chromatography, eluting with ethyl acetate-hexane (1:2) to give, as the more polar component, 1.36 g of 3-chloro-5-methyl-4-nitro-1-(2-propenyl)-1H-pyrazole as a colorless oil and, as the less polar component, 0.5 g of 5-chloro-3-methyl-4-nitro-1-(2-propenyl)-1H-pyrazole (XX) as a colorless oil.

Step 2: Reduction of XX to form 4-amino-5-chloro-3-methyl-1-(2-propenyl)-1H-pyrazole (XIII)

A mixture of 0.5 g (0.00248 mole) of 5-chloro-3-methyl-4-nitro-1-(2-propenyl)-1H-pyrazole (XX), 1.6 g (0.0198 mole) of ammonium chloride, 1.6 g of zinc powder, 20 mL of methanol and 20 mL of water was stirred at room temperature for 1 hour. The mixture was filtered, and the filtrate extracted with ethyl acetate. The ethyl acetate layer was dried over anhydrous sodium sulfate, filtered and concentrated under reduced pressure. Purification of the residue by silica gel chromatography, eluting with ethyl acetate-hexane (1:1) gave 0.10 g of 4-amino-5-chloro-3-methyl-1-(2-propenyl)-1H-pyrazole (XIII), which was identical to the material prepared in Example 88 (method 1) above.

Example 90

Preparation of 5-(2-chlorophenyl)-1,2-dihydro-7-fluoro-8-methoxy-pyrazolo[3,4-b][1,4]benzodiazepine (XXIIa)

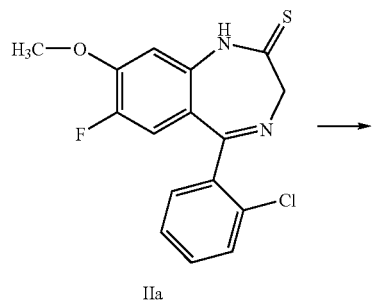

IIa

-continued

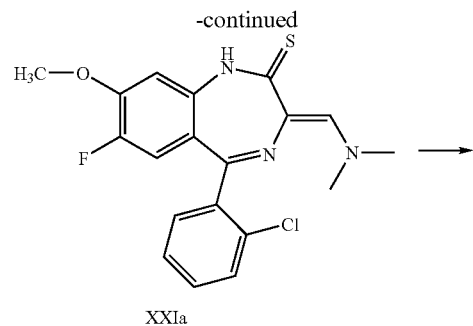

To a solution of 0.64 g (0.0019 mole) of 5-(2-chlorophenyl)-1,3-dihydro-7-fluoro-8-methoxy-2H-1,4-benzodiazepin-2-thione (IIa) in 5 mL of dichloromethane was added 5 mL (0.029 mole) of 1,1-diethoxy-N,N-dimethyl-methanamine. The mixture was stirred overnight at room temperature, then concentrated under reduced pressure. The residue, which contains intermediate XXIa, was stirred with a mixture of 18 mL of dichloromethane, 5.5 mL of methanol and 0.3 mL of hydrazine for 6 hours and then partitioned between dichloromethane and water. The dichloromethane layer was washed twice with water, dried over anhydrous sodium sulfate, filtered and concentrated under reduced pressure. The product was purified by silica gel chromatography eluting with ethyl acetate-hexane (4:1) to provide 0.500 g of 5-(2-chlorophenyl)-1,2-dihydro-7-fluoro-8-methoxy-pyrazolo[3,4-b][1,4]benzodiazepine (XXIIa). Recrystallization from dichloromethane-ethyl acetate gave XXIIa as a light red solid, mp 242-243° C.

Example 91

Preparation of 5-(2-chlorophenyl)-1,2-dihydro-8-methoxy-7-methyl-pyrazolo[3,4-b][1,4]benzodiazepine (XXIIz)

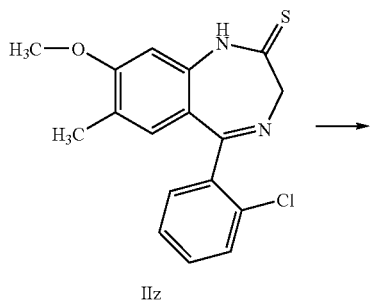

IIz

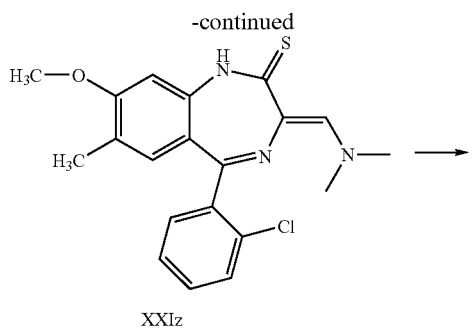

XXIz

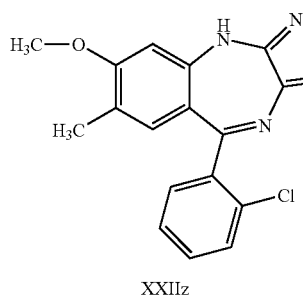

XXIIz 5-(2-chlorophenyl)-1,2-dihydro-8-methoxy-7-methyl-pyrazolo[3,4-b][1,4]benzodiazepine (XXIIz) was prepared by reacting 0.003 moles of 5-(2-chlorophenyl)-1,3-dihydro-8-methoxy-7-methyl-2H-1,4-benzodiazepin-2-thione (IIz) with 1,1-diethoxy-N,N-dimethyl-methanamine and then hydrazine in a manner analogous to Example 90. Recrystallization from ethyl acetate-methanol provided 5-(2-chlorophenyl)-1,2-dihydro-8-methoxy-7-methyl-pyrazolo[3,4-b][1,4]benzodiazepine as a light red solid, mp 275-276° C.

Example 92

Preparation of 5-(2-chlorophenyl)-1,2-dihydro-7-cyano-8-methoxy-pyrazolo[3,4-b][1,4]benzodiazepine (XXIIb)

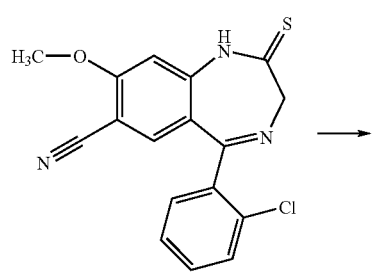

IIb

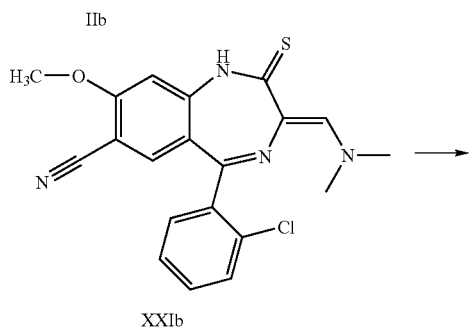

XXIb

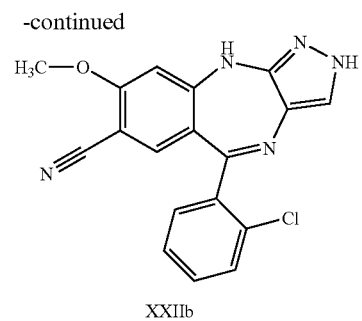

XXIIb 5-(2-chlorophenyl)-1,2-dihydro-7-cyano-8-methoxy-pyrazolo[3,4-b][1,4]benzodiazepine (XXIIb) was prepared by reacting 0.00096 moles of 5-(2-chlorophenyl)-7-cyano-1,3-dihydro-8-methoxy-2H-1,4-benzodiazepin-2-thione (IIb) with 1,1-diethoxy-N,N-dimethyl-methanamine and then hydrazine in a manner analogous to the example above. Recrystallization from ethyl acetate provided 5-(2-chlorophenyl)-1,2-dihydro-7-cyano-8-methoxy-pyrazolo[3,4-b][1,4]benzodiazepine (XXIIb) as a light red solid, mp 288-290° C.

Example 93

| Tablet Formulation | | | | | | |
|---|---|---|---|---|---|---|
| Ingredients | Mg/Tablet | | | | | |
| Compound 1* | 5 | 25 | 100 | 250 | 500 | 750 |
| Anhydrous Lactose | 103 | 83 | 35 | 19 | 38 | 57 |
| Croscarmellose Sodium | 6 | 6 | 8 | 16 | 32 | 48 |
| Povidone K30 | 5 | 5 | 6 | 12 | 24 | 36 |
| Magnesium Stearate | 1 | 1 | 1 | 3 | 6 | 9 |
| Total Weight | 120 | 120 | 150 | 300 | 600 | 900 |

*Compound 1 represents a compound of the invention.

Manufacturing Procedure:
1. Mix Items 1, 2 and 3 in a suitable mixer for 15 minutes.
2. Granulate the powder mix from Step 1 with 20% Povidone K30 Solution (Item 4).
3. Dry the granulation from Step 2 at 50° C.
4. Pass the granulation from Step 3 through suitable milling equipment.
5. Add the Item 5 to the milled granulation Step 4 and mix for 3 minutes.
6. Compress the granulation from Step 5 on a suitable press.

Example 94

| Capsule Formulation | | | | | |
|---|---|---|---|---|---|
| Ingredients | mg/Capsule | | | | |
| Compound 1* | 5 | 25 | 100 | 250 | 500 |
| Anhydrous Lactose | 159 | 123 | 148 | — | — |
| Corn Starch | 25 | 35 | 40 | 35 | 70 |
| Talc | 10 | 15 | 10 | 12 | 24 |
| Magnesium Stearate | 1 | 2 | 2 | 3 | 6 |
| Total Fill Weight | 200 | 200 | 300 | 300 | 600 |

*Compound 1 represents a compound of the invention.

Manufacturing Procedure:
1. Mix Items 1, 2 and 3 in a suitable mixer for 15 minutes.
2. Add Items 4 & 5 and mix for 3 minutes.
3. Fill into a suitable capsule.

Example 95

Injection Solution/Emulsion Preparation

| Item | Ingredient | mg/mL |
|---|---|---|
| 1 | Compound 1* | 1 mg |
| 2 | PEG 400 | 10-50 mg |
| 3 | Lecithin | 20-50 mg |
| 4 | Soy Oil | 1-5 mg |
| 5 | Glycerol | 8-12 mg |
| 6 | Water q.s. | 1 mL |

*Compound 1 represents a compound of the invention.

Manufacturing Procedure:
1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 um filter and fill into vials.

Example 96

Injection Solution/Emulsion Preparation

| Item | Ingredient | mg/mL |
|---|---|---|
| 1 | Compound 1* | 1 mg |
| 2 | Glycofurol | 10-50 mg |
| 3 | Lecithin | 20-50 mg |
| 4 | Soy Oil | 1-5 mg |
| 5 | Glycerol | 8-12 mg |
| 6 | Water | q.s. 1 mL |

*Compound 1 represents a compound of the invention.

Manufacturing Procedure:
1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 um filter and fill into vials.

Determination of Activity

The antiangiogenic and antiproliferative activities of the compounds of the invention are demonstrated below. These effects indicate that the compounds of interest are useful in inhibiting angiogenesis and in the treatment of cancer, in particular solid tumors such as breast and colon cancer.

Example 97

CDK2 Flash Plate Assay

To determine inhibition of CDK2 activity, purified recombinant retinoblastoma (Rb) protein was coated on 96 well FlashPlates (New England Nuclear, Boston, Mass.). Rb is a natural substrate for phosphorylation by CDK2 (Herwig and Strauss *Eur. J. Biochem.*, Vol. 246 (1997) pp. 581-601 and references therein). Recombinant active human Cyclin E/CDK2 complexes were partially purified from extracts of insect cells. The active Cyclin E/CDK2 was added to the Rb-coated FlashPlates along with $^{33}$P-ATP and dilutions of test compounds. Plates were incubated for 25 minutes at room temperature with shaking, then washed and counted in the Topcount scintillation counter (Packard Instrument Co., Downers Grove, Ill.). Dilutions of test compounds were tested in duplicate in each assay. The percent inhibition of Rb phosphorylation, which is a measure of the inhibition of CDK2 activity, was determined according to the following formula:

$$100 \times \left[ 1 - \frac{\text{test compound} - \text{nonspecific}}{\text{total} - \text{nonspecific}} \right]$$

where "test compound" refers to the average counts per minute of the test duplicates, "nonspecific" refers to the average counts per minute when no Cyclin E/CDK2 was added, and "total" refers to the average counts per minute when no compound was added.

The compounds of the present invention have CDK2 IC$_{50}$ values less than 10 µM, preferably less than 1 µM. KDR IC$_{50}$ values for representative compounds are set forth in Table I below.

TABLE I

Inhibition of CDK2

| Compound Number | $R^1$ | $R^2$ | $R^3$ | $R^4$ | IC$_{50}$ (µM) |
|---|---|---|---|---|---|
| IVa | F | OCH$_3$ | CH$_3$ | Cl | 1.330 |
| IVb | CN | OCH$_3$ | CH$_3$ | Cl | 0.184 |
| IVf | F | OCH$_2$CH$_2$OCH$_3$ | CH$_3$ | Cl | 0.395 |
| IVh | F | OCH(CH$_3$)$_2$ | CH$_3$ | Cl | 0.247 |

Example 98

KDR & FGFr

To determine inhibition of KDR and FGFR, kinase assays were conducted using an HTRF (Homogeneous Time Resolved Fluorescence) assay. This assay is described in A. J. Kolb et. al., Drug Discovery Today, 1998, 3(7), p 333.

Prior to kinase reaction, recombinant EEE-tagged KDR was activated in the presence of activation buffer (50 mM HEPES, pH 7.4, 1 mM DTT, 10% glycerol, 150 mM NaCl, 0.1 mM EDTA, 26 mM MgCl$_2$, and 4 mM ATP). The enzyme was incubated at 4° C. for 1 hour.

Kinase activity assays were performed in 96-well polypropylene plates (Falcon) with a total volume of 90 µL in each well. Each well contained 1 µM KDR substrate (Biotin-EE-EEYFELVAKKKK), 1 nM activated KDR, and a test compound with one of 8 assay concentrations ranging from 100 µM to 128 pM (1:5 serial dilution). The kinase activity assay was done in the presence of 100 mM HEPES, pH 7.4, 1 mM DTT, 0.1 mM Na$_2$VO$_4$, 25 mM MgCl$_2$, 50 mM NaCl (from KDR stock solution), 1% DMSO (from compound), 0.3 mM ATP (at K$_m$ concentration) and 0.02% BSA. The reaction was incubated at 37° C. for 30 minutes. To stop the KDR reaction, 72 µL of reaction mixture was transferred into a STOP plate containing 18 µL of revelation buffer (20 mM EDTA, 50 mM HEPES, pH 7.4, 0.02% BSA, 10 nM Eu-labelled anti-pY antibody (final conc. 2 nM), and 100 nM streptavidin (final conc. 20 nM)). After mixing, 35 µL of solution was transferred into duplicate wells of a 384-well black plate (Costar), and read at 615/665 nm on a Wallac Victor 5 reader.

FGFR activity assays were carried out as described above for the KDR activity assay with the following differences. GST-tagged FGFR enzyme was activated at room temperature for 1 hour in the following activation buffer: 100 mM HEPES, pH 7.4, 50 mM NaCl, 20 mM MgCl$_2$, and 4 mM ATP. The kinase activity assay was performed with 1 µM substrate (Biotin-EEEEYFELV), 1.5 nM activated FGFR, and test compound in the presence of 100 mM HEPES, 1 mM DTT, 0.4 mM MgCl$_2$, 0.4 mM MnCl$_2$, 50 mM NaCl, 1% DMSO, 10 µM ATP (K$_m$=8.5 µM for FGFR), 0.1 mM Na$_2$VO$_4$, and 0.02% BSA, in a total volume of 90 µL. The rest of the assay was performed in the same manner as KDR assay.

Compound IC$_{50}$ values were determined from duplicate sets of data, and calculated by using Excel and fitting data to equation Y=[(a−b)/{1+(X/c)$^d$}]+b, where a and b are enzyme activity in the presence of no test inhibitor compound and an infinite amount of inhibitor test compound, respectively, c is the IC$_{50}$ and d is the hill constant of the compound response. The IC$_{50}$ value is the concentration of test compound that reduces by 50% the enzyme activity under the test conditions described.

The compounds of the present invention have KDR IC$_{50}$ values less than 10 µM, preferably less than 1 µM, most preferably less than 0.5 µM, or FGFR IC$_{50}$ values less than 10 µM, preferably less than 1 µM. Most preferably, the compounds of the invention have KDR IC$_{50}$ values less than 1 µM and FGFR IC$_{50}$ values less than 1 µM. KDR IC$_{50}$ values for representative compounds are set forth in Table II below, and FGFR IC$_{50}$ values for representative compounds are set forth in Table III below.

TABLE II

Inhibition of KDR

| Compound Number | R$^1$ | R$^2$ | R$^3$ | R$^4$ | IC$_{50}$ (µM) |
|---|---|---|---|---|---|
| IVa | F | OCH$_3$ | CH$_3$ | Cl | 0.010 |
| IVc | C(O)NH$_2$ | OCH$_3$ | CH$_3$ | Cl | 0.022 |
| IVi | F | OCH$_2$CH$_2$N(CH$_2$CH$_2$)$_2$O | CH$_3$ | Cl | 0.031 |
| IVkk | OCH$_2$CH$_2$ | OCH$_3$ | CH$_3$ | Cl | 0.024 |

TABLE III

Inhibition of FGFR

| Compound Number | R$^1$ | R$^2$ | R$^3$ | R$^4$ | IC$_{50}$ (µM) |
|---|---|---|---|---|---|
| IVa | F | OCH$_3$ | CH$_3$ | Cl | 0.028 |
| IVc | C(O)NH$_2$ | OCH$_3$ | CH$_3$ | Cl | 0.032 |
| IVk | CN | OCH$_2$CH$_2$N(CH$_2$CH$_2$)$_2$O | CH$_3$ | Cl | 0.033 |
| IVw | CH$_3$ | CH$_3$ | CH$_3$ | Cl | 0.038 |

Example 99

MDA-MB-435, SW480, and HCT-116

The estrogen receptor negative epithelial breast carcinoma line (MDA-MB-435) was purchased from American Type Cell Culture Collection (ATCC; Rockville, Md.) and was grown in the medium recommended by ATCC. For analysis of the effect of the test compounds on growth of these cells, the cells were plated at 2000 cells per well in a 96-well tissue culture plate, and were incubated overnight at 37° C. with 5% CO$_2$. The next day, the test compounds were dissolved in 100% dimethyl sulfoxide (DMSO) to yield a 10 mM stock solution. Each compound was diluted with sterile medium to 1 mM in a sufficient quantity to yield a final concentration of 120 µM. The compounds were then serially diluted in medium with 1.2% DMSO. One-fourth final volume of the diluted compounds was transferred to 96 well plates. Test compounds were assayed in duplicate. DMSO was added to a row of "control cells" such that the final concentration of DMSO in each well was 0.3%. Wells to which no cells were added served as the "blank." Wells to which no inhibitor was added served as "no inhibitor control". The plates were returned to the incubator, and 5 days post addition of test compound, were analyzed as described below.

3-(4,5-Dimethylthiazole-2-yl)-2,5-diphenyl-2H-tetrazolium bromide (thiazolyl blue; MTT) was added to each well to yield a final concentration of 1 mg/mL. The plates were then incubated at 37° C. for 3 hours. The plates were centrifuged at 1000 rpm for 5 minutes prior to aspiration of the MTT-containing medium. The MTT-containing medium was then removed and 100 µL 100% ethanol was added to each well to dissolve the resulting formazan metabolite. To ensure complete dissolution, plates were shaken for 15 minutes at room temperature. Absorbencies were read in a microtiter plate reader (Molecular Dynamics) at a wavelength of 570 nm with a 650 nm reference. Percent inhibition was calculated by subtracting the absorbance of the blank (no cell) wells from all wells, then subtracting the division of the average absorbance of each test duplicate by the average of the controls from 1.00. Inhibitory concentrations (IC$_{50}$) were determined from the linear regression of a plot of the logarithm of the concentration versus the percent inhibition.

The compounds of the present invention have MDA-MB-435 IC$_{50}$ values less than 20 µM, preferably less than 2 µM. The IC$_{50}$ value for inhibition in the MDA-MB-435 cell-based assay for 5-(2-chlorophenyl)-1,3-dihydro-7,8-dimethyl-2H-1,4-benzodiazepin-2-one (Iw) is 0.950 µM.

The colon adenocarcinoma line SW480 and the colon carcinoma line HCT-116 also were obtained from the ATCC and were tested according to the same protocol provided above for MDA-MB-435 cell based assay with the following modifications. Cell line SW480 was plated at 1000 cells per well and analyzed at 6 days post addition of the test compound. Cell line HCT-116 was plated at 1000 cells per well and analyzed at 4 days post addition of test compound.

The compounds of the present invention have SW480 IC$_{50}$ values less than 20 µM, preferably less than 2 µM. The IC$_{50}$ value for inhibition in the SW480 (colon) based assay for 5-(2-chlorophenyl)-1,3-dihydro-7,8-dimethyl-2H-1,4-benzodiazepin-2-one (Iw) is 0.950 µM.

The compounds of the present invention have HCT-116 IC$_{50}$ values less than 20 µM, preferably less than 2 µM. The IC$_{50}$ values for inhibition in the HCT-116 (colon) based assay for representative compounds are set forth below in Table IV.

TABLE IV

Antiproliferative Activity HCT 116 (colon) Assay

| Compound Number | R$^1$ | R$^2$ | R$^3$ | R$^4$ | IC$_{50}$ (µM) |
|---|---|---|---|---|---|
| IVgg | OCH$_3$ | OCH$_2$CH$_2$OCH$_3$ | CH$_3$ | Cl | 0.197 |
| IVkk | OCH$_2$CH$_2$OCH$_3$ | OCH$_3$ | CH$_3$ | Cl | 0.509 |
| IVa | F | OCH$_3$ | CH$_3$ | Cl | 1.040 |
| IVf | F | OCH$_2$CH$_2$OCH$_3$ | CH$_3$ | Cl | 0.498 |

Example 100

VEGF and FGF-Stimulated HUVEC Proliferation Assays

The antiproliferative activity of test compounds of this invention in cell-based assays was evaluated by BrdU assay using the BrdU kit (Roche Biochemicals 1-647-229). Human umbilical vein endothelial cells (HUVEC, Clonetics CC-2519) were cultured in EGM-2 (Clonetics CC-3162) medium and seeded at 10000 cells per well in a volume of 200 µL of EGM-2 (Clonetics CC-3162) media in a 96-well flat bottom plates (Costar 3595) overnight. After 24 hours of growth at 37° C. with 5% $CO_2$, the incubation media was removed slowly by aspiration, and the content of each well was washed with 300 µL pre-warmed EBM-2 (Clonetics CC-3156) containing 50 µg per mL of gentamycin and 50 ng per mL of amphotercin-B (Clonetics CC-4083). Subsequently, the remaining media was again aspirated and replaced with 160 µL per well of serum starvation media (EBM-2 supplemented with 1% heat inactivated FBS (Clonetics CC-4102), 50 µg per mL gentamycin and 50 ng per mL of amphotercin-B (Clonetics CC-4083), 10 units per mL of Wyeth-Ayerst heparin (NDC0641-0391-25), and 2 mM L-glutamine (GIBCO 25030-081). After serum starving the cells for 24 hours, 20 µL of test compound at 10× test concentration in serum starvation medium with 2.5% DMSO was added to the appropriate wells. The control wells contained 20 µL of serum starvation medium with 2.5% DMSO. Plates were returned to the incubator for 2 hours. After pre-incubating the cells with the test compounds for 2 hours, 20 µL of growth factors at 10X assay concentration diluted in serum starvation media, FGF at 50 ng per mL, or VEGF (R&D systems 293-VE) at 200 ng per mL were added. The final concentration of FGF in the assay was 5 ng per mL and the final concentration of VEGF in the assays was 20 ng per mL. The growth factor free control wells had 20 µL per well of serum starvation media with the same amount of BSA as the wells with growth factors. The plates were returned to the incubator for an additional 22 hours.

BrdU ELISA

After 24 hour exposure to the test compounds, the cells were labeled with BrdU (Roche Biochemicals 1-647-229), by adding 20 µL per well of BrdU labeling reagent that has been diluted (1:100) in serum starvation medium. The plates were then returned to the incubator for 4 hours. The labeling medium was removed by draining the medium onto paper towels. The cells were fixed and DNA denatured by adding 200 µL of fixation/denaturation solution to each well and incubating at room temperature for 45 minutes. The fixation/denaturation solution was drained onto paper towels and to each well was added 100 µL of anti-BrdU-POD and the wells were incubated for 2 hours at room temperature. The antibody solution was removed and the wells were each washed 3-4 times with 300 µL PBS. 100 µL of the TMB substrate solution was added to each well, and the wells were incubated at room temperature for 5-8 minutes. The reaction was then stopped by adding 100 µL per well of 1 M phosphoric acid. The plates were read at 450 nm with reference wavelength of 650 nm. The percent inhibition for each test compound was calculated by subtracting the absorbency of the blank (no cells) wells from all wells, then subtracting the division of the average absorbency of each test duplicate by the average of the controls from 1. The final product was then multiplied by 100 (% of inhibition=(1—average absorbency of test duplicate/average of control) 100). The $IC_{50}$ value is the concentration of test compound that inhibits by 50% BrdU labeling and is a measure of inhibition of cell proliferation. The $IC_{50}$ is determined from the linear regression of a plot of the logarithm of the concentration versus percent inhibition.

The compounds of the present invention have VEGF—stimulated HUVEC assay $IC_{50}$ values less than 10 µM, preferably less than 1 µM, or FGF—stimulated HUVEC assay $IC_{50}$ values less than 10 µM, preferably less than 1 µM. Most preferably, the compounds of the invention have VEGF—stimulated HUVEC assay $IC_{50}$ values less than 1 µM and FGF—stimulated HUVEC assay $IC_{50}$ values less than 1 µM. The $IC_{50}$ values for representative compounds in the VEGF—stimulated HUVEC assay are provided in Table V, and $IC_{50}$ values for representative compounds in the FGF—stimulated HUVEC assay are provided in Table VI below.

TABLE V

Antiproliferative Activity VEGF-stimulated HUVEC Assay

| Compound Number | $R^1$ | $R^2$ | $R^3$ | $R^4$ | $IC_{50}$ (µM) |
|---|---|---|---|---|---|
| IVa | F | $OCH_3$ | $CH_3$ | Cl | 0.023 |
| IVw | $CH_3$ | $CH_3$ | $CH_3$ | Cl | 0.022 |
| IVy | $OCH_3$ | Cl | $CH_3$ | Cl | 0.174 |
| IVz | $CH_3$ | $OCH_3$ | $CH_3$ | Cl | 0.012 |

TABLE VI

Antiproliferative Activity FGF-stimulated HUVEC Assay

| Compound Number | $R^1$ | $R^2$ | $R^3$ | $R^4$ | $IC_{50}$ (µM) |
|---|---|---|---|---|---|
| IVa | F | $OCH_3$ | $CH_3$ | Cl | 0.100 |
| IVb | CN | $OCH_3$ | $CH_3$ | Cl | 0.005 |
| IVc | $C(O)NH_2$ | $OCH_3$ | $CH_3$ | Cl | <0.001 |
| IVw | $CH_3$ | $CH_3$ | $CH_3$ | Cl | 0.036 |

Example 101

H460a

The H460a cell line was purchased from (ATCC; Rockville, Md.) and was grown in the medium recommended by ATCC. For analysis of the effect of the test compounds on growth of these cells, the cells were plated at 150 cells per well in a 96-well tissue culture plate, and were incubated overnight at 37° C. with 5% $CO_2$. The next day, the test compounds were dissolved in 100% dimethyl sulfoxide (DMSO) to yield a 10 mM stock solution. Each compound was diluted with sterile medium to 1 mM in a sufficient quantity to yield a final concentration of 120 µM. The compounds were then serially diluted in medium with 1.2% DMSO. One-fourth final volume of the diluted compounds was transferred to 96 well plates. Test compounds were assayed in duplicate. DMSO was added to a row of "control cells" such that the final concentration of DMSO in each well was 0.3%. Wells to which no cells were added served as the "blank." Wells to which no inhibitor was added served as "no inhibitor control". The plates were returned to the incubator, and 5 days post addition of test compound, were analyzed as described below. 3-(4,5-Dimethylthiazole-2-yl)-2,5-diphenyl-2H-tetrazolium bromide (thiazolyl blue; MTT) was added to each well to yield a final concentration of 1 mg/mL. The plates were then incubated at 37° C. for 3 hours. The plates were centrifuged at 1000 rpm for 5 minutes prior to aspiration of the MTT-containing medium. The MTT-containing medium was then removed and 100 µL 100% ethanol was added to each well to dissolve the resulting formazan metabolite. To ensure complete dissolution, plates were shaken for 15 minutes at room temperature. Absorbencies were read in a microtiter plate reader (Molecular Dynamics) at a wavelength of 570 nm with a 650 nm reference. Percent inhibition was calculated by subtracting the absorbance of the blank (no cell) wells from all wells, then subtracting the division of the average absorbance of each test duplicate by the average of the controls from 1.00. Inhibitory concentrations ($IC_{50}$) were determined from the linear regression of a plot of the logarithm of the concentration versus the percent inhibition.

The compounds of the present invention have H460a $IC_{50}$ values less than 20 µM, preferably less than 2 µM. The $IC_{50}$ values for inhibition in the H460a-based assay for representative compounds are set forth below in Table VII. $IC_{90}$ values for representative compounds in the H460a assay are provided in Table VII below.

TABLE VII

Antiproliferative Activity H460a Assay

| Compound Number | $R^1$ | $R^2$ | $R^3$ | $R^4$ | $IC_{90}$ (µM) |
|---|---|---|---|---|---|
| IVa | F | $OCH_3$ | $CH_3$ | Cl | 1.570 |
| IVb | CN | $OCH_3$ | $CH_3$ | Cl | 0.118 |

As noted above, the compounds of the invention have antiangiogenic activity and, as such, are useful for the inhibition of angiogenesis in an individual. Angiogenesis has been associated with cancer. In particular, tumors can only grow to a certain size without the growth of new blood vessels to supply and nourish them. Thus, the compounds of the present invention are useful in the treatment of cancer by inhibiting the growth of such new blood vessels. The present invention, therefore, provides a method for the inhibition of angiogenesis in a patient which comprises administering a therapeutically effective amount, i.e., an angiogenesis-inhibiting amount, of a compound of formula IV.

In addition to their antiangiogenic activity, compounds of the invention are inhibitors of various kinases, such as CDK2, KDR, and FGFr. Inhibition of these kinases affects proliferation of tumor cells. Thus, the present invention also provides methods of inhibiting tumor growth through direct inhibition of kinases.

The present invention provides a method for the treatment of cancer which comprises administering to a patient with cancer a therapeutically effective amount of a compound of the invention or a pharmaceutically acceptable salt thereof. In particular, the present invention provides a method for the treatment of breast cancer which comprises administering to a patient with breast cancer a therapeutically effective amount of a compound of the invention or a pharmaceutically acceptable salt thereof. The present invention also provides a method for the treatment of prostate cancer which comprises administering to a patient with prostate cancer a therapeutically effective amount of a compound of the invention or a pharmaceutically acceptable salt thereof. The present invention further provides a method for the treatment of colon cancer which comprises administering to a patient with colon cancer a therapeutically effective amount of a compound of the invention or a pharmaceutically acceptable salt thereof. The present invention provides a method for the treatment of lung cancer which comprises administering to a patient with lung cancer a therapeutically effective amount of a compound of the invention or a pharmaceutically acceptable salt thereof.

While the invention has been illustrated by reference to specific and preferred embodiments, those skilled in the art will understand that variations and modifications may be made through routine experimentation and practice of the invention. Thus, the invention is intended not to be limited by the foregoing description, but to be defined by the appended claims and their equivalents.

What is claimed is:

1. A compound of formula IV,

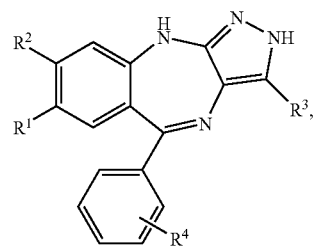

formula IV wherein
  $R^1$ is alkyl, alkoxy, halogen, COOH, COOAlkyl, CN, C(O)N($R^6$)$_2$, or $(OCH_2CH_2)_nOCH_3$;
  $R^2$ is alkyl, halogen, alkyl substituted by halogen, OH, alkoxy, alkoxy substituted by halogen, phenyl, N($R^6$)$_2$, $(OCH_2CH_2)_nOCH_3$, $O(CH_2)_mNR^7R^8$, or $O(CH_2)_n$—C̈N̈; C̈N̈ is a 6-membered heterocycle optionally substituted by alkyl or C(O)O$R^6$;
  or $R^1$ and $R^2$ together form a 5-membered heterocyclic ring;
  $R^3$ is hydrogen or alkyl;
  $R^4$ is hydrogen, halogen, CN, $NO_2$, alkyl, or alkoxy;
  each $R^6$ is independently hydrogen or alkyl;
  $R^7$ and $R^8$ are each independently hydrogen, alkyl, or alkoxyalkyl, or $R^7$ and $R^8$ taken together with the nitrogen atom to which they are attached form a 6-membered heterocycle which is optionally substituted by alkyl;
  each n is independently 1, 2, or 3; and
  m is 2, 3, or 4;
  or a pharmaceutically acceptable salt thereof.

2. A compound of claim 1, wherein $R^2$ is $O(CH_2)_n$—C̈N̈.

3. A compound of claim 2, wherein $R^1$ is halogen.
4. A compound of claim 1, wherein $R^1$ is cyano.
5. A compound of claim 1, wherein $R^2$ is $O(CH_2)_mNR^7R^8$.
6. A compound of claim 5, wherein $R^7$ and $R^8$ together with the N atom to which they are attached form a 6-membered heterocycle.
7. A compound of claim 6, wherein $R^1$ is halogen.
8. A compound of claim 7, selected from the group consisting of:
  5-(2-chlorophenyl)-1,2-dihydro-7-fluoro-8-(3-(4-morpholinyl)propoxy))-3-methyl-pyrazolo[3,4-b][1,4]benzodiazepine; and
  7-bromo-5-(2-chlorophenyl)-1,2-dihydro-8-(3-(4-morpholinyl)propoxy))-3-methyl-pyrazolo[3,4-b][1,4]benzodiazepine.
9. A compound of claim 6, wherein $R^1$ is cyano.
10. A compound of claim 9, selected from the group consisting of:
  5-(2-chlorophenyl)-7-cyano-1,2-dihydro-8-(3-(4-morpholinyl)propoxy))-3-methyl-pyrazolo[3,4-b][1,4]benzodiazepine; and 5-(2-chlorophenyl)-7-cyano-1,2-dihydro-8-(2-(4-methyl-1-piperazinyl)ethoxy)-3-methyl-pyrazolo[3,4-b][1,4]benzodiazepine.

11. A compound of claim 5, wherein $R^7$ and $R^8$ are each independently hydrogen, alkyl, or alkoxyalkyl.

12. A compound of claim 11, wherein $R^1$ is halogen.

13. A compound of claim 11, wherein $R^1$ is cyano.

14. A compound of claim 13, which is 5-(2-chlorophenyl)-7-cyano-1,2-dihydro-8-(2-((2-methoxyethyl)methylamino)-ethoxy)-3-methyl-pyrazolo[3,4-b][1,4]benzodiazepine.

15. A compound of claim 1, wherein $R^2$ is $N(R^6)_2$.

16. A compound of claim 15, wherein $R^1$ is halogen.

17. A compound of claim 16, which is 5-(2-chlorophenyl)-1,2-dihydro-7-fluoro-8-N,N-dimethylamino-3-methyl-pyrazolo[3,4-b][1,4]benzodiazepine.

18. A compound of claim 15, wherein $R^1$ is cyano.

19. A compound of claim 1, wherein $R^2$ is halogen, alkyl, or alkyl substituted by halogen.

20. A compound of claim 19, wherein $R^1$ is alkyl.

21. A compound of claim 20, selected from the group consisting of:
   8-chloro-5-(2-chlorophenyl)-1,2-dihydro-3,7-dimethyl-pyrazolo[3,4-b][1,4]benzodiazepine; and
   5-(2-chlorophenyl)-1,2-dihydro-3,7,8-trimethyl-pyrazolo[3,4-b][1,4]benzodiazepine.

22. A compound of claim 19, wherein $R^1$ is halogen.

23. A compound of claim 19, wherein $R^1$ is alkoxy.

24. A compound of claim 23, selected from the group consisting of:
   5-(2-chlorophenyl)-1,2-dihydro-8-fluoro-7-methoxy-3-methyl-pyrazolo[3,4-b][1,4]benzodiazepine;
   5-(2-chlorophenyl)-1,2-dihydro-7-methoxy-3-methyl-8-trifluoromethyl-pyrazolo[3,4-b][1,4]benzodiazepine; and
   8-chloro-5-(2-chlorophenyl)-1,2-dihydro-7-methoxy-3-methyl-pyrazolo[3,4-b][1,4]benzodiazepine.

25. A compound of claim 1, wherein $R^2$ is hydroxy, alkoxy, or alkoxy substituted by halogen.

26. A compound of claim 25, wherein $R^1$ is halogen.

27. A compound of claim 26, selected from the group consisting of:
   7-chloro-5-(2-chlorophenyl)-1,2-dihydro-8-methoxy-3-methyl-pyrazolo[3,4-b][1,4]benzodiazepine;
   7-bromo-5-(2-chlorophenyl)-1,2-dihydro-8-methoxy-3-methyl-pyrazolo [3,4-b][1,4]benzodiazepine;
   5-(2-chlorophenyl)-1,2-dihydro-7-fluoro-8-methoxy-3-methyl-pyrazolo[3,4-b][1,4]benzodiazepine;
   5-(2-chlorophenyl)-1,2-dihydro-7-fluoro-8-ethoxy-3-methyl-pyrazolo[3,4-b][1,4]benzodiazepine; and
   5-(2-chlorophenyl)-1,2-dihydro-7-fluoro-8-(1-methylethoxy)-3-methyl-pyrazolo[3,4-b][1,4]benzodiazepine.

28. A compound of claim 27, which is 5-(2-chlorophenyl)-1,2-dihydro-7-fluoro-8-methoxy-3-methyl-pyrazolo[3,4-b][1,4]benzodiazepine.

29. A compound of claim 25, wherein $R^1$ is alkoxy.

30. A compound of claim 29, selected from the group consisting of:
   5-(2-chlorophenyl)-1,2-dihydro-7,8-dimethoxy-3-methyl-pyrazolo[3,4-b][1,4]benzodiazepine;
   1,2-dihydro-7,8-dimethoxy-5-(2-methoxyphenyl)-3-methyl-pyrazolo[3,4-b][1,4]benzodiazepine;
   5-(2-chlorophenyl)-1,2-dihydro-7-methoxy-8-(1-methylethoxy)-3-methyl-pyrazolo[3,4-b][1,4]benzodiazepine; and
   5-(2-chlorophenyl)-1,2-dihydro-8-methoxy-7-(1-methylethoxy)-3-methyl-pyrazolo[3,4-b][1,4]benzodiazepine.

31. A compound of claim 25, wherein $R^1$ is alkyl.

32. A compound of claim 31, which is 5-(2-chlorophenyl)-1,2-dihydro-3,7-dimethyl-8-methoxy-pyrazolo[3,4-b][1,4]benzodiazepine.

33. A compound of claim 25, wherein $R^1$ is $O(CH_2)_n OCH_3$.

34. A compound of claim 33, which is 5-(2-chlorophenyl)-1,2-dihydro-8-methoxy-7-methoxyethoxy-3-methyl-pyrazolo[3,4-b][1,4]benzodiazepine.

35. A compound of claim 25, wherein $R^1$ is cyano.

36. A compound of claim 35, which is 5-(2-chlorophenyl)-7-cyano-1,2-dihydro-8-methoxy-3-methyl-pyrazolo[3,4-b][1,4]benzodiazepine.

37. A compound of claim 25, wherein $R^1$ is $NH_2C(O)$.

38. A compound of claim 1, wherein $R^2$ is phenyl.

39. A compound of claim 38, wherein $R^1$ is alkoxy.

40. A compound of claim 39, which is 5-(2-chlorophenyl)-1,2-dihydro-7-methoxy-3-methyl-8-phenyl-pyrazolo[3,4-b][1,4]benzodiazepine.

41. A compound of claim 1, wherein $R^2$ $(OCH_2CH_2)_n OCH_3$.

42. A compound of claim 41, wherein $R^1$ is halogen.

43. A compound of claim 42, which is 5-(2-chlorophenyl)-1,2-dihydro-7-fluoro-8-methoxyethoxy-3-methyl-pyrazolo[3,4-b][1,4]benzodiazepine.

44. A compound of claim 41, wherein $R^1$ is alkoxy.

45. A compound of claim 44, which is 5-(2-chlorophenyl)-1,2-dihydro-7-methoxy-8-methoxyethoxy-3-methyl-pyrazolo[3,4-b][1,4]benzodiazepine.

46. A compound of claim 41, wherein $R^1$ is cyano.

47. A compound of claim 46, selected from the group consisting of:
   5-(2-chlorophenyl)-7-cyano-1,2-dihydro-8-methoxyethoxy-3-methyl-pyrazolo[3,4-b][1,41,4]benzodiazepine; and
   5-(2-chlorophenyl)-7-cyano-1,2-dihydro-8-(2-(2-methoxyethoxy)ethoxy)-3-methyl-pyrazolo[3,4-b][1,41,4]benzodiazepine.

48. A compound of claim 1, wherein $R^1$ and $R^2$ together form a dioxolane ring.

49. A compound of claim 48, which is 5-(2-chlorophenyl)-8,10-dihydro-7-methyl-1,3-dioxolo[4,5-h]pyrazolo[3,4-b][1,4]benzodiazepine.

50. A compound of claim 1, wherein $R^3$ is hydrogen.

51. A compound of claim 50, selected from the group consisting of:
   5-(2-chlorophenyl)-1,2-dihydro-7-fluoro-8-methoxy-pyrazolo[3,4-b][1,4]benzodiazepine;
   5-(2-chlorophenyl)-1,2-dihydro-8-methoxy-7-methyl-pyrazolo[3,4-b][1,4]benzodiazepine; and
   5-(2-chlorophenyl)-1,2-dihydro-7-cyano-8-methoxy-pyrazolo[3,4-b][1,4]benzodiazepine.

52. A pharmaceutical composition of claim 1, comprising:
   (A) a therapeutically effective amount of a compound of formula IV, formula IV

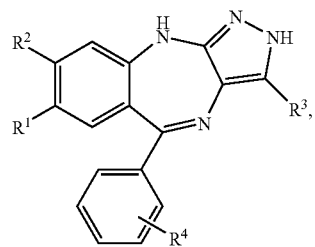

wherein
R¹ is alkyl, alkoxy, halogen, COOH, COOAlkyl, CN, C(O)N(R⁶)₂, or (OCH₂CH₂)ₙOCH₃;
R² is alkyl, halogen, alkyl substituted by halogen, OH, alkoxy, alkoxy substituted by halogen, phenyl, N(R⁶)₂, (OCH₂CH₂)ₙOCH₃, O(CH₂)ₘNR⁷R⁸, or

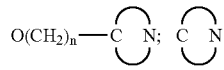

is a 6-membered heterocycle optionally substituted by alkyl or C(O)OR⁶;
or R¹ and R² together form a 5-membered heterocyclic ring;
R³ is hydrogen or alkyl;
R⁴ is hydrogen, halogen, CN, NO₂, alkyl, or alkoxy;
each R⁶ is independently hydrogen or alkyl;
R⁷ and R⁸ are each independently hydrogen, alkyl, or alkoxyalkyl, or R⁷ and R⁸ taken together with the nitrogen atom to which they are attached form a 6-membered heterocycle which is optionally substituted by alkyl;
each n is independently 1, 2, or 3; and
m is 2, 3, or 4;
or a pharmaceutically acceptable salt thereof; and
(B) a pharmaceutically acceptable carrier.

53. A process for preparing a compound of formula IV,

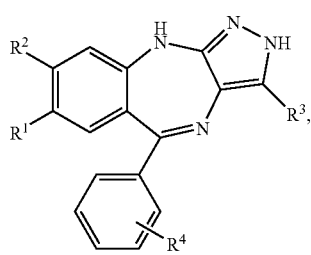

formula IV said process comprising
(a) converting a benzodiazepine lactam of formula I

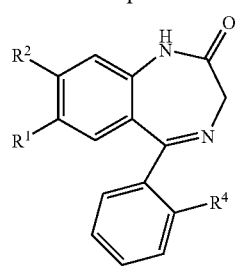

I to a thiolactam of formula II

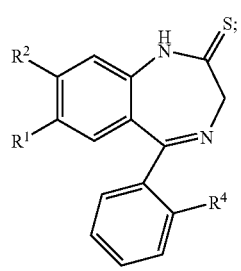

II (b) reacting the thiolactam of formula II with the dimethyl acetal of N,N-dimethyl acetamide to form a compound of formula III

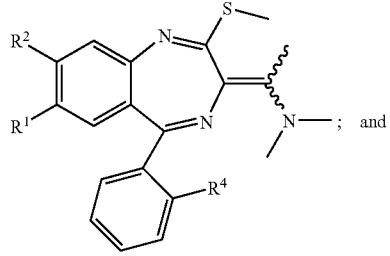

III (c) reacting the compound of formula III with hydrazine to form a compound of formula IV;
and wherein, in the above formulas,
R¹ is alkyl, alkoxy, halogen, COOH, COOAlkyl, CN, C(O)N(R⁶)₂, or (OCH₂CH₂)ₙOCH₃;
R² is alkyl, halogen, alkyl substituted by halogen, OH, alkoxy, alkoxy substituted by halogen, phenyl, N(R⁶)₂, (OCH₂CH₂)ₙOCH₃, O(CH₂)ₘNR⁷R⁸, or

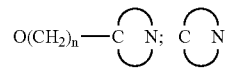

is a 6-membered heterocycle optionally substituted by alkyl or C(O)OR⁶;
or R¹ and R² together form a 5-membered heterocyclic ring;
R³ is hydrogen or alkyl;
R⁴ is hydrogen, halogen, CN, NO₂, alkyl, or alkoxy;
each R⁶ is independently hydrogen or alkyl;
R⁷ and R⁸ are each independently hydrogen, alkyl, or alkoxyalkyl, or R⁷ and R⁸ taken together with the nitrogen atom to which they are attached form a 6-membered heterocycle which is optionally substituted by alkyl;
each n is independently 1, 2, or 3; and
m is 2, 3, or 4.

54. A process for preparing a compound of formula IV,

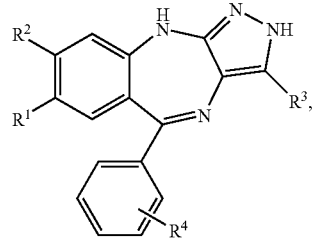

formula IV said process comprising
(a) converting of a benzodiazepine lactam of formula I

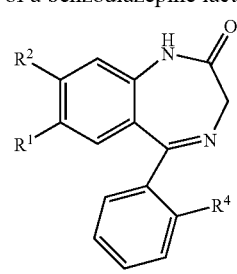

I to the corresponding O-methyl ether of formula V said process comprising
(a) reacting a compound of formula X

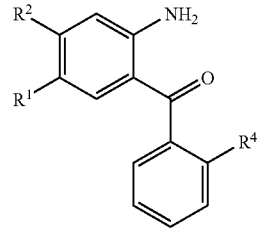

with an amino-chloro-pyrazole derivative of formula XIII

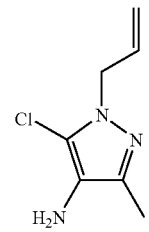

to form a compound of formula XIV

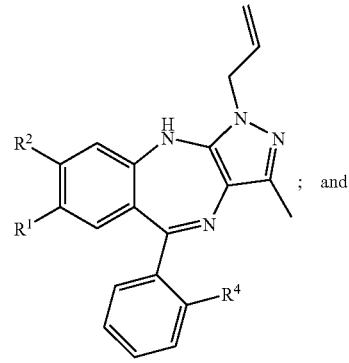

(b) reacting the compound of formula XIV in the presence of diisobutyl aluminum hydride and a nickel catalyst to produce a compound of formula IV;
and wherein, in the above formulas,
R¹ is alkyl, alkoxy, halogen, COOH, COOAlkyl, CN, C(O)N(R⁶)₂, or (OCH₂CH₂)ₙOCH₃;
R² is alkyl, halogen, alkyl substituted by halogen, OH, alkoxy, alkoxy substituted by halogen, phenyl, N(R⁶)₂, (OCH₂CH₂)ₙOCH₃, O(CH₂)ₘNR⁷R⁸, or

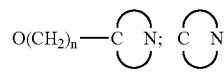

is a 6-membered heterocycle optionally substituted by alkyl or C(O)OR⁶;
or R¹ and R² together form a 5-membered heterocyclic ring;
R³ is hydrogen or alkyl;
R⁴ is hydrogen, halogen, CN, NO₂, alkyl, or alkoxy;
each R⁶ is independently hydrogen or alkyl;
R⁷ and R⁸ are each independently hydrogen, alkyl, or alkoxyalkyl, or R⁷ and R⁸ taken together with the nitrogen atom to which they are attached form a 6-membered heterocycle which is optionally substituted by alkyl;
each n is independently 1, 2, or 3; and
m is 2, 3, or 4.

---

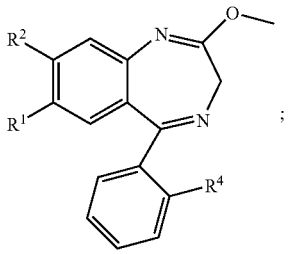

(b) reacting the ether of formula V with the dimethyl acetal of N,N-dimethyl acetamide to form a compound of formula VI

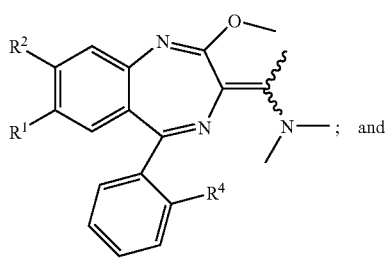

(c) reacting a compound of formula VI with hydrazine to form a compound of formula IV; and
wherein, in the above formulas,
R¹ is alkyl, alkoxy, halogen, COOH, COOAlkyl, CN, C(O)N(R⁶)₂, or (OCH₂CH₂)ₙOCH₃;
R² is alkyl, halogen, alkyl substituted by halogen, OH, alkoxy, alkoxy substituted by halogen, phenyl, N(R⁶)₂, (OCH₂CH₂)ₙOCH₃, O(CH₂)ₘNR⁷R⁸, or

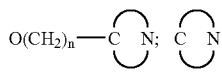

is a 6-membered heterocycle optionally substituted by alkyl or C(O)OR⁶;
or R¹ and R² together form a 5-membered heterocyclic ring;
R³ is hydrogen or alkyl;
R⁴ is hydrogen, halogen, CN, NO₂, alkyl, or alkoxy;
each R⁶ is independently hydrogen or alkyl;
R⁷ and R⁸ are each independently hydrogen, alkyl, or alkoxyalkyl, or R⁷ and R⁸ taken together with the nitrogen atom to which they are attached form a 6-membered heterocycle which is optionally substituted by alkyl;
each n is independently 1, 2, or 3; and
m is 2, 3, or 4.

55. A process of preparing a compound of formula IV,

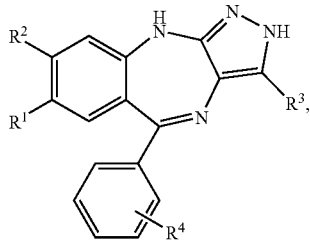

56. A compound of formula XIV

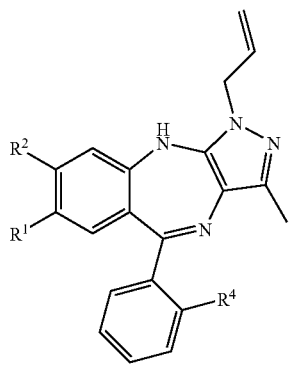

wherein
- $R^1$ is alkyl, alkoxy, halogen, COOH, COOAlkyl, CN, C(O)N($R^6$)$_2$, or (OCH$_2$CH$_2$)$_n$CH$_3$;
- $R^2$ is alkyl, halogen, alkyl substituted by halogen, OH, alkoxy, alkoxy substituted by halogen, phenyl, N($R^6$)$_2$, (OCH$_2$CH$_2$)$_n$OCH$_3$, O(CH$_2$)$_m$N$R^7R^8$, or

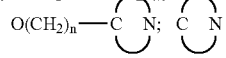
O(CH$_2$)$_n$—C̹ N̹; C̹ N̹ is a 6-membered heterocycle optionally substituted by alkyl or C(O)O$R^6$;
or $R^1$ and $R^2$ together form a 5-membered heterocyclic ring;
- $R^4$ is hydrogen, halogen, CN, NO$_2$, alkyl, or alkoxy;
- each R6 is independently hydrogen or alkyl;
- $R^7$ and $R^8$ are each independently hydrogen, alkyl, or alkoxyalkyl, or $R^7$ and $R^8$ taken together with the nitrogen atom to which they are attached form a 6-membered heterocycle which is optionally substituted by alkyl;
- each n is independently 1, 2, or 3; and
- m is 2, 3, or 4.

57. A compound of claim 56, selected from the group consisting of:
- 5-(2-chlorophenyl)-1,2-dihydro-3,7,8-trimethyl-1-(2-propenyl)-pyrazolo[3,4-b][1,4]benzodiazepine;
- 5-(2-chlorophenyl)-1,2-dihydro-7-fluoro-8-methoxy-3-methyl-1-(2-propenyl)-pyrazolo[3,4-b][1,4]benzodiazepine;
- 5-(2-chlorophenyl)-1,2-dihydro-7,8-dimethoxy-3-methyl-1-(2-propenyl)-pyrazolo[3,4-b][1,4]benzodiazepine;
- 8-chloro-5-(2-chlorophenyl)-1,2-dihydro-7-methoxy-3-methyl-1-(2-propenyl)-pyrazolo[3,4-b][1,4]benzodiazepine;
- 5-(2-chlorophenyl)-1,2-dihydro-8-methoxy-3,7-dimethyl-1-(2-propenyl)-pyrazolo[3,4-b][1,4]benzodiazepine;
- 1,2-dihydro-7,8-dimethoxy-5-(2-methoxyphenyl)-3-methyl-1-(2-propenyl)-pyrazolo[3,4-b][1,4]benzodiazepine;
- 5-(2-chlorophenyl)-8,10-dihydro-7-methyl-1,3-dioxolo[4,5-h]pyrazolo[3,4-b][1,4]benzodiazepine; and
- 7-chloro-5-(2-chlorophenyl)-1,2-dihydro-8-methoxy-3-methyl-1-(2-propenyl)-pyrazolo[3,4-b][1,4]benzodiazepine.

58. A compound of claim 56, selected from the group consisting of:
- 5-(2-chlorophenyl)-1,2-dihydro-8-fluoro-7-methoxy-3-methyl-1-(2-propenyl)-pyrazolo[3,4-b][1,4]benzodiazepine;
- 5-(2-chlorophenyl)-1,2-dihydro-7-methoxy-3-methyl-1-(2-propenyl)-8-trifluoromethyl-pyrazolo[3,4-b][1,4]benzodiazepine;
- 5-(2-chlorophenyl)-1,2-dihydro-7-methoxy-3-methyl-8-phenyl-1-(2-propenyl)-pyrazolo[3,4-b][1,4]benzodiazepine;
- 5-(2-chlorophenyl)-1,2-dihydro-7-methoxy-8-methoxyethoxy-3-methyl-1-(2-propenyl)-pyrazolo[3,4-b][1,4]benzodiazepine;
- 8-chloro-5-(2-chlorophenyl)-1,2-dihydro-3,7-dimethyl-1-(2-propenyl)-pyrazolo[3,4-b][1,4]benzodiazepine;
- 5-(2-chlorophenyl)-1,2-dihydro-7-methoxy-8-(1-methylethoxy)-3-methyl-1-(2-propenyl)-pyrazolo[3,4-b][1,4]benzodiazepine;
- 5-(2-chlorophenyl)-1,2-dihydro-8-methoxy-7-(1-methylethoxy)-3-methyl-1-(2-propenyl)-pyrazolo[3,4-b][1,4]benzodiazepine; and
- 5-(2-chlorophenyl)-1,2-dihydro-8-methoxy-7-methoxyethoxy-3-methyl-1-(2-propenyl)-pyrazolo[3,4-b][1,4]benzodiazepine.

* * * * *